(12) United States Patent
Shasky et al.

(10) Patent No.: US 11,230,723 B2
(45) Date of Patent: *Jan. 25, 2022

(54) CELLULOLYTIC ENZYME COMPOSITIONS AND USES THEREOF

(71) Applicant: Novozymes, Inc., Davis, CA (US)

(72) Inventors: Jeffrey Shasky, Davis, CA (US); Suchindra Maiyuran, Gold River, CA (US); Amanda Fischer, Davis, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/878,267

(22) Filed: May 19, 2020

(65) Prior Publication Data

US 2020/0354763 A1 Nov. 12, 2020

Related U.S. Application Data

(60) Continuation of application No. 16/268,922, filed on Feb. 6, 2019, now Pat. No. 10,662,456, which is a division of application No. 16/122,173, filed on Sep. 5, 2018, now Pat. No. 10,233,473, which is a division of application No. 15/265,460, filed on Sep. 14, 2016, now Pat. No. 10,081,824, which is a division of application No. 14/238,431, filed as application No. PCT/US2012/052163 on Aug. 23, 2012, now Pat. No. 9,476,036.

(60) Provisional application No. 61/526,833, filed on Aug. 24, 2011, provisional application No. 61/577,609, filed on Dec. 19, 2011.

(51) Int. Cl.
*C12P 19/02* (2006.01)
*C07K 14/38* (2006.01)
*C12P 19/14* (2006.01)
*C12N 9/42* (2006.01)

(52) U.S. Cl.
CPC ............. *C12P 19/14* (2013.01); *C07K 14/38* (2013.01); *C12N 9/2437* (2013.01); *C12N 9/2445* (2013.01); *C12P 19/02* (2013.01); *C12Y 302/01004* (2013.01); *C12Y 302/01008* (2013.01); *C12Y 302/01021* (2013.01); *C12Y 302/01037* (2013.01); *C12Y 302/01091* (2013.01); *C12Y 302/01176* (2013.01); *Y02E 50/10* (2013.01); *Y02P 20/52* (2015.11)

(58) Field of Classification Search
CPC ...... C12N 9/2437; C12N 9/2445; Y02E 50/10
See application file for complete search history.

(56) References Cited

U.S. PATENT DOCUMENTS 8,580,536 B2 11/2013 McBrayer et al.
9,416,384 B2 * 8/2016 Iyer ......................... C12P 7/10

FOREIGN PATENT DOCUMENTS

| WO | 2005047499 A1 | 5/2005 |
| WO | 2006078256 A2 | 7/2006 |
| WO | 2010059424 A2 | 5/2010 |
| WO | 2011041397 A1 | 4/2011 |
| WO | 2011057086 A1 | 5/2011 |
| WO | 2011057140 A1 | 5/2011 |

OTHER PUBLICATIONS

Gao et al., 2010, Bio Tech 101(8), 2770-2781.
Banerjee et al., 2010, Biotecnol Bioengg 106(5), 707-720.
Zhang et al., 2010, Jiangxi Feed 2, 1-5—Abstract Only.

* cited by examiner

*Primary Examiner* — Maryam Monshipouri
(74) *Attorney, Agent, or Firm* — David Fazzolare

(57) ABSTRACT

The present invention relates to recombinant filamentous fungal host cells producing cellulolytic enzyme compositions and methods of producing and using the compositions.

26 Claims, 12 Drawing Sheets
Specification includes a Sequence Listing.

SEQUENCE LISTING

```
<160> NUMBER OF SEQ ID NOS: 92

<210> SEQ ID NO 1
<211> LENGTH: 1599
<212> TYPE: DNA
<213> ORGANISM: Aspergillus fumigatus

<400> SEQUENCE: 1
atgctggcct ccaccttctc ctaccgcatg tacaagaccg cgctcatcct ggccgccctt      60
ctgggctctg gccaggctca gcaggtcggt acttcccagg cggaagtgca tccgtccatg     120
acctggcaga gctgcacggc tggcggcagc tgcaccacca caacggcaa ggtggtcatc      180 gacgcgaact ggcgttgggt gcacaaagtc ggcgactaca ccaactgcta caccggcaac     240
acctgggaca cgactatctg ccctgacgat gcgacctgcg catccaactg cgcccttgag     300
ggtgccaact acgaatccac ctatggtgtg accgccagcg gcaattccct ccgcctcaac     360
ttcgtcacca ccagccagca gaagaacatt ggctcgcgtc tgtacatgat gaaggacgac     420
tcgacctacg agatgtttaa gctgctgaac caggagttca ccttcgatgt cgatgtctcc     480
aacctcccct gcggtctcaa cggtgctctg tactttgtcg ccatggacgc cgacggtggc     540
atgtccaagt acccaaccaa caaggccggt gccaagtacg gtactggata ctgtgactcg     600
cagtgccctc gcgacctcaa gttcatcaac ggtcaggcca acgtcgaagg gtggcagccc     660
tcctccaacg atgccaatgc gggtaccggc aaccacgggt cctgctgcgc ggagatggat     720
atctgggagg ccaacagcat ctccacggcc ttcaccccc atccgtgcga cacgcccggc     780
caggtgatgt gcaccggtga tgcctgcggt ggcacctaca gctccgaccg ctacggcggc     840
acctgcgacc ccgacggatg tgatttcaac tccttccgcc agggcaacaa gaccttctac     900
ggccctggca tgaccgtcga caccaagagc aagtttaccg tcgtcaccca gttcatcacc     960
gacgacggca cctccagcgg caccctcaag gagatcaagc gcttctacgt gcagaacggc    1020
aaggtgatcc ccaactcgga gtcgacctgg accggcgtca gcggcaactc catcaccacc    1080
gagtactgca ccgcccagaa gagcctgttc caggaccaga acgtcttcga aaagcacggc    1140
```

-continued

```
ggcctcgagg gcatgggtgc tgccctcgcc cagggtatgg ttctcgtcat gtccctgtgg    1200
gatgatcact cggccaacat gctctggctc gacagcaact acccgaccac tgcctcttcc    1260
accactcccg gcgtcgcccg tggtacctgc gacatctcct ccggcgtccc tgcggatgtc    1320
gaggcgaacc accccgacgc ctacgtcgtc tactccaaca tcaaggtcgg ccccatcggc    1380
tcgaccttca acagcggtgg ctcgaacccc ggtggcggaa ccaccacgac aactaccacc    1440
cagcctacta ccaccacgac cacggctgga aaccctggcg gcaccggagt cgcacagcac    1500
tatggccagt gtggtggaat cggatggacc ggacccacaa cctgtgccag cccttatacc    1560
tgccagaagc tgaatgatta ttactctcag tgcctgtag                          1599
```

<210> SEQ ID NO 2
<211> LENGTH: 532
<212> TYPE: PRT
<213> ORGANISM: Aspergillus fumigatus

<400> SEQUENCE: 2

```
Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Gln Val Gly Thr Ser
                20                  25                  30

Gln Ala Glu Val His Pro Ser Met Thr Trp Gln Ser Cys Thr Ala Gly
            35                  40                  45

Gly Ser Cys Thr Thr Asn Asn Gly Lys Val Val Ile Asp Ala Asn Trp
        50                  55                  60

Arg Trp Val His Lys Val Gly Asp Tyr Thr Asn Cys Tyr Thr Gly Asn
65                  70                  75                  80

Thr Trp Asp Thr Thr Ile Cys Pro Asp Asp Ala Thr Cys Ala Ser Asn
                85                  90                  95

Cys Ala Leu Glu Gly Ala Asn Tyr Glu Ser Thr Tyr Gly Val Thr Ala
            100                 105                 110

Ser Gly Asn Ser Leu Arg Leu Asn Phe Val Thr Ser Gln Gln Lys
        115                 120                 125

Asn Ile Gly Ser Arg Leu Tyr Met Met Lys Asp Asp Ser Thr Tyr Glu
    130                 135                 140

Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                165                 170                 175

Ala Asp Gly Gly Met Ser Lys Tyr Pro Thr Asn Lys Ala Gly Ala Lys
            180                 185                 190

Tyr Gly Thr Gly Tyr Cys Asp Ser Gln Cys Pro Arg Asp Leu Lys Phe
        195                 200                 205

Ile Asn Gly Gln Ala Asn Val Glu Gly Trp Gln Pro Ser Ser Asn Asp
    210                 215                 220

Ala Asn Ala Gly Thr Gly Asn His Gly Ser Cys Cys Ala Glu Met Asp
225                 230                 235                 240

Ile Trp Glu Ala Asn Ser Ile Ser Thr Ala Phe Thr Pro His Pro Cys
                245                 250                 255

Asp Thr Pro Gly Gln Val Met Cys Thr Gly Asp Ala Cys Gly Gly Thr
            260                 265                 270

Tyr Ser Ser Asp Arg Tyr Gly Gly Thr Cys Asp Pro Asp Gly Cys Asp
        275                 280                 285

Phe Asn Ser Phe Arg Gln Gly Asn Lys Thr Phe Tyr Gly Pro Gly Met
```

```
                290                 295                 300
Thr Val Asp Thr Lys Ser Lys Phe Thr Val Thr Gln Phe Ile Thr
305                 310                 315                 320

Asp Asp Gly Thr Ser Ser Gly Thr Leu Lys Glu Ile Lys Arg Phe Tyr
                325                 330                 335

Val Gln Asn Gly Lys Val Ile Pro Asn Ser Glu Ser Thr Trp Thr Gly
                340                 345                 350

Val Ser Gly Asn Ser Ile Thr Thr Glu Tyr Cys Thr Ala Gln Lys Ser
                355                 360                 365

Leu Phe Gln Asp Gln Asn Val Phe Glu Lys His Gly Gly Leu Glu Gly
    370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
                405                 410                 415

Thr Ala Ser Ser Thr Thr Pro Gly Val Ala Arg Gly Thr Cys Asp Ile
                420                 425                 430

Ser Ser Gly Val Pro Ala Asp Val Glu Ala Asn His Pro Asp Ala Tyr
                435                 440                 445

Val Val Tyr Ser Asn Ile Lys Val Gly Pro Ile Gly Ser Thr Phe Asn
                450                 455                 460

Ser Gly Gly Ser Asn Pro Gly Gly Gly Thr Thr Thr Thr Thr Thr Thr
465                 470                 475                 480

Gln Pro Thr Thr Thr Thr Thr Thr Ala Gly Asn Pro Gly Gly Thr Gly
                    485                 490                 495

Val Ala Gln His Tyr Gly Gln Cys Gly Gly Ile Gly Trp Thr Gly Pro
                500                 505                 510

Thr Thr Cys Ala Ser Pro Tyr Thr Cys Gln Lys Leu Asn Asp Tyr Tyr
                515                 520                 525

Ser Gln Cys Leu
    530

<210> SEQ ID NO 3
<211> LENGTH: 1713
<212> TYPE: DNA
<213> ORGANISM: Aspergillus fumigatus

<400> SEQUENCE: 3
atgaagcacc ttgcatcttc catcgcattg actctactgt tgcctgccgt gcaggcccag      60
cagaccgtat ggggccaatg tatgttctgg ctgtcactgg aataagactg tatcaactgc     120
tgatatgctt ctaggtggcg gccaaggctg gtctggcccg acgagctgtg ttgccggcgc     180
agcctgtagc acactgaatc cctgtatgtt agatatcgtc ctgagtggag acttatactg     240
acttccttag actacgctca gtgtatcccg ggagccaccg cgacgtccac caccctcacg     300
acgacgacgg cggcgacgac gacatcccag accaccacca aacctaccac gactggtcca     360
actacatccg cacccaccgt gaccgcatcc ggtaacccct tcagcggcta ccagctgtat     420 gccaaccccct actactcctc cgaggtccat actctggcca tgccttctct gcccagctcg     480
ctgcagccca aggctagtgc tgttgctgaa gtgccctcat tgtttggct gtaagtggcc     540 ttatcccaat actgagacca actctctgac agtcgtagcg acgttgccgc caaggtgccc     600
actatgggaa cctacctggc cgacattcag gccaagaaca aggccggcgc caaccctcct     660
atcgctggta tcttcgtggt ctacgacttg ccggaccgtg actgcgccgc tctggccagt     720
```

```
aatggcgagt actcaattgc caacaacggt gtggccaact acaaggcgta cattgacgcc    780
atccgtgctc agctggtgaa gtactctgac gttcacacca tcctcgtcat cggtaggccg    840
tacacctccg ttgcgcgccg cctttctctg acatcttgca gaacccgaca gcttggccaa    900
cctggtgacc aacctcaacg tcgccaaatg cgccaatgcg cagagcgcct acctggagtg    960
tgtcgactat gctctgaagc agctcaacct gcccaacgtc gccatgtacc tcgacgcagg   1020
tatgcctcac ttcccgcatt ctgtatccct tccagacact aactcatcag gccatgcggg   1080
ctggctcgga tggcccgcca acttgggccc cgccgcaaca ctcttcgcca agtctacac    1140
cgacgcgggt tcccccgcgg ctgttcgtgg cctggccacc aacgtcgcca actacaacgc   1200
ctggtcgctc agtacctgcc cctcctacac ccagggagac cccaactgcg acgagaagaa   1260
gtacatcaac gccatggcgc tcttctcaa ggaagccggc ttcgatgccc acttcatcat    1320
ggatacctgt aagtgcttat ccaatcgcc gatgtgtgcc gactaatcaa tgtttcagcc    1380
cggaatggcg tccagcccac gaagcaaaac gcctggggtg actggtgcaa cgtcatcggc   1440
accggcttcg gtgttcgccc ctcgactaac accggcgatc cgctccagga tgcctttgtg   1500
tggatcaagc ccggtggaga gagtgatggc acgtccaact cgacttcccc ccggtatgac   1560
gcgcactgcg gatatagtga tgctctgcag cctgctcctg aggctggtac ttggttccag   1620
gtatgtcatc cattagccag atgagggata agtgactgac ggacctaggc ctactttgag   1680
cagcttctga ccaacgctaa cccgtccttt taa                                1713

<210> SEQ ID NO 4
<211> LENGTH: 454
<212> TYPE: PRT
<213> ORGANISM: Aspergillus fumigatus

<400> SEQUENCE: 4

Met Lys His Leu Ala Ser Ser Ile Ala Leu Thr Leu Leu Pro Ala
1               5                   10                  15

Val Gln Ala Gln Gln Thr Val Trp Gly Gln Cys Gly Gly Gln Gly Trp
            20                  25                  30

Ser Gly Pro Thr Ser Cys Val Ala Gly Ala Ala Cys Ser Thr Leu Asn
        35                  40                  45

Pro Tyr Tyr Ala Gln Cys Ile Pro Gly Ala Thr Ala Thr Ser Thr Thr
    50                  55                  60

Leu Thr Thr Thr Thr Ala Ala Thr Thr Thr Ser Gln Thr Thr Thr Lys
65                  70                  75                  80

Pro Thr Thr Thr Gly Pro Thr Ser Ala Pro Thr Val Thr Ala Ser
                85                  90                  95

Gly Asn Pro Phe Ser Gly Tyr Gln Leu Tyr Ala Asn Pro Tyr Tyr Ser
            100                 105                 110

Ser Glu Val His Thr Leu Ala Met Pro Ser Leu Pro Ser Ser Leu Gln
        115                 120                 125

Pro Lys Ala Ser Ala Val Ala Glu Val Pro Ser Phe Val Trp Leu Asp
    130                 135                 140

Val Ala Ala Lys Val Pro Thr Met Gly Thr Tyr Leu Ala Asp Ile Gln
145                 150                 155                 160

Ala Lys Asn Lys Ala Gly Ala Asn Pro Ile Ala Gly Ile Phe Val
                165                 170                 175

Val Tyr Asp Leu Pro Asp Arg Asp Cys Ala Ala Leu Ala Ser Asn Gly
            180                 185                 190

Glu Tyr Ser Ile Ala Asn Asn Gly Val Ala Asn Tyr Lys Ala Tyr Ile
```

```
                195                 200                 205
Asp Ala Ile Arg Ala Gln Leu Val Lys Tyr Ser Asp Val His Thr Ile
    210                 215                 220

Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
                245                 250                 255

Tyr Ala Leu Lys Gln Leu Asn Leu Pro Asn Val Ala Met Tyr Leu Asp
            260                 265                 270

Ala Gly His Ala Gly Trp Leu Gly Trp Pro Ala Asn Leu Gly Pro Ala
        275                 280                 285

Ala Thr Leu Phe Ala Lys Val Tyr Thr Asp Ala Gly Ser Pro Ala Ala
    290                 295                 300

Val Arg Gly Leu Ala Thr Asn Val Ala Asn Tyr Asn Ala Trp Ser Leu
305                 310                 315                 320

Ser Thr Cys Pro Ser Tyr Thr Gln Gly Asp Pro Asn Cys Asp Glu Lys
                325                 330                 335

Lys Tyr Ile Asn Ala Met Ala Pro Leu Leu Lys Glu Ala Gly Phe Asp
            340                 345                 350

Ala His Phe Ile Met Asp Thr Ser Arg Asn Gly Val Gln Pro Thr Lys
        355                 360                 365

Gln Asn Ala Trp Gly Asp Trp Cys Asn Val Ile Gly Thr Gly Phe Gly
    370                 375                 380

Val Arg Pro Ser Thr Asn Thr Gly Asp Pro Leu Gln Asp Ala Phe Val
385                 390                 395                 400

Trp Ile Lys Pro Gly Gly Glu Ser Asp Gly Thr Ser Asn Ser Thr Ser
                405                 410                 415

Pro Arg Tyr Asp Ala His Cys Gly Tyr Ser Asp Ala Leu Gln Pro Ala
            420                 425                 430

Pro Glu Ala Gly Thr Trp Phe Gln Ala Tyr Phe Glu Gln Leu Leu Thr
        435                 440                 445

Asn Ala Asn Pro Ser Phe
    450

<210> SEQ ID NO 5
<211> LENGTH: 3060
<212> TYPE: DNA
<213> ORGANISM: Aspergillus fumigatus

<400> SEQUENCE: 5
atgagattcg gttggctcga ggtggccgct ctgacggccg cttctgtagc caatgcccag     60
gtttgtgatg ctttcccgtc attgtttcgg atatagttga caatagtcat ggaaataatc    120
aggaattggc tttctctcca ccattctacc cttcgccttg gctgatggc caggggagagt    180 gggcagatgc ccatcgacgc gccgtcgaga tcgtttctca gatgacactg gcggagaagg    240
ttaaccttac aacgggtact gggtgggttg cgacttttt gttgacagtg agctttcttc    300
actgaccatc tacacagatg ggaaatggac cgatgcgtcg gtcaaaccgg cagcgttccc    360
aggtaagctt gcaattctgc aacaacgtgc aagtgtagtt gctaaaacgc ggtggtgcag    420
acttggtatc aactggggtc tttgtggcca ggattcccct tgggtatcc gtttctgtga    480 gctatacccg cggagtcttt cagtccttgt attatgtgct gatgattgtc tctgtatagc    540
tgacctcaac tccgccttcc ctgctggtac taatgtcgcc gcgacatggg acaagacact    600
cgcctacctt cgtggcaagg ccatgggtga ggaattcaac gacaagggcg tggacatttt    660
```

```
gctgggcct gctgctggtc ctctcggcaa atacccggac ggcggcagaa tctgggaagg    720
cttctctcct gatccggttc tcactggtgt acttttcgcc gaaactatca agggtatcca    780
agacgcgggt gtgattgcta ctgccaagca ttacattctg aatgaacagg agcatttccg    840
acaggttggc gaggcccagg gatatggtta caacatcacg gagacgatca gctccaacgt    900
ggatgacaag accatgcacg agttgtacct ttggtgagta gttgacactg caaatgagga    960
ccttgattga tttgactgac ctggaatgca ggcccttttgc agatgctgtg cgcggtaaga   1020
ttttccgtag acttgacctc gcgacgaaga aatcgctgac gaaccatcgt agctggcgtt   1080
ggcgctgtca tgtgttccta caatcaaatc aacaacagct acggttgtca aaacagtcaa   1140
actctcaaca agctcctcaa ggctgagctg gcttccaag gcttcgtcat gagtgactgg   1200
agcgctcacc acagcggtgt cggcgctgcc ctcgctgggt tggatatgtc gatgcctgga   1260
gacatttcct tcgacgacgg actctccttc tggggcacga acctaactgt cagtgttctt   1320
aacggcaccg ttccagcctg gcgtgtcgat gacatggctg ttcgtatcat gaccgcgtac   1380
tacaaggttg gtcgtgaccg tcttcgtatt cccctaact tcagctcctg gacccgggat    1440
gagtacggct gggagcattc tgctgtctcc gagggagcct ggaccaaggt gaacgacttc   1500
gtcaatgtgc agcgcagtca ctctcagatc atccgtgaga ttggtgccgc tagtacagtg   1560
ctcttgaaga acacgggtgc tcttcctttg accggcaagg aggttaaagt gggtgttctc   1620
ggtgaagacg ctggttccaa cccgtggggt gctaacggct gccccgaccg cggctgtgat   1680
aacggcactc ttgctatggc ctgggggtagt ggtactgcca acttcccctta ccttgtcacc   1740 cccgagcagg ctatccagcg agaggtcatc agcaacggcg gcaatgtctt tgctgtgact   1800
gataacgggg ctctcagcca gatggcagat gttgcatctc aatccaggtg agtgcgggct   1860
cttagaaaaa gaacgttctc tgaatgaagt ttttaacca ttgcgaacag cgtgtctttg   1920
gtgtttgtca acgccgactc tggagagggt ttcatcagtg tcgacggcaa cgagggtgac   1980
cgcaaaaatc tcactctgtg gaagaacggc gaggccgtca ttgacactgt tgtcagccac   2040
tgcaacaaca cgattgtggt tattcacagt gttgggcccg tcttgatcga ccggtggtat   2100
gataacccca acgtcactgc catcatctgg gccggcttgc ccggtcagga gagtggcaac   2160
tccctggtcg acgtgctcta tggccgcgtc aaccccagcg ccaagacccc gttcacctgg   2220
ggcaagactc gggagtctta cggggctccc ttgctcaccg agcctaacaa tggcaatggt   2280
gctccccagg atgatttcaa cgagggcgtc ttcattgact accgtcactt tgacaagcgc   2340
aatgagaccc ccatttatga gtttggccat ggccttgagct acaccacctt tggttactct   2400
caccttcggg ttcaggccct caatagttcg agttcggcat atgtcccgac tagcggagag   2460
accaagcctg cgccaaccta tggtgagatc ggtagtgccg ccgactacct gtatcccgag   2520
ggtctcaaaa gaattaccaa gtttatttac ccttggctca actcgaccga cctcgaggat   2580
tcttctgacg acccgaacta cggctgggag gactcggagt acattcccga aggcgctagg   2640
gatgggtctc ctcaaccccct cctgaaggct ggcggcgctc ctggtggtaa ccctacccttt   2700 tatcaggatc ttgttagggt gtcggccacc ataaccaaca ctggtaacgt cgccggttat   2760
gaagtccctc aattggtgag tgacccgcat gttccttgcg ttgcaatttg ctaactcgc   2820 ttctagtatg tttcactggg cggaccgaac gagcctcggg tcgttctgcg caagttcgac   2880
cgaatcttcc tggctcctgg ggagcaaaag gtttggacca cgactcttaa ccgtcgtgat   2940
ctcgccaatt gggatgtgga ggctcaggac tgggtcatca caaagtaccc caagaaagtg   3000
```
cacgtcggca gctcctcgcg taagctgcct ctgagagcgc ctctgccccg tgtctactag    3060

<210> SEQ ID NO 6
<211> LENGTH: 863
<212> TYPE: PRT
<213> ORGANISM: Aspergillus fumigatus

<400> SEQUENCE: 6

```
Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Leu Asn Glu Gln Glu His Phe Arg Gln Val Gly Glu Ala Gln Gly
        195                 200                 205

Tyr Gly Tyr Asn Ile Thr Glu Thr Ile Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
            260                 265                 270

Gly Phe Gln Gly Phe Val Met Ser Asp Trp Ser Ala His His Ser Gly
        275                 280                 285

Val Gly Ala Ala Leu Ala Gly Leu Asp Met Ser Met Pro Gly Asp Ile
    290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
            340                 345                 350

Pro Pro Asn Phe Ser Ser Trp Thr Arg Asp Glu Tyr Gly Trp Glu His
        355                 360                 365
```

-continued

```
Ser Ala Val Ser Glu Gly Ala Trp Thr Lys Val Asn Asp Phe Val Asn
    370                 375                 380
Val Gln Arg Ser His Ser Gln Ile Ile Arg Glu Ile Gly Ala Ala Ser
385                 390                 395                 400
Thr Val Leu Leu Lys Asn Thr Gly Ala Leu Pro Leu Thr Gly Lys Glu
                405                 410                 415
Val Lys Val Gly Val Leu Gly Glu Asp Ala Gly Ser Asn Pro Trp Gly
                420                 425                 430
Ala Asn Gly Cys Pro Asp Arg Gly Cys Asp Asn Gly Thr Leu Ala Met
            435                 440                 445
Ala Trp Gly Ser Gly Thr Ala Asn Phe Pro Tyr Leu Val Thr Pro Glu
    450                 455                 460
Gln Ala Ile Gln Arg Glu Val Ile Ser Asn Gly Gly Asn Val Phe Ala
465                 470                 475                 480
Val Thr Asp Asn Gly Ala Leu Ser Gln Met Ala Asp Val Ala Ser Gln
                485                 490                 495
Ser Ser Val Ser Leu Val Phe Val Asn Ala Asp Ser Gly Glu Gly Phe
            500                 505                 510
Ile Ser Val Asp Gly Asn Glu Gly Asp Arg Lys Asn Leu Thr Leu Trp
    515                 520                 525
Lys Asn Gly Glu Ala Val Ile Asp Thr Val Val Ser His Cys Asn Asn
530                 535                 540
Thr Ile Val Ile His Ser Val Gly Pro Val Leu Ile Asp Arg Trp
545                 550                 555                 560
Tyr Asp Asn Pro Asn Val Thr Ala Ile Ile Trp Ala Gly Leu Pro Gly
                565                 570                 575
Gln Glu Ser Gly Asn Ser Leu Val Asp Val Leu Tyr Gly Arg Val Asn
            580                 585                 590
Pro Ser Ala Lys Thr Pro Phe Thr Trp Gly Lys Thr Arg Glu Ser Tyr
    595                 600                 605
Gly Ala Pro Leu Leu Thr Glu Pro Asn Asn Gly Asn Gly Ala Pro Gln
    610                 615                 620
Asp Asp Phe Asn Glu Gly Val Phe Ile Asp Tyr Arg His Phe Asp Lys
625                 630                 635                 640
Arg Asn Glu Thr Pro Ile Tyr Glu Phe Gly His Gly Leu Ser Tyr Thr
                645                 650                 655
Thr Phe Gly Tyr Ser His Leu Arg Val Gln Ala Leu Asn Ser Ser Ser
            660                 665                 670
Ser Ala Tyr Val Pro Thr Ser Gly Glu Thr Lys Pro Ala Pro Thr Tyr
    675                 680                 685
Gly Glu Ile Gly Ser Ala Ala Asp Tyr Leu Tyr Pro Glu Gly Leu Lys
    690                 695                 700
Arg Ile Thr Lys Phe Ile Tyr Pro Trp Leu Asn Ser Thr Asp Leu Glu
705                 710                 715                 720
Asp Ser Ser Asp Asp Pro Asn Tyr Gly Trp Glu Asp Ser Glu Tyr Ile
                725                 730                 735
Pro Glu Gly Ala Arg Asp Gly Ser Pro Gln Pro Leu Leu Lys Ala Gly
            740                 745                 750
Gly Ala Pro Gly Gly Asn Pro Thr Leu Tyr Gln Asp Leu Val Arg Val
    755                 760                 765
Ser Ala Thr Ile Thr Asn Thr Gly Asn Val Ala Gly Tyr Glu Val Pro
770                 775                 780
Gln Leu Tyr Val Ser Leu Gly Gly Pro Asn Glu Pro Arg Val Val Leu
```

```
                785                 790                795                800
Arg Lys Phe Asp Arg Ile Phe Leu Ala Pro Gly Glu Gln Lys Val Trp
                    805                 810                 815

Thr Thr Thr Leu Asn Arg Arg Asp Leu Ala Asn Trp Asp Val Glu Ala
                    820                 825                 830

Gln Asp Trp Val Ile Thr Lys Tyr Pro Lys Lys Val His Val Gly Ser
                    835                 840                 845

Ser Ser Arg Lys Leu Pro Leu Arg Ala Pro Leu Pro Arg Val Tyr
                    850                 855                 860

<210> SEQ ID NO 7
<211> LENGTH: 835
<212> TYPE: DNA
<213> ORGANISM: Penicillium sp.

<400> SEQUENCE: 7
atgctgtctt cgacgactcg caccctcgcc tttacaggcc ttgcgggcct tctgtccgct    60
cccctggtca aggcccatgg ctttgtccag ggcattgtca tcggtgacca attgtaagtc   120
cctctcttgc agttctgtcg attaactgct ggactgcttg cttgactccc tgctgactcc   180
caacagctac agcgggtaca tcgtcaactc gttcccctac gaatccaacc cacccccgt    240
catcggctgg gccacgaccg ccaccgacct gggcttcgtc gacggcacag ataccaagg    300
cccggacatc atctgccacc ggaatgcgac gcccgcgccg ctgacagccc ccgtggccgc   360
cggcggcacc gtcgagctgc agtggacgcc gtggccggac agccaccacg acccgtcat    420
cacctacctg gcgccgtgca acggcaactg ctcgaccgtc gacaagacga cgctggagtt   480
cttcaagatc gaccagcagg gcctgatcga cgacacgagc ccgccgggca cctgggcgtc   540
ggacaacctc atcgccaaca caatagctg accgtcacc attcccaaca gcgtcgcccc    600
cggcaactac gtcctgcgcc acgagatcat cgccctgcac tcggccaaca acaaggacgg   660
cgcccagaac taccccccagt gcatcaacat cgaggtcacg ggcggcggct ccgacgcgcc   720
tgagggtact ctgggcgagg atctctacca tgacaccgac ccgggcattc tggtcgacat   780
ttacgagccc attgcgacgt ataccattcc ggggccgcct gagccgacgt tctag        835

<210> SEQ ID NO 8
<211> LENGTH: 253
<212> TYPE: PRT
<213> ORGANISM: Penicillium sp.

<400> SEQUENCE: 8

Met Leu Ser Ser Thr Thr Arg Thr Leu Ala Phe Thr Gly Leu Ala Gly
1               5                   10                  15

Leu Leu Ser Ala Pro Leu Val Lys Ala His Gly Phe Val Gln Gly Ile
                20                  25                  30

Val Ile Gly Asp Gln Phe Tyr Ser Gly Tyr Ile Val Asn Ser Phe Pro
            35                  40                  45

Tyr Glu Ser Asn Pro Pro Val Ile Gly Trp Ala Thr Thr Ala Thr
    50                  55                  60

Asp Leu Gly Phe Val Asp Gly Thr Gly Tyr Gln Gly Pro Asp Ile Ile
65                  70                  75                  80

Cys His Arg Asn Ala Thr Pro Ala Pro Leu Thr Ala Pro Val Ala Ala
                85                  90                  95

Gly Gly Thr Val Glu Leu Gln Trp Thr Pro Trp Pro Asp Ser His His
            100                 105                 110
```

Gly Pro Val Ile Thr Tyr Leu Ala Pro Cys Asn Gly Asn Cys Ser Thr
            115                 120                 125

Val Asp Lys Thr Thr Leu Glu Phe Phe Lys Ile Asp Gln Gln Gly Leu
    130                 135                 140

Ile Asp Asp Thr Ser Pro Pro Gly Thr Trp Ala Ser Asp Asn Leu Ile
145                 150                 155                 160

Ala Asn Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
        195                 200                 205

Thr Gly Gly Gly Ser Asp Ala Pro Glu Gly Thr Leu Gly Glu Asp Leu
    210                 215                 220

Tyr His Asp Thr Asp Pro Gly Ile Leu Val Asp Ile Tyr Glu Pro Ile
225                 230                 235                 240

Ala Thr Tyr Thr Ile Pro Gly Pro Pro Glu Pro Thr Phe
                245                 250

<210> SEQ ID NO 9
<211> LENGTH: 1145
<212> TYPE: DNA
<213> ORGANISM: Aspergillus fumigatus

<400> SEQUENCE: 9
atgcgtttct cccttgccgc caccgctctt ctcgctggcc tggccacggc agcgccttcg      60
agcaacaaga caacgtcaa tcttgataag cttgctcggc gtaatggcat gctttggttc     120
ggcactgcag ccgatatccc tggtacctca gaaacaaccg acaagcctta tctgagcatc     180
ctgcgcaagc agttcggcga atgacaccc gcaaacgcat gaaggtgag ccagagtgat      240 agtacacctc atctcgtgtc ggcgctgacc agacgatgtt attcacatag ttcatgtata     300
ccgagcccga gcagaatgtc ttcaacttca ctcaagggga ctacttcatg gacttggccg     360
atcactatgg tcacgccgtg cgctgccata acctcgtctg gccagccaa gtgtccgact      420 gggtcaccte caggaactgg accgccacag aactcaaaga agtgatgaag aaccacatat     480
tcaagaccgt ccaacatttt ggcaagcgct gctacgcgtg ggacgtcgtc aatgaagcta     540
ttaatgggga cgggaccttt tcctccagtg tgtggtacga cacaattggc gaggaatact     600
tctaccttgc attccagtat gcccaggaag ccctggcgca gattcacgcc aaccaggtca     660
agctttacta taacgactat ggcattgaga accccggccc caaggcagat gctgttctga     720
agctagtcgc cgagttgcgg aagcggggca ttcgcattga cggagtcggt ctcgagtccc     780
acttcatcgt cggcgagact ccttcgctgg ctgaccagct cgccaccaag aaggcttata     840
tcgaggccgg acttgaggtc gccatcaccg aacttgacgt ccgcttttct caggccccgt     900
tctacaccgc cgaggcccaa aagcagcagg ctgccgacta ctatgctagc gtcgccagtt     960
gcaagcatgc cggaccgcgc tgtgttggtg ttgtagtctg ggatttcgat gacgcctact    1020
cgtggattcc gggtaccttc gagggacagg gtggcgcctg tctatataat gagacactcg    1080
aggtgaagcc ggccttctat gctgctgccg aggcgttgga gaacaagccc tgcactgtat    1140
gctag                                                               1145

<210> SEQ ID NO 10
<211> LENGTH: 364
<212> TYPE: PRT

<213> ORGANISM: Aspergillus fumigatus

<400> SEQUENCE: 10

Met Arg Phe Ser Leu Ala Ala Thr Ala Leu Ala Gly Leu Ala Thr
1               5                   10                  15

Ala Ala Pro Ser Ser Asn Lys Asn Asn Val Asn Leu Asp Lys Leu Ala
            20                  25                  30

Arg Arg Asn Gly Met Leu Trp Phe Gly Thr Ala Ala Asp Ile Pro Gly
        35                  40                  45

Thr Ser Glu Thr Thr Asp Lys Pro Tyr Leu Ser Ile Leu Arg Lys Gln
    50                  55                  60

Phe Gly Glu Met Thr Pro Ala Asn Ala Leu Lys Val Ser Gln Ser Asp
65                  70                  75                  80

Phe Met Tyr Thr Glu Pro Glu Gln Asn Val Phe Asn Phe Thr Gln Gly
                85                  90                  95

Asp Tyr Phe Met Asp Leu Ala Asp His Tyr Gly His Ala Val Arg Cys
            100                 105                 110

His Asn Leu Val Trp Ala Ser Gln Val Ser Asp Trp Val Thr Ser Arg
        115                 120                 125

Asn Trp Thr Ala Thr Glu Leu Lys Glu Val Met Lys Asn His Ile Phe
    130                 135                 140

Lys Thr Val Gln His Phe Gly Lys Arg Cys Tyr Ala Trp Asp Val Val
145                 150                 155                 160

Asn Glu Ala Ile Asn Gly Asp Gly Thr Phe Ser Ser Val Trp Tyr
                165                 170                 175

Asp Thr Ile Gly Glu Glu Tyr Phe Tyr Leu Ala Phe Gln Tyr Ala Gln
            180                 185                 190

Glu Ala Leu Ala Gln Ile His Ala Asn Gln Val Lys Leu Tyr Tyr Asn
        195                 200                 205

Asp Tyr Gly Ile Glu Asn Pro Gly Pro Lys Ala Asp Ala Val Leu Lys
    210                 215                 220

Leu Val Ala Glu Leu Arg Lys Arg Gly Ile Arg Ile Asp Gly Val Gly
225                 230                 235                 240

Leu Glu Ser His Phe Ile Val Gly Glu Thr Pro Ser Leu Ala Asp Gln
                245                 250                 255

Leu Ala Thr Lys Lys Ala Tyr Ile Glu Ala Gly Leu Glu Val Ala Ile
            260                 265                 270

Thr Glu Leu Asp Val Arg Phe Ser Gln Ala Pro Phe Tyr Thr Ala Glu
        275                 280                 285

Ala Gln Lys Gln Gln Ala Ala Asp Tyr Tyr Ala Ser Val Ala Ser Cys
    290                 295                 300

Lys His Ala Gly Pro Arg Cys Val Gly Val Val Val Trp Asp Phe Asp
305                 310                 315                 320

Asp Ala Tyr Ser Trp Ile Pro Gly Thr Phe Glu Gly Gln Gly Gly Ala
                325                 330                 335

Cys Leu Tyr Asn Glu Thr Leu Glu Val Lys Pro Ala Phe Tyr Ala Ala
            340                 345                 350

Ala Glu Ala Leu Glu Asn Lys Pro Cys Thr Val Cys
        355                 360

<210> SEQ ID NO 11
<211> LENGTH: 1400
<212> TYPE: DNA
<213> ORGANISM: Aspergillus fumigatus

<400> SEQUENCE: 11

```
atggtcgtcc tcagcaagct cgtcagcagc attctctttg tctccctggt ttcggcgggc      60
gtgatcgacg aacgccaggc agccggcatc aaccaggcgt ttacctccca tggcaagaag     120
tactttggca ccgccagtga ccaagctctg ctccagaagt cgcagaatga ggccattgtg     180
cgcaaagact ttggccagct gacgccggag aatagcatga agtgggatgc gactgagcgt     240
aggtctctcg gccactgtgg ctgacgttaa cttgttgaca tgactgtctg tgtagcatcg     300
caaggaagat tcaacttcgc tggtgctgat ttcctggtat gcaatctgct catctcggtc     360
gagctcctgc tgaaggacaa taaataggtc aactatgcaa aacagaatgg caagaaggtc     420
cgcggacaca ccttaggtat tcatgcgccc tcacggcatt tcgaggatac agccaagctg     480
acagtgtagt ctggcactcc caactcccgt cctgggtgtc ggctatcagc gacaaaaaca     540
ccctgacctc ggtgctgaag aaccacatca ccaccgtcat gacccggtac aagggccaga     600
tctacgcctg gtattttgc cctctatccc acacaatgcc agcccagct aatagctgca       660
aaggacgtcg tcaacgagat cttcaacgag acggctcccc tccgcacag cgtcttctcc      720
cgcgtgctgg cgaggactt tgtgcggatt gccttcgaga cggcgcgctc tgtggatccc      780
tcggcgaagc tgtacatcaa cgattacaag taagcttgtg gttttgtcga gagatgtact     840
ccgtcctgga tctgaccatc acagtctcga ctcggctagc tatggcaaaa cccaggggat     900
ggtgagatat gtcaagaagt ggctggctgc gggcattcct atcgatggaa tcggtgagca     960
caggtcgcgg agctgtgtgt gatgattgta cgctgactct tcctgaaggc actcaaaccc    1020
accttggtgc gggtgcttcg tccagcgtca aaggataagt ctccttggtt ttcttgccta    1080
cgtaacgctg accccccgtg tacagcattg actgctcttg cgtcttccgg cgtctctgag    1140
gtcgccatta ccgagctgga tatcgcgggt gcgagctccc aggactacgt caatgtatgt    1200
ctcctgattg ccagtggcag ggtcatcgat actaatagaa acaggtcgtc aaggcatgcc    1260
tggatgtccc caagtgtgtg ggaatcaccg tctgggggt gtcggacagg gactcgtggc     1320
gctccggctc gtctccgctg ctgttcgaca gcaactacca gcccaaggcg gcgtataatg    1380
ccatcattgc tgctctctga                                                 1400
```

<210> SEQ ID NO 12
<211> LENGTH: 323
<212> TYPE: PRT
<213> ORGANISM: Aspergillus fumigatus

<400> SEQUENCE: 12

```
Met Val Val Leu Ser Lys Leu Val Ser Ser Ile Leu Phe Val Ser Leu
1               5                   10                  15

Val Ser Ala Gly Val Ile Asp Glu Arg Gln Ala Ala Gly Ile Asn Gln
            20                  25                  30

Ala Phe Thr Ser His Gly Lys Lys Tyr Phe Gly Thr Ala Ser Asp Gln
        35                  40                  45

Ala Leu Leu Gln Lys Ser Gln Asn Glu Ala Ile Val Arg Lys Asp Phe
    50                  55                  60

Gly Gln Leu Thr Pro Glu Asn Ser Met Lys Trp Asp Ala Thr Glu Ala
65                  70                  75                  80

Ser Gln Gly Arg Phe Asn Phe Ala Gly Ala Asp Phe Leu Val Asn Tyr
                85                  90                  95

Ala Lys Gln Asn Gly Lys Lys Val Arg Gly His Thr Leu Trp His Ser
            100                 105                 110
```

```
Gln Leu Pro Ser Trp Val Ser Ala Ile Ser Asp Lys Asn Thr Leu Thr
            115                 120                 125
Ser Val Leu Lys Asn His Ile Thr Thr Val Met Thr Arg Tyr Lys Gly
        130                 135                 140
Gln Ile Tyr Ala Trp Asp Val Val Asn Glu Ile Phe Asn Glu Asp Gly
145                 150                 155                 160
Ser Leu Arg Asp Ser Val Phe Ser Arg Val Leu Gly Glu Asp Phe Val
                165                 170                 175
Arg Ile Ala Phe Glu Thr Ala Arg Ser Val Asp Pro Ser Ala Lys Leu
            180                 185                 190
Tyr Ile Asn Asp Tyr Lys Leu Asp Ser Ala Ser Tyr Gly Lys Thr Gln
        195                 200                 205
Gly Met Val Arg Tyr Val Lys Lys Trp Leu Ala Ala Gly Ile Pro Ile
    210                 215                 220
Asp Gly Ile Gly Gln Thr His Leu Gly Ala Gly Ala Ser Ser Ser Val
225                 230                 235                 240
Lys Gly Ala Leu Thr Ala Leu Ala Ser Ser Gly Val Ser Glu Val Ala
                245                 250                 255
Ile Thr Glu Leu Asp Ile Ala Gly Ala Ser Ser Gln Asp Tyr Val Asn
            260                 265                 270
Val Val Lys Ala Cys Leu Asp Val Pro Lys Cys Val Gly Ile Thr Val
        275                 280                 285
Trp Gly Val Ser Asp Arg Asp Ser Trp Arg Ser Gly Ser Ser Pro Leu
    290                 295                 300
Leu Phe Asp Ser Asn Tyr Gln Pro Lys Ala Ala Tyr Asn Ala Ile Ile
305                 310                 315                 320
Ala Ala Leu

<210> SEQ ID NO 13
<211> LENGTH: 1415
<212> TYPE: DNA
<213> ORGANISM: Aspergillus fumigatus

<400> SEQUENCE: 13
atggtccatc tatcttcatt ggcagcagcc ctggctgctc tgcctctgta tgtttaccca      60
ctcacgagag aggaacagc tttgacattg ctatagtgta tatggagctg cctgaacac      120 agcagccaaa gccaaaggac taaagtactt tggttccgcc acggacaatc cagagctcac      180
ggactctgcg tatgtcgcgc aactgagcaa caccgatgat tttggtcaaa tcacacccgg      240
aaactccatg aaggtttgct tacgtctgcc tccctggagc attgcctcaa aagctaattg      300
gttgttttgt ttggatagtg ggatgccacc gagccttctc agaattcttt ttcgttcgca      360
aatggagacg ccgtggtcaa tctggcgaac aagaatggcc agctgatgcg atgccatact      420
ctggtctggc acagtcagct accgaactgg ggtatgtaaa cgtcttgtct attctcaaat      480
actctctaac agttgacagt ctctagcggg tcatggacca atgcgaccct tttgcggcc      540 atgaagaatc atatcaccaa tgtggttact cactacaagg ggaagtgcta cgcctgggat      600
gttgtcaatg aaggtttgtt gctccatcta tcctcaatag ttcttttgaa actgacaagc      660
ctgtcaatct agccctgaac gaggacggta ctttccgtaa ctctgtcttc taccagatca      720
tcggcccagc atacattcct attgcgttcg ccacggctgc tgccgcagat cccgacgtga      780
aactctacta caacgactac aacattgaat actcaggcgc caaagcgact gctgcgcaga      840
atatcgtcaa gatgatcaag gcctacggcg cgaagatcga cggcgtcggc ctccaggcac      900
```

-continued

| | |
|---|---|
| actttatcgt cggcagcact ccgagtcaat cggatctgac gaccgtcttg aagggctaca | 960 |
| ctgctctcgg cgttgaggtg gcctataccg aacttgacat ccgcatgcag ctgcccctcga | 1020 |
| ccgccgcaaa gctggcccag cagtccactg acttccaagg cgtggccgca gcatgcgtta | 1080 |
| gcaccactgg ctgcgtgggt gtcactatct gggactggac cgacaagtac tcctgggtcc | 1140 |
| ccagcgtgtt ccaaggctac ggcgcccat tgccttggga tgagaactat gtgaagaagc | 1200 |
| cagcgtacga tggcctgatg gcgggtcttg gagcaagcgg ctccggcacc acaacgacca | 1260 |
| ctactactac ttctactacg acaggaggta cggaccctac tggagtcgct cagaaatggg | 1320 |
| gacagtgtgg cggtattggc tggaccgggc caacaacttg tgtcagtggt accacttgcc | 1380 |
| aaaagctgaa tgactggtac tcacagtgcc tgtaa | 1415 |

<210> SEQ ID NO 14
<211> LENGTH: 397
<212> TYPE: PRT
<213> ORGANISM: Aspergillus fumigatus

<400> SEQUENCE: 14

```
Met Val His Leu Ser Ser Leu Ala Ala Ala Leu Ala Ala Leu Pro Leu
1               5                   10                  15

Val Tyr Gly Ala Gly Leu Asn Thr Ala Ala Lys Ala Lys Gly Leu Lys
                20                  25                  30

Tyr Phe Gly Ser Ala Thr Asp Asn Pro Glu Leu Thr Asp Ser Ala Tyr
            35                  40                  45

Val Ala Gln Leu Ser Asn Thr Asp Asp Phe Gly Gln Ile Thr Pro Gly
        50                  55                  60

Asn Ser Met Lys Trp Asp Ala Thr Glu Pro Ser Gln Asn Ser Phe Ser
65                  70                  75                  80

Phe Ala Asn Gly Asp Ala Val Val Asn Leu Ala Asn Lys Asn Gly Gln
                85                  90                  95

Leu Met Arg Cys His Thr Leu Val Trp His Ser Gln Leu Pro Asn Trp
            100                 105                 110

Val Ser Ser Gly Ser Trp Thr Asn Ala Thr Leu Leu Ala Ala Met Lys
        115                 120                 125

Asn His Ile Thr Asn Val Val Thr His Tyr Lys Gly Lys Cys Tyr Ala
    130                 135                 140

Trp Asp Val Val Asn Glu Ala Leu Asn Glu Asp Gly Thr Phe Arg Asn
145                 150                 155                 160

Ser Val Phe Tyr Gln Ile Ile Gly Pro Ala Tyr Ile Pro Ile Ala Phe
                165                 170                 175

Ala Thr Ala Ala Ala Ala Asp Pro Asp Val Lys Leu Tyr Tyr Asn Asp
            180                 185                 190

Tyr Asn Ile Glu Tyr Ser Gly Ala Lys Ala Thr Ala Ala Gln Asn Ile
        195                 200                 205

Val Lys Met Ile Lys Ala Tyr Gly Ala Lys Ile Asp Gly Val Gly Leu
    210                 215                 220

Gln Ala His Phe Ile Val Gly Ser Thr Pro Ser Gln Ser Asp Leu Thr
225                 230                 235                 240

Thr Val Leu Lys Gly Tyr Thr Ala Leu Gly Val Glu Val Ala Tyr Thr
                245                 250                 255

Glu Leu Asp Ile Arg Met Gln Leu Pro Ser Thr Ala Ala Lys Leu Ala
            260                 265                 270

Gln Gln Ser Thr Asp Phe Gln Gly Val Ala Ala Ala Cys Val Ser Thr
        275                 280                 285
```

```
Thr Gly Cys Val Gly Val Thr Ile Trp Asp Trp Thr Asp Lys Tyr Ser
    290             295             300
Trp Val Pro Ser Val Phe Gln Gly Tyr Gly Ala Pro Leu Pro Trp Asp
305             310             315             320
Glu Asn Tyr Val Lys Lys Pro Ala Tyr Asp Gly Leu Met Ala Gly Leu
            325             330             335
Gly Ala Ser Gly Ser Gly Thr Thr Thr Thr Thr Thr Thr Ser Thr
        340             345             350
Thr Thr Gly Gly Thr Asp Pro Thr Gly Val Ala Gln Lys Trp Gly Gln
        355             360             365
Cys Gly Gly Ile Gly Trp Thr Gly Pro Thr Thr Cys Val Ser Gly Thr
    370             375             380
Thr Cys Gln Lys Leu Asn Asp Trp Tyr Ser Gln Cys Leu
385             390             395
```

<210> SEQ ID NO 15
<211> LENGTH: 2376
<212> TYPE: DNA
<213> ORGANISM: Aspergillus fumigatus

<400> SEQUENCE: 15

```
atggcggttg ccaaatctat tgctgccgtg ctggtagcac tgttgcctgg tgcgcttgct      60
caggcgaata caagctatgt tgattacaat gtggaggcga atccggatct caccccctcag   120
tcggtcgcta cgattgacct gtcctttccc gactgcgaga tggaccgct cagcaagact      180
ctcgtttgcg acacgtcggc tcggccgcat gaccgagctg ctgccctggt ttccatgttc    240
accttcgagg agctggtgaa caacacaggc aacactagcc ctggtgttcc aagacttggt    300
ctccctccgt accaagtatg gagcgaggct ctccatggac ttgaccgcgc caacttcaca    360
aacgagggag agtacagctg ggccacctcg ttccccatgc ctatcctgac aatgtcggcc    420
ttgaaccgaa ccctgatcaa ccagatcgcg accatcatcg caactcaagg acgagctttc    480
aataacgttg gcggtatggg ctggacgtg tacgccccga atataaatgc attcagatcg     540
gctatgtggg gaagaggtca agagaccccc ggagaagacg cttactgcct ggcatcggcg    600
tatgcgtacg agtatatcac tggcatccag ggtggtgttg atccggaaca cctcaagttg    660
gtggccactg ccaaacacta tgcgggctac gatcttgaga actgggacgg tcactcccgt    720
ttgggcaacg atatgaacat tacacagcag gaactttccg aatactacac ccctcagttc    780
cttgttgcag ccagagacgc caaagtgcac agtgtcatgt gctcctacaa cgcggtaaat    840
ggggtgccca gctgcgcaaa ctcgttcttc ctccagaccc tcctccgtga cacattcggc    900
ttcgtcgagg atggttatgt atccagcgac tgcgactcgg cgtacaatgt ctggaacccg    960
cacgagtttg cggccaacat cacggggggc gctgcagact ctatccgggc ggggacggac   1020
attgattgcg gcactactta tcaatactat ttcggcgaag cctttgacga gcaagaggtc   1080
accccgtgcag aaatcgaaag aggtgtgatc cgcctgtaca gcaacttggt gcgtctcggc   1140
tatttcgatg gcaatggaag cgtgtatcgg gacctgacgt ggaatgatgt cgtgaccacg   1200
gatgcctgga atatctcata cgaagccgct gtagaaggca ttgtcctact gaagaacgat   1260
ggaaccttgc ctctcgccaa gtcggtccgc agtgttgcat tgattgggcc ctggatgaat   1320
gtgacgactc agcttcaggg caactacttt ggaccggcgc cttatctgat tagtccgttg   1380
aatgccttcc agaattctga cttcgacgtg aactacgctt tcggcacgaa catttcatcc   1440
cactccacag atgggttttc cgaggcgttg tctgctgcga agaaatccga cgtcatcata   1500
```

```
ttcgcgggcg ggattgacaa cactttggaa gcagaagcca tggatcgcat gaatatcaca   1560
tggcccggca atcagctaca gctcatcgac cagttgagcc aactcggcaa accgctgatc   1620
gtcctccaga tgggcggcgg ccaagtcgac tcctcctcgc tcaagtccaa caagaatgtc   1680
aactccctga tctggggtgg ataccccgga caatccggcg gcaggctct  cctagacatc   1740 atcaccggca agcgcgcccc cgccggccga ctcgtggtca cgcagtaccc ggccgaatac   1800
gcaacccagt tccccgccac cgacatgagc ctgcggcctc acggcaataa tcccggccag   1860
acctacatgt ggtacaccgg caccccgtc  tacgagtttg ccacgggct  cttctacacg   1920 accttccacg cctccctccc tggcaccggc aaggacaaga cctccttcaa catccaagac   1980
ctcctcacgc agccgcatcc gggcttcgca acgtcgagc  aaatgccttt gctcaacttc   2040
accgtgacga tcaccaatac cggcaaggtc gcttccgact acactgctat gctcttcgcg   2100
aacaccaccg cgggacctgc tccatacccg aacaagtggc tcgtcggctt cgaccggctg   2160
gcgagcctgg aaccgcacag gtcgcagact atgaccatcc ccgtgactat cgacagcgtg   2220
gctcgtacgg atgaggccgg caatcgggtt ctctacccgg gaaagtacga gttggccctg   2280
aacaatgagc ggtcggttgt ccttcagttt gtgctgacag gccgagaggc tgtgattttc   2340
aagtggcctg tagagcagca gcagatttcg tctgcg                             2376
```

<210> SEQ ID NO 16
<211> LENGTH: 792
<212> TYPE: PRT
<213> ORGANISM: Aspergillus fumigatus

<400> SEQUENCE: 16

```
Met Ala Val Ala Lys Ser Ile Ala Ala Val Leu Val Ala Leu Leu Pro
1               5                   10                  15

Gly Ala Leu Ala Gln Ala Asn Thr Ser Tyr Val Asp Tyr Asn Val Glu
            20                  25                  30

Ala Asn Pro Asp Leu Thr Pro Gln Ser Val Ala Thr Ile Asp Leu Ser
        35                  40                  45

Phe Pro Asp Cys Glu Asn Gly Pro Leu Ser Lys Thr Leu Val Cys Asp
    50                  55                  60

Thr Ser Ala Arg Pro His Asp Arg Ala Ala Leu Val Ser Met Phe
65                  70                  75                  80

Thr Phe Glu Glu Leu Val Asn Asn Thr Gly Asn Thr Ser Pro Gly Val
                85                  90                  95

Pro Arg Leu Gly Leu Pro Pro Tyr Gln Val Trp Ser Glu Ala Leu His
            100                 105                 110

Gly Leu Asp Arg Ala Asn Phe Thr Asn Glu Gly Glu Tyr Ser Trp Ala
        115                 120                 125

Thr Ser Phe Pro Met Pro Ile Leu Thr Met Ser Ala Leu Asn Arg Thr
    130                 135                 140

Leu Ile Asn Gln Ile Ala Thr Ile Ala Thr Gln Gly Arg Ala Phe
145                 150                 155                 160

Asn Asn Val Gly Arg Tyr Gly Leu Asp Val Tyr Ala Pro Asn Ile Asn
                165                 170                 175

Ala Phe Arg Ser Ala Met Trp Gly Arg Gly Gln Glu Thr Pro Gly Glu
            180                 185                 190

Asp Ala Tyr Cys Leu Ala Ser Ala Tyr Ala Tyr Glu Tyr Ile Thr Gly
        195                 200                 205

Ile Gln Gly Gly Val Asp Pro Glu His Leu Lys Leu Val Ala Thr Ala
```

```
                210                 215                 220
Lys His Tyr Ala Gly Tyr Asp Leu Glu Asn Trp Asp Gly His Ser Arg
225                 230                 235                 240

Leu Gly Asn Asp Met Asn Ile Thr Gln Gln Glu Leu Ser Glu Tyr Tyr
                245                 250                 255

Thr Pro Gln Phe Leu Val Ala Ala Arg Asp Ala Lys Val His Ser Val
                260                 265                 270

Met Cys Ser Tyr Asn Ala Val Asn Gly Val Pro Ser Cys Ala Asn Ser
            275                 280                 285

Phe Phe Leu Gln Thr Leu Leu Arg Asp Thr Phe Gly Phe Val Glu Asp
        290                 295                 300

Gly Tyr Val Ser Ser Asp Cys Asp Ser Ala Tyr Asn Val Trp Asn Pro
305                 310                 315                 320

His Glu Phe Ala Ala Asn Ile Thr Gly Ala Ala Ala Asp Ser Ile Arg
                325                 330                 335

Ala Gly Thr Asp Ile Asp Cys Gly Thr Thr Tyr Gln Tyr Tyr Phe Gly
                340                 345                 350

Glu Ala Phe Asp Glu Gln Glu Val Thr Arg Ala Glu Ile Glu Arg Gly
            355                 360                 365

Val Ile Arg Leu Tyr Ser Asn Leu Val Arg Leu Gly Tyr Phe Asp Gly
        370                 375                 380

Asn Gly Ser Val Tyr Arg Asp Leu Thr Trp Asn Asp Val Val Thr Thr
385                 390                 395                 400

Asp Ala Trp Asn Ile Ser Tyr Glu Ala Ala Val Glu Gly Ile Val Leu
                405                 410                 415

Leu Lys Asn Asp Gly Thr Leu Pro Leu Ala Lys Ser Val Arg Ser Val
                420                 425                 430

Ala Leu Ile Gly Pro Trp Met Asn Val Thr Thr Gln Leu Gln Gly Asn
            435                 440                 445

Tyr Phe Gly Pro Ala Pro Tyr Leu Ile Ser Pro Leu Asn Ala Phe Gln
        450                 455                 460

Asn Ser Asp Phe Asp Val Asn Tyr Ala Phe Gly Thr Asn Ile Ser Ser
465                 470                 475                 480

His Ser Thr Asp Gly Phe Ser Glu Ala Leu Ser Ala Ala Lys Lys Ser
                485                 490                 495

Asp Val Ile Ile Phe Ala Gly Gly Ile Asp Asn Thr Leu Glu Ala Glu
                500                 505                 510

Ala Met Asp Arg Met Asn Ile Thr Trp Pro Gly Asn Gln Leu Gln Leu
            515                 520                 525

Ile Asp Gln Leu Ser Gln Leu Gly Lys Pro Leu Ile Val Leu Gln Met
        530                 535                 540

Gly Gly Gly Gln Val Asp Ser Ser Ser Leu Lys Ser Asn Lys Asn Val
545                 550                 555                 560

Asn Ser Leu Ile Trp Gly Gly Tyr Pro Gly Gln Ser Gly Gly Gln Ala
                565                 570                 575

Leu Leu Asp Ile Ile Thr Gly Lys Arg Ala Pro Ala Gly Arg Leu Val
                580                 585                 590

Val Thr Gln Tyr Pro Ala Glu Tyr Ala Thr Gln Phe Pro Ala Thr Asp
            595                 600                 605

Met Ser Leu Arg Pro His Gly Asn Asn Pro Gly Gln Thr Tyr Met Trp
        610                 615                 620

Tyr Thr Gly Thr Pro Val Tyr Glu Phe Gly His Gly Leu Phe Tyr Thr
625                 630                 635                 640
```

```
Thr Phe His Ala Ser Leu Pro Gly Thr Gly Lys Asp Lys Thr Ser Phe
                645                 650                 655
Asn Ile Gln Asp Leu Leu Thr Gln Pro His Pro Gly Phe Ala Asn Val
            660                 665                 670
Glu Gln Met Pro Leu Leu Asn Phe Thr Val Thr Ile Thr Asn Thr Gly
        675                 680                 685
Lys Val Ala Ser Asp Tyr Thr Ala Met Leu Phe Ala Asn Thr Thr Ala
    690                 695                 700
Gly Pro Ala Pro Tyr Pro Asn Lys Trp Leu Val Gly Phe Asp Arg Leu
705                 710                 715                 720
Ala Ser Leu Glu Pro His Arg Ser Gln Thr Met Thr Ile Pro Val Thr
                725                 730                 735
Ile Asp Ser Val Ala Arg Thr Asp Glu Ala Gly Asn Arg Val Leu Tyr
            740                 745                 750
Pro Gly Lys Tyr Glu Leu Ala Leu Asn Asn Glu Arg Ser Val Val Leu
        755                 760                 765
Gln Phe Val Leu Thr Gly Arg Glu Ala Val Ile Phe Lys Trp Pro Val
    770                 775                 780
Glu Gln Gln Gln Ile Ser Ser Ala
785                 790

<210> SEQ ID NO 17
<211> LENGTH: 1545
<212> TYPE: DNA
<213> ORGANISM: Trichoderma reesei

<400> SEQUENCE: 17
atgtatcgga agttggccgt catctcggcc ttcttggcca cagctcgtgc tcagtcggcc     60
tgcactctcc aatcggagac tcacccgcct ctgacatggc agaaatgctc gtctggtggc    120
acgtgcactc aacagacagg ctccgtggtc atcgacgcca actggcgctg gactcacgct    180
acgaacagca gcacgaactg ctacgatggc aacacttgga gctcgaccct atgtcctgac    240
aacgagacct cgcgcaagaa ctgctgtctg acggtgccg cctacgcgtc cacgtacgga    300
gttaccacga gcggtaacag cctctccatt ggctttgtca cccagtctgc gcagaagaac    360
gttggcgctc gcctttacct tatggcgagc gacacgacct accaggaatt caccctgctt    420
ggcaacgagt tctctttcga tgttgatgtt tcgcagctgc cgtgcggctt gaacggagct    480
ctctacttcg tgtccatgga cgcggatggt ggcgtgagca agtatcccac caacaccgct    540
ggcgccaagt acggcacggg gtactgtgac agccagtgtc ccgcgatct gaagttcatc    600 aatggccagg ccaacgttga gggctggag ccgtcatcca acaacgcgaa cacgggcatt    660
ggaggacacg gaagctgctg ctctgagatg gatatctggg aggccaactc catctccgag    720
gctcttaccc ccacccttg cacgactgtc ggccaggaga tctgcgaggg tgatgggtgc    780
ggcggaactt actccgataa cagatatggc ggcacttgcg atcccgatgg ctgcgactgg    840
aacccatacc gcctgggcaa caccagcttc tacggccctg gctcaagctt taccctcgat    900
accaccaaga aattgaccgt tgtcacccag ttcgagacgt cgggtgccat caaccgatac    960
tatgtccaga atgcgtcac tttccagcag cccaacgccg agcttggtag ttactctggc   1020
aacgagctca cgatgatta ctgcacagct gaggaggcag aattcggcgg atcctctttc   1080
tcagacaagg gcggcctgac tcagttcaag aaggctacct ctggcggcat ggttctggtc   1140
atgagtctgt gggatgatta ctacgccaac atgctgtggc tggactccac ctacccgaca   1200
```

-continued

```
aacgagacct cctccacacc cggtgccgtg cgcggaagct gctccaccag ctccggtgtc    1260
cctgctcagg tcgaatctca gtctcccaac gccaaggtca ccttctccaa catcaagttc    1320
ggacccattg gcagcaccgg caaccctagc ggcggcaacc ctcccggcgg aaacccgcct    1380
ggcaccacca ccaccgccg cccagccact accactggaa gctctcccgg acctacccag    1440
tctcactacg gccagtgcgg cggtattggc tacagcggcc ccacggtctg cgccagcggc    1500
acaacttgcc aggtcctgaa cccttactac tctcagtgcc tgtaa                    1545
```

<210> SEQ ID NO 18
<211> LENGTH: 514
<212> TYPE: PRT
<213> ORGANISM: Trichoderma reesei

<400> SEQUENCE: 18

```
Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320
```

```
Tyr Val Gln Asn Gly Val Thr Phe Gln Gln Pro Asn Ala Glu Leu Gly
            325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
            355                 360                 365

Phe Lys Lys Ala Thr Ser Gly Gly Met Val Leu Val Met Ser Leu Trp
370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
            405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
            435                 440                 445

Pro Ser Gly Gly Asn Pro Pro Gly Gly Asn Pro Pro Gly Thr Thr Thr
            450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
            485                 490                 495

Cys Ala Ser Gly Thr Thr Cys Gln Val Leu Asn Pro Tyr Tyr Ser Gln
            500                 505                 510

Cys Leu

<210> SEQ ID NO 19
<211> LENGTH: 1611
<212> TYPE: DNA
<213> ORGANISM: Trichoderma reesei

<400> SEQUENCE: 19
atgattgtcg gcattctcac cacgctggct acgctggcca cactcgcagc tagtgtgcct      60
ctagaggagc ggcaagcttg ctcaagcgtc tggtaattat gtgaaccctc tcaagagacc     120
caaatactga gatatgtcaa ggggccaatg tggtggccag aattggtcgg gtccgacttg     180
ctgtgcttcc ggaagcacat gcgtctactc caacgactat tactcccagt gtcttcccgg     240
cgctgcaagc tcaagctcgt ccacgcgcgc cgcgtcgacg acttctcgag tatcccccac     300
aacatcccgg tcgagctccg cgacgcctcc acctggttct actactacca gagtaccctc     360
agtcggatcg ggaaccgcta cgtattcagg caaccctttt gttggggtca ctccttgggc     420
caatgcatat tacgcctctg aagttagcag cctcgctatt cctagcttga ctggagccat     480
ggccactgct gcagcagctg tcgcaaaggt tccctctttt atgtggctgt aggtcctccc     540
ggaaccaagg caatctgtta ctgaaggctc atcattcact gcagagatac tcttgacaag     600
acccctctca tggagcaaac cttggccgac atccgcaccg ccaacaagaa tggcggtaac     660
tatgccggac agtttgtggt gtatgacttg ccggatcgcg attgcgctgc ccttgcctcg     720
aatggcgaat actctattgc cgatggtggc gtcgccaaat ataagaacta tatcgacacc     780
attcgtcaaa ttgtcgtgga atattccgat atccggaccc tcctggttat tggtatgagt     840
ttaaacacct gcctcccccc cccttccct tcctttcccg ccggcatctt gtcgttgtgc     900
taactattgt tccctcttcc agagcctgac tctcttgcca acctggtgac caacctcggt     960
```

-continued

```
actccaaagt gtgccaatgc tcagtcagcc taccttgagt gcatcaacta cgccgtcaca    1020
cagctgaacc ttccaaatgt tgcgatgtat ttggacgctg ccatgcagg atggcttggc     1080 tggccggcaa accaagaccc ggccgctcag ctatttgcaa atgtttacaa gaatgcatcg    1140
tctccgagag ctcttcgcgg attggcaacc aatgtcgcca actacaacgg tggaacatt     1200 accagccccc catcgtacac gcaaggcaac gctgtctaca cgagaagct gtacatccac     1260 gctattggac gtcttcttgc caatcacggc tggtccaacg ccttcttcat cactgatcaa    1320
ggtcgatcgg gaaagcagcc taccggacag caacagtggg gagactggtg caatgtgatc    1380
ggcaccggat ttggtattcg cccatccgca aacactgggg actcgttgct ggattcgttt    1440
gtctgggtca agccaggcgg cgagtgtgac ggcaccagcg acagcagtgc gccacgattt    1500
gactcccact gtgcgctccc agatgccttg caaccggcgc ctcaagctgg tgcttggttc    1560
caagcctact ttgtgcagct ctcacaaac gcaaacccat cgttcctgta a              1611
```

<210> SEQ ID NO 20
<211> LENGTH: 471
<212> TYPE: PRT
<213> ORGANISM: Trichoderma reesei

<400> SEQUENCE: 20

```
Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
                20                  25                  30

Gln Cys Gly Gly Gln Asn Trp Ser Gly Pro Thr Cys Cys Ala Ser Gly
            35                  40                  45

Ser Thr Cys Val Tyr Ser Asn Asp Tyr Tyr Ser Gln Cys Leu Pro Gly
        50                  55                  60

Ala Ala Ser Ser Ser Ser Thr Arg Ala Ala Ser Thr Thr Ser Arg
65                  70                  75                  80

Val Ser Pro Thr Thr Ser Arg Ser Ser Ala Thr Pro Pro Gly
                85                  90                  95

Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
        115                 120                 125

Ala Ser Glu Val Ser Ser Leu Ala Ile Pro Ser Leu Thr Gly Ala Met
    130                 135                 140

Ala Thr Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
```

```
            260                 265                 270
Ala Val Thr Gln Leu Asn Leu Pro Asn Val Ala Met Tyr Leu Asp Ala
            275                 280                 285
Gly His Ala Gly Trp Leu Gly Trp Pro Ala Asn Gln Asp Pro Ala Ala
            290                 295                 300
Gln Leu Phe Ala Asn Val Tyr Lys Asn Ala Ser Ser Pro Arg Ala Leu
305                 310                 315                 320
Arg Gly Leu Ala Thr Asn Val Ala Asn Tyr Asn Gly Trp Asn Ile Thr
                325                 330                 335
Ser Pro Pro Ser Tyr Thr Gln Gly Asn Ala Val Tyr Asn Glu Lys Leu
                340                 345                 350
Tyr Ile His Ala Ile Gly Arg Leu Leu Ala Asn His Gly Trp Ser Asn
                355                 360                 365
Ala Phe Phe Ile Thr Asp Gln Gly Arg Ser Gly Lys Gln Pro Thr Gly
            370                 375                 380
Gln Gln Gln Trp Gly Asp Trp Cys Asn Val Ile Gly Thr Gly Phe Gly
385                 390                 395                 400
Ile Arg Pro Ser Ala Asn Thr Gly Asp Ser Leu Leu Asp Ser Phe Val
                405                 410                 415
Trp Val Lys Pro Gly Gly Glu Cys Asp Gly Thr Ser Asp Ser Ser Ala
                420                 425                 430
Pro Arg Phe Asp Ser His Cys Ala Leu Pro Asp Ala Leu Gln Pro Ala
                435                 440                 445
Pro Gln Ala Gly Ala Trp Phe Gln Ala Tyr Phe Val Gln Leu Leu Thr
            450                 455                 460
Asn Ala Asn Pro Ser Phe Leu
465                 470

<210> SEQ ID NO 21
<211> LENGTH: 2615
<212> TYPE: DNA
<213> ORGANISM: Trichoderma reesei

<400> SEQUENCE: 21
atgggatttg gccgcaatgc tgccgagccc gagtgtttct gcaacgttat ccaggagatt     60
tgcgcttgcc aagagggag ttgacgggga gagtcccaac tggttccttc agtaacgcca    120
ccctggcaga ctatataact gtggacaag actctgcttt gttgagttct tcctaccagt    180
cttgaccaag accattctgt tgagcccaat cagaaatgcg ttaccgaaca gcagctgcgc    240
tggcacttgc cactgggccc tttgctaggg cagacagtca gtatagctgg tccatactgg    300
gatgtatatg tatcctggag acaccatgct gactcttgaa tcaaggtagc tcaacatcgg    360
gggcctcggc tgaggcagtt gtacctcctg cagggactcc atgggaacc gcgtacgaca    420 aggcgaaggc cgcattggca aagctcaatc tccaagataa ggtcggcatc gtgagcggtg    480
tcggctggaa cggcggtcct tgcgttggaa acacatctcc ggcctccaag atcagctatc    540
catcgctatg ccttcaagac ggacccctcg gtgttcgata ctcgacaggc agcacagcct    600
ttacgccggg cgttcaagcg gcctcgacgt gggatgtcaa tttgatccgc gaacgtggac    660
agttcatcgg tgaggaggtg aaggcctcgg ggattcatgt catacttggt cctgtggctg    720
ggccgctggg aaagactccg cagggcggtc gcaactggga gggcttcggt gtcgatccat    780
atctcacggg cattgccatg ggtcaaacca tcaacggcat ccagtcggta ggcgtgcagg    840
cgacagcgaa gcactatatc ctcaacgagc aggagctcaa tcgagaaacc atttcgagca    900
```

-continued

```
acccagatga ccgaactctc catgagctgt atacttggcc atttgccgac gcggttcagg    960
ccaatgtcgc ttctgtcatg tgctcgtaca caaggtcaa taccacctgg gcctgcgagg   1020
atcagtacac gctgcagact gtgctgaaag accagctggg gttcccaggc tatgtcatga   1080
cggactggaa cgcacagcac acgactgtcc aaagcgcgaa ttctgggctt gacatgtcaa   1140
tgcctggcac agacttcaac ggtaacaatc ggctctgggg tccagctctc accaatgcgg   1200
taaatagcaa tcaggtcccc acgagcgag tcgacgatat ggtgactcgt atcctcgccg   1260
catggtactt gacaggccag gaccaggcag gctatccgtc gttcaacatc agcagaaatg   1320
ttcaaggaaa ccacaagacc aatgtcaggg caattgccag ggacggcatc gttctgctca   1380
agaatgacgc caacatcctg ccgctcaaga agcccgctag cattgccgtc gttggatctg   1440
ccgcaatcat tggtaaccac gccagaaact cgccctcgtg caacgacaaa ggctgcgacg   1500
acggggcctt gggcatgggt tggggttccg cgccgtcaa ctatccgtac ttcgtcgcgc   1560
cctacgatgc catcaatacc agagcgtctt cgcagggcac ccaggttacc ttgagcaaca   1620
ccgacaacac gtcctcaggc gcatctgcag caagaggaaa ggacgtcgcc atcgtcttca   1680
tcaccgccga ctcgggtgaa ggctacatca ccgtggaggg caacgcgggc gatcgcaaca   1740
acctggatcc gtggcacaac ggcaatgccc tggtccaggc ggtggccggt gccaacagca   1800
acgtcattgt tgttgtccac tccgttggcg ccatcattct ggagcagatt cttgctcttc   1860
cgcaggtcaa ggccgttgtc tgggcgggtc ttccttctca ggagagcggc aatgcgctcg   1920
tcgacgtgct gtggggagat gtcagcccct ctggcaagct ggtgtacacc attgcgaaga   1980
gccccaatga ctataacact cgcatcgttt ccggcggcag tgacagcttc agcgagggac   2040
tgttcatcga ctataagcac ttcgacgacg ccaatatcac gccgcggtac gagttcggct   2100
atggactgtg taagtttgct aacctgaaca atctcattaga caggttgact gacggatgac   2160
tgtggaatga tagcttacac caagttcaac tactcacgcc tctccgtctt gtcgaccgcc   2220
aagtctggtc ctgcgactgg ggccgttgtg ccggaggcc cgagtgatct gttccagaat   2280
gtcgcgacag tcaccgttga catcgcaaac tctggccaag tgactggtgc cgaggtagcc   2340
cagctgtaca tcacctaccc atcttcagca cccaggaccc ctccgaagca gctgcgaggc   2400
tttgccaagc tgaacctcac gcctggtcag agcggaacag caacgttcaa catccgacga   2460
cgagatctca gctactggga cacggcttcg cagaaatggg tggtgccgtc ggggtcgttt   2520
ggcatcagcg tgggagcgag cagccgggat atcaggctga cgagcactct gtcggtagcg   2580
tagcgcgagg agggtgaagg cggttgacct gtgac                             2615
```

<210> SEQ ID NO 22
<211> LENGTH: 744
<212> TYPE: PRT
<213> ORGANISM: Trichoderma reesei

<400> SEQUENCE: 22

Met Arg Tyr Arg Thr Ala Ala Ala Leu Ala Leu Ala Thr Gly Pro Phe
1               5                   10                  15

Ala Arg Ala Asp Ser His Ser Thr Ser Gly Ala Ser Ala Glu Ala Val
            20                  25                  30

Val Pro Pro Ala Gly Thr Pro Trp Gly Thr Ala Tyr Asp Lys Ala Lys
        35                  40                  45

Ala Ala Leu Ala Lys Leu Asn Leu Gln Asp Lys Val Gly Ile Val Ser
    50                  55                  60

Gly Val Gly Trp Asn Gly Gly Pro Cys Val Gly Asn Thr Ser Pro Ala

-continued

```
                65                  70                  75                  80
        Ser Lys Ile Ser Tyr Pro Ser Leu Cys Leu Gln Asp Gly Pro Leu Gly
                            85                  90                  95

Val Arg Tyr Ser Thr Gly Ser Thr Ala Phe Thr Pro Gly Val Gln Ala
                            100                 105                 110

Ala Ser Thr Trp Asp Val Asn Leu Ile Arg Glu Arg Gly Gln Phe Ile
                            115                 120                 125

Gly Glu Glu Val Lys Ala Ser Gly Ile His Val Ile Leu Gly Pro Val
                    130                 135                 140

Ala Gly Pro Leu Gly Lys Thr Pro Gln Gly Gly Arg Asn Trp Glu Gly
        145                 150                 155                 160

Phe Gly Val Asp Pro Tyr Leu Thr Gly Ile Ala Met Gly Gln Thr Ile
                            165                 170                 175

Asn Gly Ile Gln Ser Val Gly Val Gln Ala Thr Ala Lys His Tyr Ile
                        180                 185                 190

Leu Asn Glu Gln Glu Leu Asn Arg Glu Thr Ile Ser Ser Asn Pro Asp
                        195                 200                 205

Asp Arg Thr Leu His Glu Leu Tyr Thr Trp Pro Phe Ala Asp Ala Val
                    210                 215                 220

Gln Ala Asn Val Ala Ser Val Met Cys Ser Tyr Asn Lys Val Asn Thr
        225                 230                 235                 240

Thr Trp Ala Cys Glu Asp Gln Tyr Thr Leu Gln Thr Val Leu Lys Asp
                            245                 250                 255

Gln Leu Gly Phe Pro Gly Tyr Val Met Thr Asp Trp Asn Ala Gln His
                            260                 265                 270

Thr Thr Val Gln Ser Ala Asn Ser Gly Leu Asp Met Ser Met Pro Gly
                    275                 280                 285

Thr Asp Phe Asn Gly Asn Asn Arg Leu Trp Gly Pro Ala Leu Thr Asn
                    290                 295                 300

Ala Val Asn Ser Asn Gln Val Pro Thr Ser Arg Val Asp Asp Met Val
        305                 310                 315                 320

Thr Arg Ile Leu Ala Ala Trp Tyr Leu Thr Gly Gln Asp Gln Ala Gly
                            325                 330                 335

Tyr Pro Ser Phe Asn Ile Ser Arg Asn Val Gln Gly Asn His Lys Thr
                            340                 345                 350

Asn Val Arg Ala Ile Ala Arg Asp Gly Ile Val Leu Leu Lys Asn Asp
                    355                 360                 365

Ala Asn Ile Leu Pro Leu Lys Lys Pro Ala Ser Ile Ala Val Val Gly
        370                 375                 380

Ser Ala Ala Ile Ile Gly Asn His Ala Arg Asn Ser Pro Ser Cys Asn
        385                 390                 395                 400

Asp Lys Gly Cys Asp Asp Gly Ala Leu Gly Met Gly Trp Gly Ser Gly
                            405                 410                 415

Ala Val Asn Tyr Pro Tyr Phe Val Ala Pro Tyr Asp Ala Ile Asn Thr
                            420                 425                 430

Arg Ala Ser Ser Gln Gly Thr Gln Val Thr Leu Ser Asn Thr Asp Asn
                    435                 440                 445

Thr Ser Ser Gly Ala Ser Ala Arg Gly Lys Asp Val Ala Ile Val
        450                 455                 460

Phe Ile Thr Ala Asp Ser Gly Glu Gly Tyr Ile Thr Val Glu Gly Asn
        465                 470                 475                 480

Ala Gly Asp Arg Asn Asn Leu Asp Pro Trp His Asn Gly Asn Ala Leu
                            485                 490                 495
```

Val Gln Ala Val Ala Gly Ala Asn Ser Asn Val Ile Val Val His
            500                 505                 510
Ser Val Gly Ala Ile Ile Leu Glu Gln Ile Leu Ala Leu Pro Gln Val
            515                 520                 525
Lys Ala Val Val Trp Ala Gly Leu Pro Ser Gln Glu Ser Gly Asn Ala
        530                 535                 540
Leu Val Asp Val Leu Trp Gly Asp Val Ser Pro Ser Gly Lys Leu Val
545                 550                 555                 560
Tyr Thr Ile Ala Lys Ser Pro Asn Asp Tyr Asn Thr Arg Ile Val Ser
                565                 570                 575
Gly Gly Ser Asp Ser Phe Ser Glu Gly Leu Phe Ile Asp Tyr Lys His
            580                 585                 590
Phe Asp Asp Ala Asn Ile Thr Pro Arg Tyr Glu Phe Gly Tyr Gly Leu
        595                 600                 605
Ser Tyr Thr Lys Phe Asn Tyr Ser Arg Leu Ser Val Leu Ser Thr Ala
    610                 615                 620
Lys Ser Gly Pro Ala Thr Gly Ala Val Val Pro Gly Gly Pro Ser Asp
625                 630                 635                 640
Leu Phe Gln Asn Val Ala Thr Val Thr Val Asp Ile Ala Asn Ser Gly
                645                 650                 655
Gln Val Thr Gly Ala Glu Val Ala Gln Leu Tyr Ile Thr Tyr Pro Ser
            660                 665                 670
Ser Ala Pro Arg Thr Pro Pro Lys Gln Leu Arg Gly Phe Ala Lys Leu
        675                 680                 685
Asn Leu Thr Pro Gly Gln Ser Gly Thr Ala Thr Phe Asn Ile Arg Arg
    690                 695                 700
Arg Asp Leu Ser Tyr Trp Asp Thr Ala Ser Gln Lys Trp Val Val Pro
705                 710                 715                 720
Ser Gly Ser Phe Gly Ile Ser Val Gly Ala Ser Ser Arg Asp Ile Arg
                725                 730                 735
Leu Thr Ser Thr Leu Ser Val Ala
            740

<210> SEQ ID NO 23
<211> LENGTH: 752
<212> TYPE: DNA
<213> ORGANISM: Trichoderma reesei

<400> SEQUENCE: 23

```
atggttgcct tttccagcct catctgcgct ctcaccagca tcgccagtac tctggcgatg      60
cccacaggcc tcgagcctga gagcagtgtc aacgtcacag agcgtggcat gtacgacttt     120
gttcttggag ctcacaatga tcatcgccgt cgtgctagca tcaactacga ccaaaactac     180
caaactggcg acaagtcag ctattcgcct tccaacactg gcttctcagt gaactggaac     240
actcaagatg actttgttgt gggcgttggt tggacgactg atcttctgc gtaggaggac     300
tcctcatcat tctgcacttt gaaagcatct tctgaccaaa gcttctctt agtcccatca     360
actttggcgg ctcttttagt gtcaacagcg gaactggcct gctttccgtc tatggctgga     420
gcaccaaccc actggttgag tactacatca tggaggacaa ccacaactac ccagcacagg     480
gtaccgtcaa gggaaccgtc accagcgacg agccacttac accatctgg gagaatacccc     540
gtgtcaacga gccttccatc agggcacag cgaccttcaa ccagtacatt tccgtgcgga     600
actcgcccag gaccagcgga actgttactg tgcagaacca cttcaatgct tgggcctcgc     660
```

```
ttggcctgca ccttgggcag atgaactacc aggttgtcgc tgtcgaaggc tggggtggta    720
gtggttctgc ctcacagagt gtcagcaact ag                                  752
```

<210> SEQ ID NO 24
<211> LENGTH: 229
<212> TYPE: PRT
<213> ORGANISM: Trichoderma reesei

<400> SEQUENCE: 24

```
Met Val Ala Phe Ser Ser Leu Ile Cys Ala Leu Thr Ser Ile Ala Ser
1               5                   10                  15

Thr Leu Ala Met Pro Thr Gly Leu Glu Pro Glu Ser Ser Val Asn Val
            20                  25                  30

Thr Glu Arg Gly Met Tyr Asp Phe Val Leu Gly Ala His Asn Asp His
        35                  40                  45

Arg Arg Arg Ala Ser Ile Asn Tyr Asp Gln Asn Tyr Gln Thr Gly Gly
    50                  55                  60

Gln Val Ser Tyr Ser Pro Ser Asn Thr Gly Phe Ser Val Asn Trp Asn
65                  70                  75                  80

Thr Gln Asp Asp Phe Val Val Gly Val Gly Trp Thr Thr Gly Ser Ser
                85                  90                  95

Ala Pro Ile Asn Phe Gly Gly Ser Phe Ser Val Asn Ser Gly Thr Gly
            100                 105                 110

Leu Leu Ser Val Tyr Gly Trp Ser Thr Asn Pro Leu Val Glu Tyr Tyr
        115                 120                 125

Ile Met Glu Asp Asn His Asn Tyr Pro Ala Gln Gly Thr Val Lys Gly
    130                 135                 140

Thr Val Thr Ser Asp Gly Ala Thr Tyr Thr Ile Trp Glu Asn Thr Arg
145                 150                 155                 160

Val Asn Glu Pro Ser Ile Gln Gly Thr Ala Thr Phe Asn Gln Tyr Ile
                165                 170                 175

Ser Val Arg Asn Ser Pro Arg Thr Ser Gly Thr Val Thr Val Gln Asn
            180                 185                 190

His Phe Asn Ala Trp Ala Ser Leu Gly Leu His Leu Gly Gln Met Asn
        195                 200                 205

Tyr Gln Val Val Ala Val Glu Gly Trp Gly Gly Ser Gly Ser Ala Ser
    210                 215                 220

Gln Ser Val Ser Asn
225
```

<210> SEQ ID NO 25
<211> LENGTH: 796
<212> TYPE: DNA
<213> ORGANISM: Trichoderma reesei

<400> SEQUENCE: 25

```
caagaagaca tcaacatggt ctccttcacc tccctcctcg ccggcgtcgc cgccatctcg    60
ggcgtcttgg ccgctcccgc cgccgaggtc gaatccgtgg ctgtggagaa gcgccagacg    120
attcagcccg gcacgggcta caacaacggc tacttctact cgtactggaa cgatggccac    180
ggcggcgtga cgtacaccaa tggtcccggc gggcagttct ccgtcaactg gtccaactcg    240
ggcaactttg tcggcggcaa gggatggcag cccggcacca agaacaagta agactaccta    300
ctcttacccc ctttgaccaa cacagcacaa cacaatacaa cacatgtgac taccaatcat    360
ggaatcggat ctaacagctg tgttttcaaa aaaaagggtc atcaacttct cgggcagcta    420
```

```
caaccccaac ggcaacagct acctctccgt gtacggctgg tcccgcaacc ccctgatcga    480
gtactacatc gtcgagaact ttggcaccta caacccgtcc acgggcgcca ccaagctggg    540
cgaggtcacc tccgacggca gcgtctacga catttaccgc acgcagcgcg tcaaccagcc    600
gtccatcatc ggcaccgcca ccttttacca gtactggtcc gtccgccgca accaccgctc    660
gagcggctcc gtcaacacgg cgaaccactt caacgcgtgg gctcagcaag gcctgacgct    720
cgggacgatg gattaccaga ttgttgccgt ggagggttac tttagctctg gctctgcttc    780
catcaccgtc agctaa                                                   796
```

<210> SEQ ID NO 26
<211> LENGTH: 223
<212> TYPE: PRT
<213> ORGANISM: Trichoderma reesei
<400> SEQUENCE: 26

```
Met Val Ser Phe Thr Ser Leu Leu Ala Gly Val Ala Ala Ile Ser Gly
1               5                   10                  15

Val Leu Ala Ala Pro Ala Ala Glu Val Glu Ser Val Ala Val Glu Lys
            20                  25                  30

Arg Gln Thr Ile Gln Pro Gly Thr Gly Tyr Asn Asn Gly Tyr Phe Tyr
        35                  40                  45

Ser Tyr Trp Asn Asp Gly His Gly Val Thr Tyr Thr Asn Gly Pro
    50                  55                  60

Gly Gly Gln Phe Ser Val Asn Trp Ser Asn Ser Gly Asn Phe Val Gly
65                  70                  75                  80

Gly Lys Gly Trp Gln Pro Gly Thr Lys Asn Lys Val Ile Asn Phe Ser
                85                  90                  95

Gly Ser Tyr Asn Pro Asn Gly Asn Ser Tyr Leu Ser Val Tyr Gly Trp
            100                 105                 110

Ser Arg Asn Pro Leu Ile Glu Tyr Tyr Ile Val Glu Asn Phe Gly Thr
        115                 120                 125

Tyr Asn Pro Ser Thr Gly Ala Thr Lys Leu Gly Glu Val Thr Ser Asp
    130                 135                 140

Gly Ser Val Tyr Asp Ile Tyr Arg Thr Gln Arg Val Asn Gln Pro Ser
145                 150                 155                 160

Ile Ile Gly Thr Ala Thr Phe Tyr Gln Tyr Trp Ser Val Arg Arg Asn
                165                 170                 175

His Arg Ser Ser Gly Ser Val Asn Thr Ala Asn His Phe Asn Ala Trp
            180                 185                 190

Ala Gln Gln Gly Leu Thr Leu Gly Thr Met Asp Tyr Gln Ile Val Ala
        195                 200                 205

Val Glu Gly Tyr Phe Ser Ser Gly Ser Ala Ser Ile Thr Val Ser
    210                 215                 220
```

<210> SEQ ID NO 27
<211> LENGTH: 1352
<212> TYPE: DNA
<213> ORGANISM: Trichoderma reesei
<400> SEQUENCE: 27

```
atgaaagcaa acgtcatctt gtgcctcctg gccccctgg tcgccgctct ccccaccgaa    60
accatccacc tcgaccccga gctcgccgct ctccgcgcca acctcaccga gcgaacagcc    120
gacctctggg accgccaagc tctctcaaagc atcgaccagc tcatcaagag aaaaggcaag    180
ctctactttg gcaccgccac cgaccgcggc ctcctccaac gggaaaagaa cgcggccatc    240
```

-continued

```
atccaggcag acctcggcca ggtgacgccg gagaacagca tgaagtggca gtcgctcgag    300
aacaaccaag gccagctgaa ctggggagac gccgactatc tcgtcaactt tgcccagcaa    360
aacggcaagt cgatacgcgg ccacactctg atctggcact cgcagctgcc tgcgtgggtg    420
aacaatatca caacgcgga tactctgcgg caagtcatcc gcacccatgt ctctactgtg    480
gttgggcggt acaagggcaa gattcgtgct tgggtgagtt tgaacacca catgcccctt    540 ttcttagtcc gctcctcctc ctcttggaac ttctcacagt tatagccgta tacaacattc    600
gacaggaaat ttaggatgac aactactgac tgacttgtgt gtgtgatggc gataggacgt    660
ggtcaatgaa atcttcaacg aggatggaac gctgcgctct tcagtctttt ccaggctcct    720
cggcgaggag tttgtctcga ttgcctttcg tgctgctcga gatgctgacc cttctgcccg    780
tctttacatc aacgactaca atctcgaccg cgccaactat ggcaaggtca acgggttgaa    840
gacttacgtc tccaagtgga tctctcaagg agttcccatt gacggtattg gtgagccacg    900
acccctaaat gtcccccatt agagtctctt tctagagcca aggcttgaag ccattcaggg    960
actgacacga gagccttctc tacaggaagc cagtcccatc tcagcggcgg cggaggctct   1020
ggtacgctgg gtgcgctcca gcagctggca acggtacccg tcaccgagct ggccattacc   1080
gagctggaca ttcaggggc accgacgacg gattacaccc aagttgttca gcatgcctg    1140 agcgtctcca gtgcgtcgg catcaccgtg tggggcatca gtgacaaggt aagttgcttc   1200
ccctgtctgt gcttatcaac tgtaagcagc aacaactgat gctgtctgtc tttacctagg   1260
actcgtggcg tgccagcacc aaccctcttc tgtttgacgc aaacttcaac cccaagccgg   1320
catataacag cattgttggc atcttacaat ag                                 1352
```

<210> SEQ ID NO 28
<211> LENGTH: 347
<212> TYPE: PRT
<213> ORGANISM: Trichoderma reesei

<400> SEQUENCE: 28

```
Met Lys Ala Asn Val Ile Leu Cys Leu Leu Ala Pro Leu Val Ala Ala
1               5                   10                  15

Leu Pro Thr Glu Thr Ile His Leu Asp Pro Glu Leu Ala Ala Leu Arg
            20                  25                  30

Ala Asn Leu Thr Glu Arg Thr Ala Asp Leu Trp Asp Arg Gln Ala Ser
        35                  40                  45

Gln Ser Ile Asp Gln Leu Ile Lys Arg Lys Gly Lys Leu Tyr Phe Gly
    50                  55                  60

Thr Ala Thr Asp Arg Gly Leu Leu Gln Arg Glu Lys Asn Ala Ala Ile
65                  70                  75                  80

Ile Gln Ala Asp Leu Gly Gln Val Thr Pro Glu Asn Ser Met Lys Trp
                85                  90                  95

Gln Ser Leu Glu Asn Asn Gln Gly Gln Leu Asn Trp Gly Asp Ala Asp
            100                 105                 110

Tyr Leu Val Asn Phe Ala Gln Gln Asn Gly Lys Ser Ile Arg Gly His
        115                 120                 125

Thr Leu Ile Trp His Ser Gln Leu Pro Ala Trp Val Asn Asn Ile Asn
    130                 135                 140

Asn Ala Asp Thr Leu Arg Gln Val Ile Arg Thr His Val Ser Thr Val
145                 150                 155                 160

Val Gly Arg Tyr Lys Gly Lys Ile Arg Ala Trp Asp Val Val Asn Glu
                165                 170                 175
```

```
Ile Phe Asn Glu Asp Gly Thr Leu Arg Ser Ser Val Phe Ser Arg Leu
                180                 185                 190

Leu Gly Glu Glu Phe Val Ser Ile Ala Phe Arg Ala Ala Arg Asp Ala
            195                 200                 205

Asp Pro Ser Ala Arg Leu Tyr Ile Asn Asp Tyr Asn Leu Asp Arg Ala
        210                 215                 220

Asn Tyr Gly Lys Val Asn Gly Leu Lys Thr Tyr Val Ser Lys Trp Ile
225                 230                 235                 240

Ser Gln Gly Val Pro Ile Asp Gly Ile Gly Ser Gln Ser His Leu Ser
                245                 250                 255

Gly Gly Gly Gly Ser Gly Thr Leu Gly Ala Leu Gln Gln Leu Ala Thr
            260                 265                 270

Val Pro Val Thr Glu Leu Ala Ile Thr Glu Leu Asp Ile Gln Gly Ala
        275                 280                 285

Pro Thr Thr Asp Tyr Thr Gln Val Gln Ala Cys Leu Ser Val Ser
    290                 295                 300

Lys Cys Val Gly Ile Thr Val Trp Gly Ile Ser Asp Lys Asp Ser Trp
305                 310                 315                 320

Arg Ala Ser Thr Asn Pro Leu Leu Phe Asp Ala Asn Phe Asn Pro Lys
                325                 330                 335

Pro Ala Tyr Asn Ser Ile Val Gly Ile Leu Gln
            340                 345

<210> SEQ ID NO 29
<211> LENGTH: 2564
<212> TYPE: DNA
<213> ORGANISM: Trichoderma reesei

<400> SEQUENCE: 29
ggacagccgg acgcaatggt gaataacgca gctcttctcg ccgccctgtc ggctctcctg      60
cccacggccc tggcgcagaa caatcaaaca tacgccaact actctgctca gggccagcct     120
gatctctacc ccgagacact tgccacgctc acactctcgt tccccgactg cgaacatggc     180
cccctcaaga caatctcgt ctgtgactca tcggccggct atgtagagcg agcccaggcc     240
ctcatctcgc tcttcacccct cgaggagctc attctcaaca cgcaaaactc gggccccggc     300
gtgcctcgcc tgggtcttcc gaactaccaa gtctggaatg aggctctgca cggcttggac     360
cgcgccaact tcgccaccaa gggcggccag ttcgaatggg cgacctcgtt ccccatgccc     420
atcctcacta cggcggccct caaccgcaca ttgatccacc agattgccga catcatctcg     480
acccaagctc gagcattcag caacagcggc cgttacggtc tcgacgtcta tgcgccaaac     540
gtcaatggct tccgaagccc cctctggggc cgtggccagg agacgcccgg cgaagacgcc     600
tttttcctca gctccgccta tcttacgag tacatcacgg gcatccaggg tggcgtcgac     660
cctgagcacc tcaaggttgc cgccacggtg aagcactttg ccggatacga cctcgagaac     720
tggaacaacc agtcccgtct cggtttcgac gccatcataa ctcagcagga cctctccgaa     780
tactacactc cccagttcct cgctgcggcc cgttatgcaa agtcacgcag cttgatgtgc     840
gcatacaact ccgtcaacgg cgtgcccagc tgtgccaaca gcttcttcct gcagacgctt     900
ttgcgcgaga gctggggctt ccccgaatgg ggatacgtct cgtccgattg cgatgccgtc     960
tacaacgttt tcaaccctca tgactacgcc agcaaccagt cgtcagccgc cgccagctca     1020
ctgcgagccg gcaccgatat cgactgcggt cagacttacc gtggcacct caacgagtcc     1080 tttgtggccg gcgaagtctc ccgcggcgag atcgagcggt ccgtcacccg tctgtacgcc     1140
```

```
aacctcgtcc gtctcggata cttcgacaag aagaaccagt accgctcgct cggttggaag    1200
gatgtcgtca agactgatgc ctggaacatc tcgtacgagg ctgctgttga gggcatcgtc    1260
ctgctcaaga acgatggcac tctccctctg tccaagaagg tgcgcagcat tgctctgatc    1320
ggaccatggg ccaatgccac aacccaaatg caaggcaact actatggccc tgccccatac    1380
ctcatcagcc ctctggaagc tgctaagaag gccggctatc acgtcaactt tgaactcggc    1440
acagagatcg ccggcaacag caccactggc tttgccaagg ccattgctgc cgccaagaag    1500
tcggatgcca tcatctacct cggtggaatt gacaacacca ttgaacagga gggcgctgac    1560
cgcacggaca ttgcttggcc cggtaatcag ctggatctca tcaagcagct cagcgaggtc    1620
ggcaaacccc ttgtcgtcct gcaaatgggc ggtggtcagg tagactcatc ctcgctcaag    1680
agcaacaaga aggtcaactc cctcgtctgg ggcggatatc ccggccagtc gggaggcgtt    1740
gccctcttcg acattctctc tggcaagcgt gctcctgccg ccgactggt caccactcag    1800 tacccggctg agtatgttca ccaattcccc cagaatgaca tgaacctccg acccgatgga    1860
aagtcaaacc ctggacagac ttacatctgg tacaccggca aacccgtcta cgagtttggc    1920
agtggtctct tctacaccac cttcaaggag actctcgcca gccaccccaa gagcctcaag    1980
ttcaacacct catcgatcct ctctgctcct caccccggat acacttacag cgagcagatt    2040
cccgtcttca ccttcgaggc caacatcaag aactcgggca agacggagtc cccatatacg    2100
gccatgctgt ttgttcgcac aagcaacgct ggcccagccc cgtacccgaa caagtggctc    2160
gtcggattcg accgacttgc cgacatcaag cctggtcact cttccaagct cagcatcccc    2220
atccctgtca gtgctctcgc ccgtgttgat tctcacggaa accggattgt ataccccggc    2280
aagtatgagc tagccttgaa caccgacgag tctgtgaagc ttgagtttga gttggtggga    2340
gaagaggtaa cgattgagaa ctggccgttg gaggagcaac agatcaagga tgctacacct    2400
gacgcataag ggttttaatg atgttgttat gacaaacggg tagagtagtt aatgatggaa    2460
taggaagagg ccatagtttt ctgtttgcaa accattttttg ccattgcgaa aaaaaaaaa    2520 aaaaaaaaaa aaaaaaaaaa aaaaaaaaaa aaaaaaaaa aaaa                    2564
```

<210> SEQ ID NO 30
<211> LENGTH: 780
<212> TYPE: PRT
<213> ORGANISM: Trichoderma reesei

<400> SEQUENCE: 30

```
Met Val Asn Asn Ala Ala Leu Leu Ala Leu Ser Ala Leu Leu Pro
1               5                   10                  15

Thr Leu Ala Gln Asn Asn Gln Thr Tyr Ala Asn Tyr Ser Ala Gln
                20                  25                  30

Gly Gln Pro Asp Leu Tyr Pro Glu Thr Leu Ala Thr Leu Thr Leu Ser
            35                  40                  45

Phe Pro Asp Cys Glu His Gly Pro Leu Lys Asn Leu Val Cys Asp
            50                  55                  60

Ser Ser Ala Gly Tyr Val Glu Arg Ala Gln Ala Leu Ile Ser Leu Phe
65                  70                  75                  80

Thr Leu Glu Glu Leu Ile Leu Asn Thr Gln Asn Ser Gly Pro Gly Val
                85                  90                  95

Pro Arg Leu Gly Leu Pro Asn Tyr Gln Val Trp Asn Glu Ala Leu His
            100                 105                 110

Gly Leu Asp Arg Ala Asn Phe Ala Thr Lys Gly Gly Gln Phe Glu Trp
```

```
            115                 120                 125
Ala Thr Ser Phe Pro Met Pro Ile Leu Thr Thr Ala Ala Leu Asn Arg
    130                 135                 140
Thr Leu Ile His Gln Ile Ala Asp Ile Ile Ser Thr Gln Ala Arg Ala
145                 150                 155                 160
Phe Ser Asn Ser Gly Arg Tyr Gly Leu Asp Val Tyr Ala Pro Asn Val
                165                 170                 175
Asn Gly Phe Arg Ser Pro Leu Trp Gly Arg Gly Gln Glu Thr Pro Gly
            180                 185                 190
Glu Asp Ala Phe Phe Leu Ser Ser Ala Tyr Thr Tyr Glu Tyr Ile Thr
        195                 200                 205
Gly Ile Gln Gly Gly Val Asp Pro Glu His Leu Lys Val Ala Ala Thr
    210                 215                 220
Val Lys His Phe Ala Gly Tyr Asp Leu Glu Asn Trp Asn Asn Gln Ser
225                 230                 235                 240
Arg Leu Gly Phe Asp Ala Ile Ile Thr Gln Gln Asp Leu Ser Glu Tyr
                245                 250                 255
Tyr Thr Pro Gln Phe Leu Ala Ala Arg Tyr Ala Lys Ser Arg Ser
            260                 265                 270
Leu Met Cys Ala Tyr Asn Ser Val Asn Gly Val Pro Ser Cys Ala Asn
        275                 280                 285
Ser Phe Phe Leu Gln Thr Leu Leu Arg Glu Ser Trp Gly Phe Pro Glu
    290                 295                 300
Trp Gly Tyr Val Ser Ser Asp Cys Asp Ala Val Tyr Asn Val Phe Asn
305                 310                 315                 320
Pro His Asp Tyr Ala Ser Asn Gln Ser Ser Ala Ala Ala Ser Ser Leu
                325                 330                 335
Arg Ala Gly Thr Asp Ile Asp Cys Gly Gln Thr Tyr Pro Trp His Leu
            340                 345                 350
Asn Glu Ser Phe Val Ala Gly Glu Val Ser Arg Gly Glu Ile Glu Arg
        355                 360                 365
Ser Val Thr Arg Leu Tyr Ala Asn Leu Val Arg Leu Gly Tyr Phe Asp
    370                 375                 380
Lys Lys Asn Gln Tyr Arg Ser Leu Gly Trp Lys Asp Val Val Lys Thr
385                 390                 395                 400
Asp Ala Trp Asn Ile Ser Tyr Glu Ala Ala Val Glu Gly Ile Val Leu
                405                 410                 415
Leu Lys Asn Asp Gly Thr Leu Pro Leu Ser Lys Lys Val Arg Ser Ile
            420                 425                 430
Ala Leu Ile Gly Pro Trp Ala Asn Ala Thr Thr Gln Met Gln Gly Asn
        435                 440                 445
Tyr Tyr Gly Pro Ala Pro Tyr Leu Ile Ser Pro Leu Glu Ala Ala Lys
    450                 455                 460
Lys Ala Gly Tyr His Val Asn Phe Glu Leu Gly Thr Glu Ile Ala Gly
465                 470                 475                 480
Asn Ser Thr Thr Gly Phe Ala Lys Ala Ile Ala Ala Lys Lys Ser
                485                 490                 495
Asp Ala Ile Ile Tyr Leu Gly Gly Ile Asp Asn Thr Ile Glu Gln Glu
            500                 505                 510
Gly Ala Asp Arg Thr Asp Ile Ala Trp Pro Gly Asn Gln Leu Asp Leu
        515                 520                 525
Ile Lys Gln Leu Ser Glu Val Gly Lys Pro Leu Val Val Leu Gln Met
    530                 535                 540
```

```
Gly Gly Gly Gln Val Asp Ser Ser Leu Lys Ser Asn Lys Lys Val
545                 550                 555                 560

Asn Ser Leu Val Trp Gly Gly Tyr Pro Gly Gln Ser Gly Gly Val Ala
            565                 570                 575

Leu Phe Asp Ile Leu Ser Gly Lys Arg Ala Pro Ala Gly Arg Leu Val
                580                 585                 590

Thr Thr Gln Tyr Pro Ala Glu Tyr Val His Gln Phe Pro Gln Asn Asp
            595                 600                 605

Met Asn Leu Arg Pro Asp Gly Lys Ser Asn Pro Gly Gln Thr Tyr Ile
610                 615                 620

Trp Tyr Thr Gly Lys Pro Val Tyr Glu Phe Gly Ser Gly Leu Phe Tyr
625                 630                 635                 640

Thr Thr Phe Lys Glu Thr Leu Ala Ser His Pro Lys Ser Leu Lys Phe
            645                 650                 655

Asn Thr Ser Ser Ile Leu Ser Ala Pro His Pro Gly Tyr Thr Tyr Ser
            660                 665                 670

Glu Gln Ile Pro Val Phe Thr Phe Glu Ala Asn Ile Lys Asn Ser Gly
            675                 680                 685

Lys Thr Glu Ser Pro Tyr Thr Ala Met Leu Phe Val Arg Thr Ser Asn
690                 695                 700

Ala Gly Pro Ala Pro Tyr Pro Asn Lys Trp Leu Val Gly Phe Asp Arg
705                 710                 715                 720

Leu Ala Asp Ile Lys Pro Gly His Ser Ser Lys Leu Ser Ile Pro Ile
                725                 730                 735

Pro Val Ser Ala Leu Ala Arg Val Asp Ser His Gly Asn Arg Ile Val
            740                 745                 750

Tyr Pro Gly Lys Tyr Glu Leu Ala Leu Asn Thr Asp Glu Ser Val Lys
            755                 760                 765

Leu Glu Phe Glu Leu Val Gly Glu Glu Val Thr Ile
770                 775                 780

<210> SEQ ID NO 31
<211> LENGTH: 40
<212> TYPE: DNA
<213> ORGANISM: Aspergillus fumigatus

<400> SEQUENCE: 31
cgcggactgc gcaccatgct ggcctccacc ttctcctacc                          40

<210> SEQ ID NO 32
<211> LENGTH: 48
<212> TYPE: DNA
<213> ORGANISM: Aspergillus fumigatus

<400> SEQUENCE: 32
ctttcgccac ggagcttaat taactacagg cactgagagt aataatca                 48

<210> SEQ ID NO 33
<211> LENGTH: 1131
<212> TYPE: DNA
<213> ORGANISM: Herpes simplex virus

<400> SEQUENCE: 33
atggcttcgt accccggcca tcaacacgcg tctgcgttcg accaggctgc gcgttctcgc    60
ggccatagca accgacgtac ggcgttgcgc cctcgccggc agcaagaagc cacggaagtc    120
cgcccggagc agaaaatgcc cacgctactg cgggtttata tagacggtcc ccacgggatg    180
```

```
gggaaaacca ccaccacgca actgctggtg gccctgggtt cgcgcgacga tatcgtctac      240
gtacccgagc cgatgactta ctggcggtg ctggggggctt ccgagacaat cgcgaacatc      300
tacaccacac aacaccgcct cgaccagggt gagatatcgg ccggggacgc ggcggtggta      360
atgacaagcg cccagataac aatgggcatg ccttatgccg tgaccgacgc cgttctggct      420
cctcatatcg gggggaggc tgggagctca catgccccgc ccccggccct caccctcatc       480
ttcgaccgcc atcccatcgc cgccctcctg tgctacccgg ccgcgcggta ccttatgggc      540
agcatgaccc ccaggccgt gctggcgttc gtggccctca tcccgccgac cttgcccggc       600
accaacatcg tgcttggggc ccttccggag acagacaca tcgaccgcct ggccaaacgc       660
cagcgccccg gcgagcggct ggacctggct atgctggctg cgattcgccg cgtttacggg      720
ctacttgcca atacggtgcg gtatctgcag tgcggcgggt cgtggcggga ggactgggga      780
cagctttcgg ggacggccgt gccgccccag ggtgccgagc cccagagcaa cgcgggccca      840
cgaccccata tcggggacac gttatttacc ctgtttcggg ccccgagtt gctggccccc       900 aacggcgacc tgtataacgt gtttgcctgg gccttggacg tcttggccaa cgcctccgt       960 tccatgcacg tctttatcct ggattacgac caatcgcccg ccggctgccg ggacgccctg     1020
ctgcaactta cctccgggat ggtccagacc cacgtcacca ccccggctc cataccgacg      1080 atatgcgacc tggcgcgcac gtttgcccgg gagatggggg aggctaactg a              1131
```

<210> SEQ ID NO 34
<211> LENGTH: 376
<212> TYPE: PRT
<213> ORGANISM: Herpes simplex virus

<400> SEQUENCE: 34

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Pro Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Arg Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

```
Pro Glu Asp Arg His Ile Asp Arg Leu Ala Lys Arg Gln Arg Pro Gly
    210                 215                 220
Glu Arg Leu Asp Leu Ala Met Leu Ala Ala Ile Arg Arg Val Tyr Gly
225                 230                 235                 240
Leu Leu Ala Asn Thr Val Arg Tyr Leu Gln Cys Gly Gly Ser Trp Arg
                245                 250                 255
Glu Asp Trp Gly Gln Leu Ser Gly Thr Ala Val Pro Pro Gln Gly Ala
            260                 265                 270
Glu Pro Gln Ser Asn Ala Gly Pro Arg Pro His Ile Gly Asp Thr Leu
        275                 280                 285
Phe Thr Leu Phe Arg Gly Pro Glu Leu Leu Ala Pro Asn Gly Asp Leu
    290                 295                 300
Tyr Asn Val Phe Ala Trp Ala Leu Asp Val Leu Ala Lys Arg Leu Arg
305                 310                 315                 320
Ser Met His Val Phe Ile Leu Asp Tyr Asp Gln Ser Pro Ala Gly Cys
                325                 330                 335
Arg Asp Ala Leu Leu Gln Leu Thr Ser Gly Met Val Gln Thr His Val
            340                 345                 350
Thr Thr Pro Gly Ser Ile Pro Thr Ile Cys Asp Leu Ala Arg Thr Phe
        355                 360                 365
Ala Arg Glu Met Gly Glu Ala Asn
    370                 375
```

<210> SEQ ID NO 35
<211> LENGTH: 43
<212> TYPE: DNA
<213> ORGANISM: Trichoderma reesei

<400> SEQUENCE: 35
ttagactgcg gccgcgtggc gaaagcctga cgcaccggta gat          43

<210> SEQ ID NO 36
<211> LENGTH: 41
<212> TYPE: DNA
<213> ORGANISM: Trichoderma reesei

<400> SEQUENCE: 36
agtagttagc ggccgcacgg cacggttaag cagggtcttg c            41

<210> SEQ ID NO 37
<211> LENGTH: 25
<212> TYPE: DNA
<213> ORGANISM: Trichoderma reesei

<400> SEQUENCE: 37
aaaaaacaaa catcccgttc ataac                              25

<210> SEQ ID NO 38
<211> LENGTH: 25
<212> TYPE: DNA
<213> ORGANISM: Trichoderma reesei

<400> SEQUENCE: 38
aacaaggttt accggtttcg aaaag                              25

<210> SEQ ID NO 39
<211> LENGTH: 54
<212> TYPE: DNA
<213> ORGANISM: Trichoderma reesei

<400> SEQUENCE: 39
acgaattgtt taaacgtcga cccaagtatc cagaggtgta tggaaatatc agat    54

<210> SEQ ID NO 40
<211> LENGTH: 44
<212> TYPE: DNA
<213> ORGANISM: Trichoderma reesei

<400> SEQUENCE: 40
cgcgtagatc tgcggccatg gtgcaataca cagagggtga tctt    44

<210> SEQ ID NO 41
<211> LENGTH: 48
<212> TYPE: DNA
<213> ORGANISM: Trichoderma reesei

<400> SEQUENCE: 41
atctacgcgt actagttaat taaggctttc gtgaccgggc ttcaaaca    48

<210> SEQ ID NO 42
<211> LENGTH: 46
<212> TYPE: DNA
<213> ORGANISM: Trichoderma reesei

<400> SEQUENCE: 42
gcggccgtta ctagtggatc cactcggagt tgttatacgc tactcg    46

<210> SEQ ID NO 43
<211> LENGTH: 46
<212> TYPE: DNA
<213> ORGANISM: Trichoderma reesei

<400> SEQUENCE: 43
atccatcaca ctggcggccg cgcttcaaac aatgatgtgc gatggt    46

<210> SEQ ID NO 44
<211> LENGTH: 46
<212> TYPE: DNA
<213> ORGANISM: Trichoderma reesei

<400> SEQUENCE: 44
gatgcatgct cgagcggccg cctaccttgg cagccctacg agagag    46

<210> SEQ ID NO 45
<211> LENGTH: 41
<212> TYPE: DNA
<213> ORGANISM: Aspergillus fumigatus

<400> SEQUENCE: 45
ctctgtgtat tgcaccatga agcaccttgc atcttccatc g    41

<210> SEQ ID NO 46
<211> LENGTH: 40
<212> TYPE: DNA
<213> ORGANISM: Aspergillus fumigatus

<400> SEQUENCE: 46
ccggtcacga aagccttaat taaaggacg ggttagcgtt    40

<210> SEQ ID NO 47
<211> LENGTH: 25
<212> TYPE: DNA

```
<213> ORGANISM: Trichoderma reesei

<400> SEQUENCE: 47
agccacatgc cgcatattga caaag                                            25

<210> SEQ ID NO 48
<211> LENGTH: 25
<212> TYPE: DNA
<213> ORGANISM: Aspergillus fumigatus

<400> SEQUENCE: 48
agggattcag tgtgctacag gctgc                                            25

<210> SEQ ID NO 49
<211> LENGTH: 25
<212> TYPE: DNA
<213> ORGANISM: Trichoderma reesei

<400> SEQUENCE: 49
aaaaaacaaa catcccgttc ataac                                            25

<210> SEQ ID NO 50
<211> LENGTH: 25
<212> TYPE: DNA
<213> ORGANISM: Trichoderma reesei

<400> SEQUENCE: 50
aacaaggttt accggtttcg aaaag                                            25

<210> SEQ ID NO 51
<211> LENGTH: 27
<212> TYPE: DNA
<213> ORGANISM: Trichoderma reesei

<400> SEQUENCE: 51
gttaagcata caattgaacg agaatgg                                          27

<210> SEQ ID NO 52
<211> LENGTH: 25
<212> TYPE: DNA
<213> ORGANISM: Trichoderma reesei

<400> SEQUENCE: 52
gatgatataa tggagcaaat aaggg                                            25

<210> SEQ ID NO 53
<211> LENGTH: 2077
<212> TYPE: DNA
<213> ORGANISM: Trichoderma reesei

<400> SEQUENCE: 53
atgacggatg cacaaaagaa ttggaggaga gacgaaaacg acgaggacga tgaagcagag      60
caggagctcg atgaggctgt aagtcgccgc gagtcgcatc tggtctgaca agcgtcgtct     120
gacactcttt tctcccatct agagcctcaa ggcgcagaaa gatgcaattc ttctagccat     180
tgaagtcagt ccgtcgatgc ttgagcctcc gccagtctcc agctctagga agctgatcg     240 ggacagcccc gttcaagctg cgctgaaatg cgcccgccac ctgatggagc agcgcatcat     300
ctccaacccc aaagacatga tgggaatcct cctctttggg acagaaaaga ccaagttccg     360
ggacgacaat ggccgcagtg ggctcgggta tccgaattgc tacctcttta tggacctcga     420
cattccggca gctgaagacg tcaaagcgtt gaaggcgctg accgaggacg aagacgaaga     480
```

```
cgaagtgctg aagcccgcca ccaccgacac agtttccatg tccaacgtgt tgttttgcgc    540
caaccagata ttcaccacaa aggcggccaa ctttggcagc cggcgacttt tcattgtgac    600
ggacaatgac gatccgcacg cgtcggacaa ggcggcgagg tctgctgccg ctgttcgggc    660
aaaggacttg tacgatctgg gcatcacgat cgacttgttt ccaatcacca caggagactc    720
caagtttgat ctcagcaaat tttacgatgt aagctatatt tcttcgtttc ttcgctctaa    780
aatcacccac cctccgtcgt gacatagact gacaaggaac taggatattg tctatcgcga    840
cccgaatgcc gaggccaatc gcaccgaagt gcgagcctca aaatcgggcg atggactgtc    900
tcttctcaac tcgctcattt caaacatcaa ttccaagcag acgcccaagc gagcattgtt    960
ccatctgcca tttgagattg cacctggact caagatcact gtcaagggct acaacattgt   1020
gcatcggcaa acgccggcga gaacgtgcta catctggctg aaggggagaa aggctcagat   1080
tgcaacaggc gaaacgacgc gagttgcaga ggattctgcc agaacagtcg aaaagcaaga   1140
gataaaaaag gcctacaagt ttggtggcga atacgtatac tttacgcccg aggagcagaa   1200
gaagctccgg gattttggcg cgcccacgat ccggatcatt ggattcaaga agcgcagcat   1260
gattcccgtc tgggccagcg tcaagaagtc gacctttatc tttcccagcg aagaggatta   1320
catcggatcg acacgcgtct tttcagccct atggcagaag cttctaaagg atgacaagat   1380
cggcctcgct tggtgcgtgc ttcgatctaa cgcgcagccc atgtttgccg ctctgattcc   1440
atcaagagag cagtccgaag acgacgcggg gacaccatat ctaccagctg gcctgtggct   1500
gtatcctctc cctacggctg acgacctgcg agatataaat gtcgaacgaa agctcgactg   1560
ctcggaggac ctaaaaacca aaatgagagt cattgtacaa cagctcaatc tccccaaggg   1620
catatataac ccactcaagt acccgaaccc ggctctgcaa tggcactaca agatcctcca   1680
gaccctcgcc ttggaggagg agatgccgga agaacccgaa gacttgacgg agcccaaaaa   1740
caaggcgata agcaaacgcg tcggaggtta cttggaggag tggtccgaga ctctgaaaga   1800
cgaggcggac agggccactc gatccaggtc cttgaagcga gagattgaag atgatgcccc   1860
ggagcgcccc gcaaagcaga gaaaggtagc tggagagcgg cccagcggat cgaatcttag   1920
catggcgcag cttagggatg ccattgagag cgggagcatc tcgaagatga cagtggcaca   1980
gctgaaggat gtcgctggcg ccagaggact cagcacgggt ggtaagaagg ctgatttgct   2040
ggagcggata gagcagtggg ttgaggagaa cagctga                            2077
```

<210> SEQ ID NO 54
<211> LENGTH: 649
<212> TYPE: PRT
<213> ORGANISM: Trichoderma reesei

<400> SEQUENCE: 54

Met Thr Asp Ala Gln Lys Asn Trp Arg Arg Asp Glu Asn Asp Glu Asp
1               5                   10                  15

Asp Glu Ala Glu Gln Glu Leu Asp Glu Ala Val Ser Arg Arg Asp Leu
            20                  25                  30

Lys Ala Gln Lys Asp Ala Ile Leu Leu Ala Ile Glu Val Ser Pro Ser
        35                  40                  45

Met Leu Glu Pro Pro Val Ser Ser Arg Lys Ala Asp Arg Asp
    50                  55                  60

Ser Pro Val Gln Ala Ala Leu Lys Cys Ala Arg His Leu Met Glu Gln
65                  70                  75                  80

Arg Ile Ile Ser Asn Pro Lys Asp Met Met Gly Ile Leu Leu Phe Gly

```
                    85                  90                  95
Thr Glu Lys Thr Lys Phe Arg Asp Asp Asn Gly Arg Ser Gly Leu Gly
                100                 105                 110

Tyr Pro Asn Cys Tyr Leu Phe Met Asp Leu Asp Ile Pro Ala Ala Glu
                115                 120                 125

Asp Val Lys Ala Leu Lys Ala Leu Thr Glu Asp Glu Asp Glu Asp Glu
            130                 135                 140

Val Leu Lys Pro Ala Thr Thr Asp Thr Val Ser Met Ser Asn Val Leu
145                 150                 155                 160

Phe Cys Ala Asn Gln Ile Phe Thr Thr Lys Ala Ala Asn Phe Gly Ser
                165                 170                 175

Arg Arg Leu Phe Ile Val Thr Asp Asn Asp Pro His Ala Ser Asp
                180                 185                 190

Lys Ala Ala Arg Ser Ala Ala Val Arg Ala Lys Asp Leu Tyr Asp
                195                 200                 205

Leu Gly Ile Thr Ile Asp Leu Phe Pro Ile Thr Thr Gly Asp Ser Lys
            210                 215                 220

Phe Asp Leu Ser Lys Phe Tyr Asp Asp Ile Val Tyr Arg Asp Pro Asn
225                 230                 235                 240

Ala Glu Ala Asn Arg Thr Glu Val Arg Ala Ser Lys Ser Gly Asp Gly
                245                 250                 255

Leu Ser Leu Leu Asn Ser Leu Ile Ser Asn Ile Asn Ser Lys Gln Thr
            260                 265                 270

Pro Lys Arg Ala Leu Phe His Leu Pro Phe Glu Ile Ala Pro Gly Leu
        275                 280                 285

Lys Ile Thr Val Lys Gly Tyr Asn Ile Val His Arg Gln Thr Pro Ala
290                 295                 300

Arg Thr Cys Tyr Ile Trp Leu Glu Gly Glu Lys Ala Gln Ile Ala Thr
305                 310                 315                 320

Gly Glu Thr Thr Arg Val Ala Glu Asp Ser Ala Arg Thr Val Glu Lys
                325                 330                 335

Gln Glu Ile Lys Lys Ala Tyr Lys Phe Gly Gly Glu Tyr Val Tyr Phe
            340                 345                 350

Thr Pro Glu Glu Gln Lys Lys Leu Arg Asp Phe Gly Ala Pro Thr Ile
        355                 360                 365

Arg Ile Ile Gly Phe Lys Lys Arg Ser Met Ile Pro Val Trp Ala Ser
370                 375                 380

Val Lys Lys Ser Thr Phe Ile Phe Pro Ser Glu Glu Asp Tyr Ile Gly
385                 390                 395                 400

Ser Thr Arg Val Phe Ser Ala Leu Trp Gln Lys Leu Leu Lys Asp Asp
                405                 410                 415

Lys Ile Gly Leu Ala Trp Cys Val Leu Arg Ser Asn Ala Gln Pro Met
            420                 425                 430

Phe Ala Ala Leu Ile Pro Ser Arg Glu Gln Ser Glu Asp Asp Ala Gly
        435                 440                 445

Thr Pro Tyr Leu Pro Ala Gly Leu Trp Leu Tyr Pro Leu Pro Thr Ala
    450                 455                 460

Asp Asp Leu Arg Asp Ile Asn Val Glu Arg Lys Leu Asp Cys Ser Glu
465                 470                 475                 480

Asp Leu Lys Thr Lys Met Arg Val Ile Gln Gln Leu Asn Leu Pro
                485                 490                 495

Lys Gly Ile Tyr Asn Pro Leu Lys Tyr Pro Asn Pro Ala Leu Gln Trp
            500                 505                 510
```

```
His Tyr Lys Ile Leu Gln Thr Leu Ala Leu Glu Glu Met Pro Glu
        515                 520                 525

Glu Pro Glu Asp Leu Thr Glu Pro Lys Asn Lys Ala Ile Ser Lys Arg
530                 535                 540

Val Gly Gly Tyr Leu Glu Glu Trp Ser Glu Thr Leu Lys Asp Glu Ala
545                 550                 555                 560

Asp Arg Ala Thr Arg Ser Arg Ser Leu Lys Arg Glu Ile Glu Asp Asp
                565                 570                 575

Ala Pro Glu Arg Pro Ala Lys Gln Arg Lys Val Ala Gly Glu Arg Pro
            580                 585                 590

Ser Gly Ser Asn Leu Ser Met Ala Gln Leu Arg Asp Ala Ile Glu Ser
        595                 600                 605

Gly Ser Ile Ser Lys Met Thr Val Ala Gln Leu Lys Asp Val Ala Gly
        610                 615                 620

Ala Arg Gly Leu Ser Thr Gly Gly Lys Lys Ala Asp Leu Leu Glu Arg
625                 630                 635                 640

Ile Glu Gln Trp Val Glu Glu Asn Ser
                645

<210> SEQ ID NO 55
<211> LENGTH: 55
<212> TYPE: DNA
<213> ORGANISM: Trichoderma reesei

<400> SEQUENCE: 55
gtgtgcggcc gctcgagcat gcatgtttaa acagcttggc actggccgtc gtttt      55

<210> SEQ ID NO 56
<211> LENGTH: 55
<212> TYPE: DNA
<213> ORGANISM: Trichoderma reesei

<400> SEQUENCE: 56
atcagccccg agacggcgcc gcgtttaaac aattcgtaat catggtcata gctgt      55

<210> SEQ ID NO 57
<211> LENGTH: 55
<212> TYPE: DNA
<213> ORGANISM: Trichoderma reesei

<400> SEQUENCE: 57
catgattacg aattgtttaa acgcggcgcc gtctcggggc tgatcttgtc gagga      55

<210> SEQ ID NO 58
<211> LENGTH: 55
<212> TYPE: DNA
<213> ORGANISM: Trichoderma reesei

<400> SEQUENCE: 58
ggcggccgtt actagtggat ccagcccttg acagtgatct gagtccagg tgcaa       55

<210> SEQ ID NO 59
<211> LENGTH: 58
<212> TYPE: DNA
<213> ORGANISM: Trichoderma reesei

<400> SEQUENCE: 59
tgcagatatc catcacactg gcggccgcag tttccatgtc caacgtgttg ttttgcgc   58
```

```
<210> SEQ ID NO 60
<211> LENGTH: 58
<212> TYPE: DNA
<213> ORGANISM: Trichoderma reesei

<400> SEQUENCE: 60
gccagtgcca agctgtttaa acatgcatgc tcgagcggcc gcacacgccc tctcctcg      58

<210> SEQ ID NO 61
<211> LENGTH: 20
<212> TYPE: DNA
<213> ORGANISM: Trichoderma reesei

<400> SEQUENCE: 61
caatgacgat ccgcacgcgt                                                 20

<210> SEQ ID NO 62
<211> LENGTH: 20
<212> TYPE: DNA
<213> ORGANISM: Trichoderma reesei

<400> SEQUENCE: 62
caatgacgat ccgcacgcgt                                                 20

<210> SEQ ID NO 63
<211> LENGTH: 20
<212> TYPE: DNA
<213> ORGANISM: Trichoderma reesei

<400> SEQUENCE: 63
gacactcttt tctcccatct                                                 20

<210> SEQ ID NO 64
<211> LENGTH: 20
<212> TYPE: DNA
<213> ORGANISM: Trichoderma reesei

<400> SEQUENCE: 64
gaggagcaga agaagctccg                                                 20

<210> SEQ ID NO 65
<211> LENGTH: 22
<212> TYPE: DNA
<213> ORGANISM: Trichoderma reesei

<400> SEQUENCE: 65
gcatatataa cccactcaag ta                                              22

<210> SEQ ID NO 66
<211> LENGTH: 22
<212> TYPE: DNA
<213> ORGANISM: Trichoderma reesei

<400> SEQUENCE: 66
attatcttgg accggccgca gg                                              22

<210> SEQ ID NO 67
<211> LENGTH: 36
<212> TYPE: DNA
<213> ORGANISM: Penicillium sp.

<400> SEQUENCE: 67
cggactgcgc accatgctgt cttcgacgac tcgcac                               36
```

<210> SEQ ID NO 68
<211> LENGTH: 35
<212> TYPE: DNA
<213> ORGANISM: Penicillium sp.

<400> SEQUENCE: 68
tcgccacgga gcttatcgac ttcttctaga acgtc        35

<210> SEQ ID NO 69
<211> LENGTH: 36
<212> TYPE: DNA
<213> ORGANISM: Aspergillus fumigatus

<400> SEQUENCE: 69
ccctttgggt atccgtgact gtgagctata cccgcg        36

<210> SEQ ID NO 70
<211> LENGTH: 35
<212> TYPE: DNA
<213> ORGANISM: Aspergillus fumigatus

<400> SEQUENCE: 70
cgtcatgagt gactggggcg ctcaccacag cggtg        35

<210> SEQ ID NO 71
<211> LENGTH: 36
<212> TYPE: DNA
<213> ORGANISM: Aspergillus fumigatus

<400> SEQUENCE: 71
gggtagtggt actgccgagt tcccttacct tgtcac        36

<210> SEQ ID NO 72
<211> LENGTH: 39
<212> TYPE: DNA
<213> ORGANISM: Aspergillus fumigatus

<400> SEQUENCE: 72
gccgactctg gagagggtta catcagtgtc gacggcaac        39

<210> SEQ ID NO 73
<211> LENGTH: 33
<212> TYPE: DNA
<213> ORGANISM: Aspergillus fumigatus

<400> SEQUENCE: 73
cggactgcgc accatgagat tcggttggct cga        33

<210> SEQ ID NO 74
<211> LENGTH: 35
<212> TYPE: DNA
<213> ORGANISM: Aspergillus fumigatus

<400> SEQUENCE: 74
tcgccacgga gcttactagt agacacgggg cagag        35

<210> SEQ ID NO 75
<211> LENGTH: 31
<212> TYPE: DNA
<213> ORGANISM: Humicola insolens

<400> SEQUENCE: 75
tataagctta agcatgcgtt cctcccccct c        31

<210> SEQ ID NO 76
<211> LENGTH: 32
<212> TYPE: DNA
<213> ORGANISM: Humicola insolens

<400> SEQUENCE: 76
ctgcagaatt ctacaggcac tgatggtacc ag                            32

<210> SEQ ID NO 77
<211> LENGTH: 36
<212> TYPE: DNA
<213> ORGANISM: Trichoderma reesei

<400> SEQUENCE: 77
acgcgtcgac gaattctagg ctaggtatgc gaggca                        36

<210> SEQ ID NO 78
<211> LENGTH: 23
<212> TYPE: DNA
<213> ORGANISM: Trichoderma reesei

<400> SEQUENCE: 78
catggtgcaa tacacagagg gtg                                      23

<210> SEQ ID NO 79
<211> LENGTH: 32
<212> TYPE: DNA
<213> ORGANISM: Trichoderma reesei

<400> SEQUENCE: 79
gtgtattgca ccatggcgtt cctccccct cc                             32

<210> SEQ ID NO 80
<211> LENGTH: 31
<212> TYPE: DNA
<213> ORGANISM: Trichoderma reesei

<400> SEQUENCE: 80 ggaggggga ggaacgccat ggtgcaatac a                              31

<210> SEQ ID NO 81
<211> LENGTH: 40
<212> TYPE: DNA
<213> ORGANISM: Aspergillus fumigatus

<400> SEQUENCE: 81
caccctctgt gtattgcacc atgagattcg gttggctcga                    40

<210> SEQ ID NO 82
<211> LENGTH: 40
<212> TYPE: DNA
<213> ORGANISM: Aspergillus fumigatus

<400> SEQUENCE: 82
ttcgccacgg agctactagt ctagtagaca cggggcagag                    40

<210> SEQ ID NO 83
<211> LENGTH: 36
<212> TYPE: DNA
<213> ORGANISM: Aspergillus fumigatus

<400> SEQUENCE: 83

```
actggattta ccatggcggt tgccaaatct attgct                               36
```

<210> SEQ ID NO 84
<211> LENGTH: 38
<212> TYPE: DNA
<213> ORGANISM: Aspergillus fumigatus

<400> SEQUENCE: 84

```
tcacctctag ttaattaatc acgcagacga aatctgct                             38
```

<210> SEQ ID NO 85
<211> LENGTH: 30
<212> TYPE: DNA
<213> ORGANISM: Aspergillus fumigatus

<400> SEQUENCE: 85

```
cggactgcgc accatggcgg ttgccaaatc                                      30
```

<210> SEQ ID NO 86
<211> LENGTH: 32
<212> TYPE: DNA
<213> ORGANISM: Aspergillus fumigatus

<400> SEQUENCE: 86

```
tcgccacgga gcttatcacg cagacgaaat ct                                   32
```

<210> SEQ ID NO 87
<211> LENGTH: 33
<212> TYPE: DNA
<213> ORGANISM: Aspergillus fumigatus

<400> SEQUENCE: 87

```
cggactgcgc accatggtcc atctatcttc att                                  33
```

<210> SEQ ID NO 88
<211> LENGTH: 35
<212> TYPE: DNA
<213> ORGANISM: Aspergillus fumigatus

<400> SEQUENCE: 88

```
tcgccacgga gcttattaca ggcactgtga gtacc                                35
```

<210> SEQ ID NO 89
<211> LENGTH: 1377
<212> TYPE: DNA
<213> ORGANISM: Trichoderma reesei

<400> SEQUENCE: 89

```
atggcgccct cagttacact gccgttgacc acggccatcc tggccattgc ccggctcgtc    60
gccgcccagc aaccgggtac cagcaccccc gaggtccatc ccaagttgac aacctacaag   120
tgtacaaagt ccgggggggtg cgtggcccag acacctcgg tggtccttga ctggaactac   180
cgctggatgc acgacgcaaa ctacaactcg tgcaccgtca acgcggcgt caacaccacg   240
ctctgccctg acgaggcgac ctgtggcaag aactgcttca tcgagggcgt cgactacgcc   300
gcctcgggcg tcacgacctc gggcagcagc ctcaccatga accagtacat gcccagcagc   360
tctggcggct acagcagcgt ctctcctcgg ctgtatctcc tggactctga cggtgagtac   420
gtgatgctga agctcaacgg ccaggagctg agcttcgacg tcgacctctc tgctctgccg   480
tgtggagaga acggctcgct ctacctgtct cagatggacg agaacggggg cgccaaccag   540
tataacacgg ccggtgccaa ctacgggagc ggctactgcg atgctcagtg ccccgtccag   600
```

-continued

```
acatggagga acggcaccct caacactagc caccagggct tctgctgcaa cgagatggat    660
atcctggagg gcaactcgag ggcgaatgcc ttgacccctc actcttgcac ggccacggcc    720
tgcgactctg ccggttgcgg cttcaacccc tatggcagcg gctacaaaag ctactacggc    780
cccggagata ccgttgacac ctccaagacc ttcaccatca tcacccagtt caacacggac    840
aacggctcgc cctcgggcaa ccttgtgagc atcacccgca agtaccagca aacggcgtc    900
gacatcccca cgcccagcc cggcggcgac accatctcgt cctgcccgtc cgcctcagcc    960
tacggcggcc tcgccaccat gggcaaggcc ctgagcagcg catggtgct cgtgttcagc   1020
atttggaacg acaacagcca gtacatgaac tggctcgaca cggcaacgc cggcccctgc   1080
agcagcaccg agggcaaccc atccaacatc ctggccaaca ccccaacac gcacgtcgtc   1140
ttctccaaca tccgctgggg agacattggg tctactacga actcgactgc gcccccgccc   1200
ccgcctgcgt ccagcacgac gttttcgact acacggagga gctcgacgac ttcgagcagc   1260
ccgagctgca cgcagactca ctgggggcag tgcggtggca ttgggtacag cgggtgcaag   1320
acgtgcacgt cgggcactac gtgccagtat agcaacgact actactcgca atgcctt      1377
```

<210> SEQ ID NO 90
<211> LENGTH: 459
<212> TYPE: PRT
<213> ORGANISM: Trichoderma reesei

<400> SEQUENCE: 90

```
Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
            20                  25                  30

His Pro Lys Leu Thr Thr Tyr Lys Cys Thr Lys Ser Gly Gly Cys Val
        35                  40                  45

Ala Gln Asp Thr Ser Val Val Leu Asp Trp Asn Tyr Arg Trp Met His
    50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
                85                  90                  95

Val Asp Tyr Ala Ala Ser Gly Val Thr Thr Ser Gly Ser Ser Leu Thr
            100                 105                 110

Met Asn Gln Tyr Met Pro Ser Ser Gly Gly Tyr Ser Ser Val Ser
        115                 120                 125

Pro Arg Leu Tyr Leu Leu Asp Ser Asp Gly Glu Tyr Val Met Leu Lys
    130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
        195                 200                 205

Thr Ser His Gln Gly Phe Cys Cys Asn Glu Met Asp Ile Leu Glu Gly
    210                 215                 220

Asn Ser Arg Ala Asn Ala Leu Thr Pro His Ser Cys Thr Ala Thr Ala
225                 230                 235                 240
```

Cys Asp Ser Ala Gly Cys Gly Phe Asn Pro Tyr Ser Gly Tyr Lys
            245                 250                 255

Ser Tyr Tyr Gly Pro Gly Asp Thr Val Asp Thr Ser Lys Thr Phe Thr
                260                 265                 270

Ile Ile Thr Gln Phe Asn Thr Asp Asn Gly Ser Pro Ser Gly Asn Leu
            275                 280                 285

Val Ser Ile Thr Arg Lys Tyr Gln Gln Asn Gly Val Asp Ile Pro Ser
        290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
            340                 345                 350

Asp Ser Gly Asn Ala Gly Pro Cys Ser Ser Thr Glu Gly Asn Pro Ser
        355                 360                 365

Asn Ile Leu Ala Asn Asn Pro Asn Thr His Val Val Phe Ser Asn Ile
    370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
                405                 410                 415

Thr Ser Ser Ser Pro Ser Cys Thr Gln Thr His Trp Gly Gln Cys Gly
            420                 425                 430

Gly Ile Gly Tyr Ser Gly Cys Lys Thr Cys Thr Ser Gly Thr Thr Cys
        435                 440                 445

Gln Tyr Ser Asn Asp Tyr Tyr Ser Gln Cys Leu
    450                 455

<210> SEQ ID NO 91
<211> LENGTH: 1254
<212> TYPE: DNA
<213> ORGANISM: Trichoderma reesei

<400> SEQUENCE: 91
atgaacaagt ccgtggctcc attgctgctt gcagcgtcca tactatatgg cggcgccgtc        60
gcacagcaga ctgtctgggg ccagtgtgga ggtattggtt ggagcggacc tacgaattgt       120
gctcctggct cagcttgttc gaccctcaat ccttattatg cgcaatgtat tccgggagcc       180
actactatca ccacttcgac ccggccacca tccggtccaa ccaccaccac cagggctacc       240
tcaacaagct catcaactcc acccacgagc tctggggtcc gatttgccgg cgttaacatc       300
gcgggttttg actttggctg taccacagat ggcacttgcg ttacctcgaa ggtttatcct       360
ccgttgaaga acttcaccgg ctcaaacaac taccccgatg gcatcggcca gatgcagcac       420
ttcgtcaacg aggacgggat gactattttc cgcttacctg tcggatggca gtacctcgtc       480
aacaacaatt tgggcggcaa tcttgattcc acgagcattt ccaagtatga tcagcttgtt       540
cagggggtgc tgtctctggg cgcatactgc atcgtcgaca tccacaatta tgctcgatgg       600
aacggtggga tcattggtca gggcggccct actaatgctc aattcacgag cctttggtcg       660
cagttggcat caaagtacgc atctcagtcg agggtgtggt tcggcatcat gaatgagccc       720
cacgacgtga acatcaacac ctgggctgcc acgtccaag aggttgtaac cgcaatccgc       780
aacgctggtg ctacgtcgca attcatctct ttgcctggaa atgattggca atctgctggg       840

```
gctttcatat ccgatggcag tgcagccgcc ctgtctcaag tcacgaaccc ggatgggtca      900
acaacgaatc tgattttttga cgtgcacaaa tacttggact cagacaactc cggtactcac     960
```

```
gctttcatat ccgatggcag tgcagccgcc ctgtctcaag tcacgaaccc ggatgggtca      900
acaacgaatc tgattttttga cgtgcacaaa tacttggact cagacaactc cggtactcac     960
gccgaatgta ctacaaataa cattgacggc gccttttctc cgcttgccac ttggctccga     1020
cagaacaatc gccaggctat cctgacagaa accggtggtg caacgttca gtcctgcata      1080 caagacatgt gccagcaaat ccaatatctc aaccagaact cagatgtcta tcttggctat     1140
gttggttggg gtgccggatc atttgatagc acgtatgtcc tgacggaaac accgactagc     1200
agtggtaact catggacgga cacatccttg gtcagctcgt gtctcgcaag aaag           1254
```

<210> SEQ ID NO 92
<211> LENGTH: 418
<212> TYPE: PRT
<213> ORGANISM: Trichoderma reesei

<400> SEQUENCE: 92

```
Met Asn Lys Ser Val Ala Pro Leu Leu Ala Ala Ser Ile Leu Tyr
1               5                   10                  15

Gly Gly Ala Val Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Glu
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300
```

```
Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
                325                 330                 335

Thr Trp Leu Arg Gln Asn Asn Arg Gln Ala Ile Leu Thr Glu Thr Gly
            340                 345                 350

Gly Gly Asn Val Gln Ser Cys Ile Gln Asp Met Cys Gln Gln Ile Gln
        355                 360                 365

Tyr Leu Asn Gln Asn Ser Asp Val Tyr Leu Gly Tyr Val Gly Trp Gly
    370                 375                 380

Ala Gly Ser Phe Asp Ser Thr Tyr Val Leu Thr Glu Thr Pro Thr Ser
385                 390                 395                 400

Ser Gly Asn Ser Trp Thr Asp Thr Ser Leu Val Ser Ser Cys Leu Ala
                405                 410                 415

Arg Lys
```

CELLULOLYTIC ENZYME COMPOSITIONS AND USES THEREOF

CROSS-REFERENCE TO RELATED APPLICATIONS

This application is a continuation application of U.S. application Ser. No. 16/268,922 filed on Feb. 6, 2019, now U.S. Pat. No. 10,662,456, which is a divisional application of U.S. application Ser. No. 16/122,173 filed on Sep. 5, 2018, now U.S. Pat. No. 10,233,473, which is a divisional application of U.S. application Ser. No. 15/265,460 filed on Sep. 14, 2016, now U.S. Pat. No. 10,081,824, which is a divisional application of U.S. application Ser. No. 14/238,431 filed on Aug. 23, 2012, now U.S. Pat. No. 9,476,036, which is a 35 U.S.C. § 371 national application of PCT/US2012/052163 filed Aug. 23, 2012, which claims priority or the benefit under 35 U.S.C. § 119 of U.S. Provisional Application No. 61/577,609 filed on Dec. 19, 2011 and U.S. Provisional Application No. 61/526,833 filed on Aug. 24, 2011, the contents of which are fully incorporated herein by reference.

STATEMENT AS TO RIGHTS TO INVENTIONS MADE UNDER FEDERALLY SPONSORED RESEARCH AND DEVELOPMENT

This invention was made with Government support under Cooperative Agreement DE-FC36-08GO18080 awarded by the Department of Energy. The government has certain rights in this invention.

REFERENCE TO A SEQUENCE LISTING

This application contains a Sequence Listing in computer readable form, which is incorporated herein by reference.

BACKGROUND OF THE INVENTION

Field of the Invention

The present invention relates to cellulolytic enzyme compositions; recombinant filamentous fungal host cells producing the cellulolytic enzyme compositions and methods of producing and using the compositions.

Description of the Related Art

Cellulose is a polymer of glucose linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol.

WO 2011/057140 discloses an *Aspergillus fumigatus* cellobiohydrolase I and gene thereof. WO 2011/057140 discloses an *Aspergillus fumigatus* cellobiohydrolase II and gene thereof. WO 2005/047499 discloses an *Aspergillus fumigatus* beta-glucosidase and gene thereof. WO 2006/078256 discloses *Aspergillus fumigatus* GH10 xylanases. WO 2011/057140 discloses an *Aspergillus fumigatus* beta-xylosidase and gene thereof. WO 2011/041397 discloses a *Penicillium* sp. GH61 polypeptide having cellulolytic enhancing activity and gene thereof.

There is a need in the art for new cellulolytic enzyme compositions that can deconstruct cellulosic material more efficiently.

The present invention provides cellulolytic enzyme compositions and methods of producing and using the compositions.

SUMMARY OF THE INVENTION

The present invention relates to enzyme compositions, comprising (i) an *Aspergillus fumigatus* cellobiohydrolase I; (ii) an *Aspergillus fumigatus* cellobiohydrolase II; (iii) an *Aspergillus fumigatus* beta-glucosidase or a variant thereof; and (iv) a *Penicillium* sp. GH61 polypeptide having cellulolytic enhancing activity; or homologs thereof.

The present invention also relates to recombinant filamentous fungal host cells, comprising polynucleotides encoding (i) an *Aspergillus fumigatus* cellobiohydrolase I; (ii) an *Aspergillus fumigatus* cellobiohydrolase II; (iii) an *Aspergillus fumigatus* beta-glucosidase or a variant thereof; and (iv) a *Penicillium* sp. GH61 polypeptide having cellulolytic enhancing activity; or homologs thereof.

The present invention also relates to methods of producing an enzyme composition, comprising: (a) cultivating a filamentous fungal host cell of the present invention under conditions conducive for production of the enzyme composition; and optionally (b) recovering the enzyme composition.

The present invention also relates to processes for degrading a cellulosic material, comprising: treating the cellulosic material with an enzyme composition of the present invention.

The present invention also relates to processes for producing a fermentation product, comprising: (a) saccharifying a cellulosic material with an enzyme composition of the present invention; (b) fermenting the saccharified cellulosic material with one or more (e.g., several) fermenting microorganisms to produce the fermentation product; and (c) recovering the fermentation product from the fermentation.

The present invention further relates to processes of fermenting a cellulosic material, comprising: fermenting the cellulosic material with one or more (e.g., several) fermenting microorganisms, wherein the cellulosic material is saccharified with an enzyme composition of the present invention.

DEFINITIONS

Figure 1:
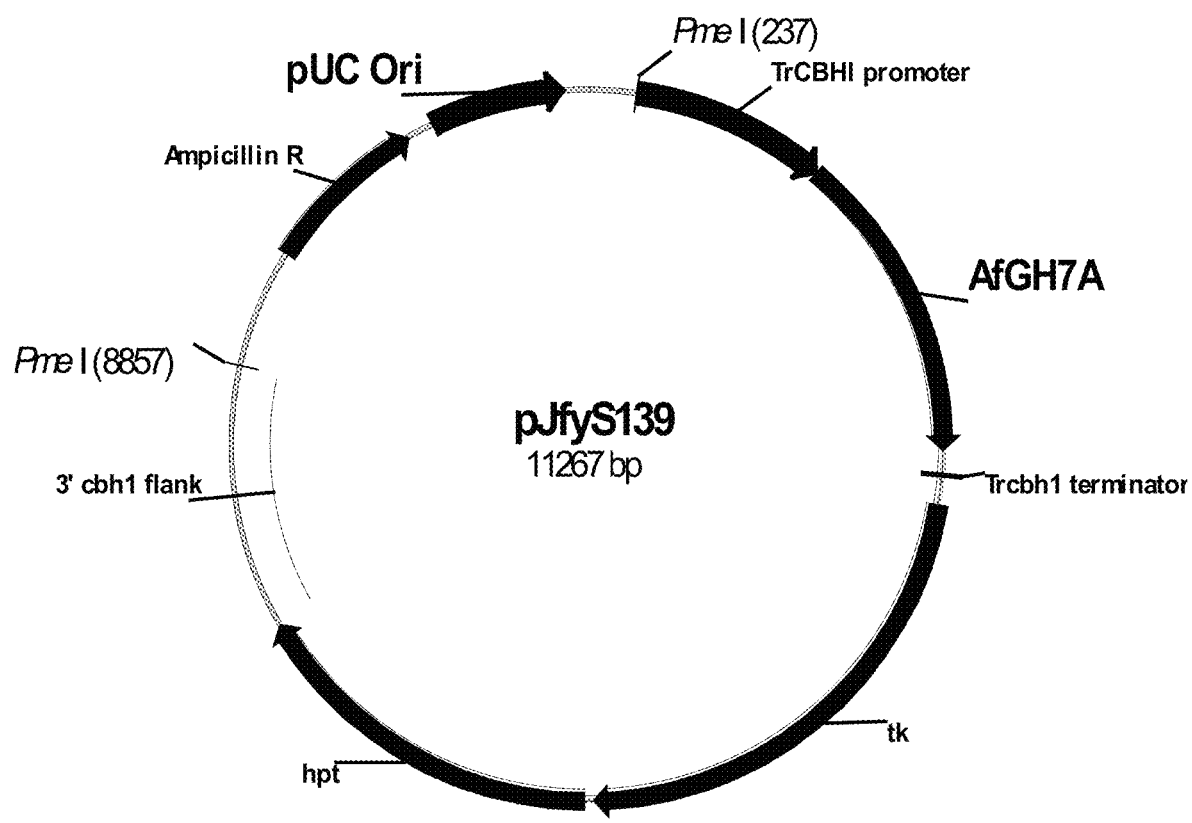
FIG. 1 shows a restriction map of plasmid pJfyS139.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more (e.g., several) alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 μmole of glucuronic or 4-O-methylglucuronic acid per minute at pH 5, 40° C.

Aspartic protease: The term "aspartic protease" means a protease that uses an aspartate residue(s) for catalyzing the hydrolysis of peptide bonds in peptides and proteins. Aspartic proteases are a family of protease enzymes that use an aspartate residue for catalytic hydrolysis of their peptide substrates. In general, they have two highly-conserved aspartates in the active site and are optimally active at acidic pH (Szecsi, 1992, *Scand. J. Clin. Lab. In vest.* Suppl. 210: 5-22). For purposes of the present invention, aspartic protease activity is determined according to the procedure described by Aikawa et al., 2001, *J. Biochem.* 129: 791-794.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20 (polyoxyethylene sorbitan monolaurate).

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 μmole of p-nitrophenolate anion produced per minute at 40° C., pH 5 from 1 mM p-nitrophenyl-beta-D-xyloside as substrate in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters*, 149: 152-156; van Tilbeurgh and Claeyssens, 1985, *FEBS Letters*, 187: 283-288; and Tomme et al., 1988, *Eur. J. Biochem.* 170: 575-581. In the present invention, the Tomme et al. method can be used to determine cellobiohydrolase activity.

Cellulolytic enzyme or cellulase: The term "cellulolytic enzyme" or "cellulase" means one or more (e.g., several)

enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wselogel et al., 1995, in *Handbook on Bioethanol* (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a polypeptide. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Flanking: The term "flanking" means DNA sequences extending on either side of a specific DNA sequence, locus, or gene. The flanking DNA is immediately adjacent to another DNA sequence, locus, or gene that is to be integrated into the genome of a filamentous fungal cell.

Fragment: The term "fragment" means a polypeptide having one or more (e.g., several) amino acids absent from the amino and/or carboxyl terminus of a mature polypeptide main; wherein the fragment has enzyme activity. In one aspect, a fragment contains at least 85%, e.g., at least 90% or at least 95% of the amino acid residues of the mature polypeptide of an enzyme.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Homologous 3' or 5' region: The term "homologous 3' region" means a fragment of DNA that is identical in sequence or has a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to a region in the genome and when combined with a homologous 5' region can target integration of a piece of DNA to a specific site in the genome by homologous recombination. The term "homologous 5' region" means a fragment of DNA that is identical in sequence to a region in the genome and when combined with a homologous 3' region can target integration of a piece of DNA to a specific site in the genome by homologous recombination. The homologous 5' and 3' regions must be linked in the genome which means they are on the same chromosome and within at least 200 kb of one another.

Homologous flanking region: The term "homologous flanking region" means a fragment of DNA that is identical or has a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to a region in the genome and is located immediately upstream or downstream of a specific site in the genome into which extracellular DNA is targeted for integration.

Homologous repeat: The term "homologous repeat" means a fragment of DNA that is repeated at least twice in the recombinant DNA introduced into a host cell and which can facilitate the loss of the DNA, i.e., selectable marker that is inserted between two homologous repeats, by homologous recombination. A homologous repeat is also known as a direct repeat.

Host cell: The term "host cell" means any cell type that is susceptible to transformation, transfection, transduction, or the like with a nucleic acid construct or expression vector comprising a polynucleotide encoding a polypeptide. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide of an *A. fumigatus* cellobiohydrolase I is amino acids 27 to 532 of SEQ ID NO: 2 based on the SignalP program (Nielsen et al., 1997, Protein Engineering 10: 1-6) that predicts amino acids 1 to 26 of SEQ ID NO: 2 are a signal peptide. In another aspect, the mature polypeptide of an *A. fumigatus* cellobiohydrolase II is amino acids 20 to 454 of SEQ ID NO: 4 based on the SignalP program that predicts amino acids 1 to 19 of SEQ ID NO: 4 are a signal peptide. In another aspect, the mature polypeptide of an *A. fumigatus* beta-glucosidase is amino acids 20 to 863 of SEQ ID NO: 6 based on the SignalP program that predicts amino acids 1 to 19 of SEQ ID NO: 6 are a signal peptide. In another aspect, the mature polypeptide of a *Penicillium* sp. GH61 polypeptide is amino acids 26 to 253 of SEQ ID NO: 8 based on the SignalP program that predicts amino acids 1 to 25 of SEQ ID NO: 8 are a signal peptide. In another aspect, the mature polypeptide of an *A. fumigatus* xylanase I is amino acids 18 to 364 of SEQ ID NO: 10 based on the SignalP program that predicts amino acids 1 to 17 of SEQ ID NO: 10 are a signal peptide. In another aspect, the mature polypeptide of an *A. fumigatus* xylanase II is amino acids 20 to 323 of SEQ ID NO: 12 based on the SignalP program that predicts amino acids 1 to 19 of SEQ ID NO: 12 are a signal peptide. In another aspect, the mature polypeptide of an *A. fumigatus* xylanase III is amino acids 20 to 397 of SEQ ID NO: 14 based on the SignalP program that predicts amino acids 1 to 19 of SEQ ID NO: 14 are a signal peptide. In another aspect, the mature polypeptide of an *A. fumigatus* beta-xylosidase is amino acids 21 to 792 of SEQ ID NO: 16 based on the SignalP program that predicts amino acids 1 to 20 of SEQ ID NO: 16 are a signal peptide.

In another aspect, the mature polypeptide of a *T. reesei* cellobiohydrolase I is amino acids 18 to 514 of SEQ ID NO: 18 based on the SignalP program that predicts amino acids 1 to 17 of SEQ ID NO: 18 are a signal peptide. In another aspect, the mature polypeptide of a *T. reesei* cellobiohydrolase II is amino acids 19 to 471 of SEQ ID NO: 20 based on the SignalP program that predicts amino acids 1 to 18 of SEQ ID NO: 20 are a signal peptide. In another aspect, the mature polypeptide of a *T. reesei* beta-glucosidase is amino acids 20 to 744 of SEQ ID NO: 22 based on the SignalP program that predicts amino acids 1 to 19 of SEQ ID NO: 22 are a signal peptide. In another aspect, the mature polypeptide of a *T. reesei* xylanase I is amino acids 20 to 229 of SEQ ID NO: 24 based on the SignalP program that predicts amino acids 1 to 19 of SEQ ID NO: 24 are a signal peptide. In another aspect, the mature polypeptide of a *T. reesei* xylanase II is amino acids 20 to 223 of SEQ ID NO: 26 based on the SignalP program that predicts amino acids 1 to 19 of SEQ ID NO: 26 are a signal peptide. In another aspect, the mature polypeptide of a *T. reesei* xylanase III is amino acids 17 to 347 of SEQ ID NO: 28 based on the SignalP program that predicts amino acids 1 to 16 of SEQ ID NO: 28 are a signal peptide. In another aspect, the mature polypeptide of a *T. reesei* beta-xylosidase is amino acids 21 to 797 of SEQ ID NO: 30 based on the SignalP program that predicts amino acids 1 to 20 of SEQ ID NO: 30 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having enzyme activity. In one aspect, the mature polypeptide coding sequence of an *A. fumigatus* cellobiohydrolase I is nucleotides 79 to 1596 of SEQ ID NO: 1 or the cDNA sequence thereof based on the SignalP program (Nielsen et al., 1997, supra) that predicts nucleotides 1 to 78 of SEQ ID NO: 1 encode a signal peptide. In another aspect, the mature polypeptide coding sequence of an *A. fumigatus* cellobiohydrolase II is nucleotides 58 to 1700 of SEQ ID NO: 3 or the cDNA sequence thereof based on the SignalP program that predicts nucleotides 1 to 57 of SEQ ID NO: 3 encode a signal peptide. In another aspect, the mature polypeptide coding sequence of an *A. fumigatus* beta-glucosidase is nucleotides 58 to 2580 of SEQ ID NO: 5 or the cDNA sequence thereof based on the SignalP program that predicts nucleotides 1 to 57 of SEQ ID NO: 5 encode a signal peptide. In another aspect, the mature polypeptide coding sequence of a *Penicillium* sp. GH61 polypeptide is nucleotides 76 to 832 of SEQ ID NO: 7 or the cDNA sequence thereof based on the SignalP program that predicts nucleotides 1 to 75 of SEQ ID NO: 7 encode a signal peptide. In another aspect, the mature polypeptide coding sequence of an *A. fumigatus* xylanase I is nucleotides 52 to 1145 of SEQ ID NO: 9 or the cDNA sequence thereof based on the SignalP program that predicts nucleotides 1 to 51 of SEQ ID NO: 9 encode a signal peptide. In another aspect, the mature polypeptide coding sequence of an *A. fumigatus* xylanase II is nucleotides 58 to 1400 of SEQ ID NO: 11 or the cDNA sequence thereof based on the SignalP program that predicts nucleotides 1 to 57 of SEQ ID NO: 11 encode a signal peptide. In another aspect, the mature polypeptide coding sequence of an *A. fumigatus* xylanase III is nucleotides 107 to 1415 of SEQ ID NO: 13 or the cDNA sequence thereof based on the SignalP program that predicts nucleotides 1 to 106 of SEQ ID NO: 13 encode a signal peptide. In another aspect, the mature polypeptide coding sequence of an *A. fumigatus* beta-xylosidase is nucleotides 61 to 2373 of SEQ ID NO: 15 or the cDNA sequence thereof based on the SignalP program that predicts nucleotides 1 to 60 of SEQ ID NO: 15 encode a signal peptide.

In another aspect, the mature polypeptide coding sequence of a *T. reesei* cellobiohydrolase I is nucleotides 52 to 1545 of SEQ ID NO: 17 or the cDNA sequence thereof based on the SignalP program that predicts nucleotides 1 to 51 of SEQ ID NO: 17 encode a signal peptide. In another aspect, the mature polypeptide coding sequence of a *T. reesei* cellobiohydrolase II is nucleotides 55 to 1608 of SEQ ID NO: 19 or the cDNA sequence thereof based on the SignalP program that predicts nucleotides 1 to 54 of SEQ ID NO: 19 encode a signal peptide. In another aspect, the mature polypeptide coding sequence of a *T. reesei* beta-glucosidase is nucleotides 58 to 2612 of SEQ ID NO: 21 or the cDNA sequence thereof based on the SignalP program that predicts nucleotides 1 to 57 of SEQ ID NO: 21 encode a signal peptide. In another aspect, the mature polypeptide coding sequence of a *T. reesei* xylanase I is nucleotides 58 to 749 of SEQ ID NO: 23 or the cDNA sequence thereof based on the SignalP program that predicts nucleotides 1 to 57 of SEQ ID NO: 23 encode a signal peptide. In another aspect, the mature polypeptide coding sequence of a *T. reesei* xylanase II is nucleotides 58 to 778 of SEQ ID NO: 25 or the cDNA sequence thereof based on the SignalP program that predicts nucleotides 1 to 57 of SEQ ID NO: 25 encode a signal peptide. In another aspect, the mature polypeptide coding sequence of a *T. reesei* xylanase III is nucleotides 49 to 1349 of SEQ ID NO: 27 or the cDNA sequence thereof based on the SignalP program that predicts nucleotides 1 to 48 of SEQ ID NO: 27 encode a signal peptide. In another aspect, the mature polypeptide coding sequence of a *T. reesei* beta-xylosidase is nucleotides 61 to 2391 of SEQ ID NO: 29 or the cDNA sequence thereof based on the SignalP program that predicts nucleotides 1 to 60 of SEQ ID NO: 29 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more (e.g., several) control sequences.

Operably linked: The term "operably linked" means a configuration in which a control sequence is placed at an appropriate position relative to the coding sequence of a polynucleotide such that the control sequence directs expression of the coding sequence.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Pretreated corn stover: The term "PCS" or "Pretreated Corn Stover" means a cellulosic material derived from corn stover by treatment with heat and dilute sulfuric acid, alkaline pretreatment, or neutral pretreatment.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having enzyme activity. In one aspect, a subsequence contains at least 85%, e.g., at least 90% or at least 95% of the nucleotides of the mature polypeptide coding sequence of an enzyme.

Subtilisin-like serine protease: The term "subtilisin-like serine protease" means a protease with a substrate specificity similar to subtilisin that uses a serine residue for catalyzing the hydrolysis of peptide bonds in peptides and proteins. Subtilisin-like proteases (subtilases) are serine proteases characterized by a catalytic triad of the three amino acids aspartate, histidine, and serine. The arrangement of these catalytic residues is shared with the prototypical subtilisin from *Bacillus licheniformis* (Siezen and Leunissen, 1997, *Protein Science* 6: 501-523). Subtilisin-like serine protease activity can be determined using a synthetic substrate, N-succinyl-L-Ala-L-Ala-L-Pro-L-Phe-p-nitroanilide (AAPF) (Bachem AG, Bubendorf, Switzerland) in 100 mM NaCl-100 mM MOPS pH 7.0 at 50° C. for 3 hours and then the absorbance at 405 nm is measured.

Targeted integration: The term "targeted integration" means the stable integration of extracellular DNA at a defined genomic locus.

Transformant: The term "transformant" means a cell which has taken up extracellular DNA (foreign, artificial or modified) and expresses the gene(s) contained therein.

Transformation: The term "transformation" means the introduction of extracellular DNA into a cell, i.e., the genetic alteration of a cell resulting from the direct uptake, incorporation and expression of exogenous genetic material (exogenous DNA) from its surroundings and taken up through the cell membrane(s).

Trypsin-like serine protease: The term "trypsin-like serine protease" means a protease with a substrate specificity similar to trypsin that uses a serine residue for catalyzing the hydrolysis of peptide bonds in peptides and proteins. For purposes of the present invention, trypsin-like serine protease activity is determined according to the procedure described by Dienes et al., 2007, *Enzyme and Microbial Technology* 40: 1087-1094.

Variant: The term "variant" means a polypeptide having enzyme activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune*, *FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

DETAILED DESCRIPTION OF THE INVENTION

The present invention relates to enzyme compositions, comprising (i) an *Aspergillus fumigatus* cellobiohydrolase I; (ii) an *Aspergillus fumigatus* cellobiohydrolase II; (iii) an *Aspergillus fumigatus* beta-glucosidase or a variant thereof; and (iv) a *Penicilllium* sp. (*emersonii*) GH61 polypeptide having cellulolytic enhancing activity; or homologs thereof.

In one aspect, the enzyme compositions further comprise an *Aspergillus fumigatus* xylanase, an *Aspergillus fumigatus* beta-xylosidase, or a combination thereof; or homologs thereof.

The enzyme compositions of the present invention are more efficient in the deconstruction of cellulosic material than a cellulolytic enzyme composition produced by *T. reesei*.

Enzyme Compositions

In the present invention, any *Aspergillus fumigatus* cellobiohydrolase I, *Aspergillus fumigatus* cellobiohydrolase II, an *Aspergillus fumigatus* beta-glucosidase or variant thereof, *Penicillium* sp. (*emersonii*) GH61 polypeptide having cellulolytic enhancing activity, *Aspergillus fumigatus* xylanase, or *Aspergillus fumigatus* beta-xylosidase, or homologs thereof, may be used.

In one aspect, the *Aspergillus fumigatus* cellobiohydrolase I or a homolog thereof is selected from the group consisting of: (i) a cellobiohydrolase I comprising or consisting of the mature polypeptide of SEQ ID NO: 2; (ii) a cellobiohydrolase I comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 2; (iii) a cellobiohydrolase I encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 1; and (iv) a cellobiohydrolase I encoded by a polynucleotide that hybridizes under at least high stringency conditions, e.g., very high stringency conditions, with the mature polypeptide coding sequence of SEQ ID NO: 1 or the full-length complement thereof.

In another aspect, the *Aspergillus fumigatus* cellobiohydrolase II or a homolog thereof is selected from the group consisting of: (i) a cellobiohydrolase II comprising or consisting of the mature polypeptide of SEQ ID NO: 4; (ii) a cellobiohydrolase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 4; (iii) a cellobiohydrolase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 3; and (iv) a cellobiohydrolase II encoded by a polynucleotide that hybridizes under at least high stringency conditions, e.g., very high stringency conditions, with the mature polypeptide coding sequence of SEQ ID NO: 3 or the full-length complement thereof.

In another aspect, the *Aspergillus fumigatus* beta-glucosidase or a homolog thereof is selected from the group consisting of: (i) a beta-glucosidase comprising or consisting of the mature polypeptide of SEQ ID NO: 6; (ii) a beta-glucosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 6; (iii) a beta-glucosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 5; and (iv) a beta-glucosidase encoded by a polynucleotide that hybridizes under at least high stringency conditions, e.g., very high stringency conditions, with the mature polypeptide coding sequence of SEQ ID NO: 5 or the full-length complement thereof.

In another aspect, the *Penicillium* sp. (*emersonii*) GH61 polypeptide having cellulolytic enhancing activity or a homolog thereof is selected from the group consisting of: (i)

a GH61 polypeptide having cellulolytic enhancing activity comprising or consisting of the mature polypeptide of SEQ ID NO: 8; (ii) a GH61 polypeptide having cellulolytic enhancing activity comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 8; (iii) a GH61 polypeptide having cellulolytic enhancing activity encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 7; and (iv) a GH61 polypeptide having cellulolytic enhancing activity encoded by a polynucleotide that hybridizes under at least high stringency conditions, e.g., very high stringency conditions, with the mature polypeptide coding sequence of SEQ ID NO: 7 or the full-length complement thereof.

In another aspect, the *Aspergillus fumigatus* xylanase or a homolog thereof is selected from the group consisting of: (i) a xylanase comprising or consisting of the mature polypeptide of SEQ ID NO: 10, SEQ ID NO: 12, or SEQ ID NO: 14; (ii) a xylanase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 10, SEQ ID NO: 12, or SEQ ID NO: 14; (iii) a xylanase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 9, SEQ ID NO: 11, or SEQ ID NO: 13; and (iv) a xylanase encoded by a polynucleotide that hybridizes under at least high stringency conditions, e.g., very high stringency conditions, with the mature polypeptide coding sequence of SEQ ID NO: 9, SEQ ID NO: 11, or SEQ ID NO: 13; or the full-length complement thereof.

In another aspect, the *Aspergillus fumigatus* beta-xylosidase or a homolog thereof is selected from the group consisting of: (i) a beta-xylosidase comprising or consisting of the mature polypeptide of SEQ ID NO: 16; (ii) a beta-xylosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 16; (iii) a beta-xylosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 15; and (iv) a beta-xylosidase encoded by a polynucleotide that hybridizes under at least high stringency conditions, e.g., very high stringency conditions, with the mature polypeptide coding sequence of SEQ ID NO: 15 or the full-length complement thereof.

The polynucleotide of SEQ ID NO: 1, 3, 5, 7, 9, 11, 13, or 15, or a subsequence thereof, as well as the polypeptide of SEQ ID NO: 2, 4, 6, 8, 10, 12, 14, or 16, or a fragment thereof, may be used to design nucleic acid probes to identify and clone DNA encoding enzymes according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library may be screened for DNA that hybridizes with the probes described above and encodes an enzyme. Genomic or other DNA may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, 3, 5, 7, 9, 11, 13, or 15, or a subsequence thereof, the carrier material is used in a Southern blot.

For purposes of the present invention, hybridization indicates that the polynucleotide hybridizes to a labeled nucleic acid probe corresponding to (i) SEQ ID NO: 1, 3, 5, 7, 9, 11, 13, or 15; (ii) the mature polypeptide coding sequence of SEQ ID NO: 1, 3, 5, 7, 9, 11, 13, or 15, or 21; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is SEQ ID NO: 1, 3, 5, 7, 9, 11, 13, or 15, or the mature polypeptide coding sequence thereof. In another aspect, the nucleic acid probe is a polynucleotide that encodes the polypeptide of SEQ ID NO: 2, 4, 6, 8, 10, 12, 14, or 16; the mature polypeptide thereof; or a fragment thereof.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be an allelic or species variant of the polypeptide encoding region of the polynucleotide.

A protein engineered variant of an enzyme above (or protein) may also be used.

In one aspect, the variant is an *Aspergillus fumigatus* beta-glucosidase variant. In another aspect, the *A. fumigatus* beta-glucosidase variant comprises a substitution at one or more (several) positions corresponding to positions 100, 283, 456, and 512 of SEQ ID NO: 6, wherein the variant has beta-glucosidase activity.

In an embodiment, the variant has sequence identity of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100%, to the amino acid sequence of the parent beta-glucosidase.

In another embodiment, the variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100%, sequence identity to the mature polypeptide of SEQ ID NO: 6.

For purposes of the present invention, the mature polypeptide disclosed in SEQ ID NO: 6 is used to determine the corresponding amino acid residue in another beta-glucosidase. The amino acid sequence of another beta-glucosidase is aligned with the mature polypeptide disclosed in SEQ ID NO: 6, and based on the alignment, the amino acid position number corresponding to any amino acid residue in the mature polypeptide disclosed in SEQ ID NO: 6 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. Identification of the corresponding amino acid residue in another beta-glucosidase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

In one aspect, a variant comprises a substitution at one or more (several) positions corresponding to positions 100, 283, 456, and 512. In another aspect, a variant comprises a substitution at two positions corresponding to any of positions 100, 283, 456, and 512. In another aspect, a variant comprises a substitution at three positions corresponding to any of positions 100, 283, 456, and 512. In another aspect, a variant comprises a substitution at each position corresponding to positions 100, 283, 456, and 512.

In another aspect, the variant comprises or consists of a substitution at a position corresponding to position 100. In another aspect, the amino acid at a position corresponding to position 100 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp. In another aspect, the variant comprises or consists of the substitution F100D of the mature polypeptide of SEQ ID NO: 6.

In another aspect, the variant comprises or consists of a substitution at a position corresponding to position 283. In another aspect, the amino acid at a position corresponding to position 283 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gly In another aspect, the variant comprises or consists of the substitution S283G of the mature polypeptide of SEQ ID NO: 6.

In another aspect, the variant comprises or consists of a substitution at a position corresponding to position 456. In another aspect, the amino acid at a position corresponding to position 456 is substituted with Ala, Arg, Asn, Asp, Cys, Gln, Glu, Gly, His, Ile, Leu, Lys, Met, Phe, Pro, Ser, Thr, Trp, Tyr, or Val, preferably with Glu. In another aspect, the variant comprises or consists of the substitution N456E of the mature polypeptide of SEQ ID NO: 6.

In another aspect, the variant comprises or consists of a substitution at a position corresponding to position 512. In another aspect, the amino acid at a position corresponding to position 512 is substituted with Ala, Arg, Asn, Asp, Cys, Gln, Glu, Gly, His, Ile, Leu, Lys, Met, Phe, Pro, Ser, Thr, Trp, Tyr, or Val, preferably with Tyr. In another aspect, the variant comprises or consists of the substitution F512Y of the mature polypeptide of SEQ ID NO: 6.

In another aspect, the variant comprises or consists of a substitution at positions corresponding to positions 100 and 283, such as those described above.

In another aspect, the variant comprises or consists of substitutions at positions corresponding to positions 100 and 456, such as those described above.

In another aspect, the variant comprises or consists of substitutions at positions corresponding to positions 100 and 512, such as those described above.

In another aspect, the variant comprises or consists of substitutions at positions corresponding to positions 283 and 456, such as those described above.

In another aspect, the variant comprises or consists of substitutions at positions corresponding to positions 283 and 512, such as those described above.

In another aspect, the variant comprises or consists of substitutions at positions corresponding to positions 456 and 512, such as those described above.

In another aspect, the variant comprises or consists of substitutions at positions corresponding to positions 100, 283, and 456, such as those described above.

In another aspect, the variant comprises or consists of substitutions at positions corresponding to positions 100, 283, and 512, such as those described above.

In another aspect, the variant comprises or consists of substitutions at positions corresponding to positions 100, 456, and 512, such as those described above.

In another aspect, the variant comprises or consists of substitutions at positions corresponding to positions 283, 456, and 512, such as those described above.

In another aspect, the variant comprises or consists of substitutions at positions corresponding to positions 100, 283, 456, and 512, such as those described above.

In another aspect, the variant comprises or consists of one or more (several) substitutions selected from the group consisting of G142S, Q183R, H266Q, and D703G.

In another aspect, the variant comprises or consists of the substitutions F100D+S283G of the mature polypeptide of SEQ ID NO: 6.

In another aspect, the variant comprises or consists of the substitutions F100D+N456E of the mature polypeptide of SEQ ID NO: 6.

In another aspect, the variant comprises or consists of the substitutions F100D+F512Y of the mature polypeptide of SEQ ID NO: 6.

In another aspect, the variant comprises or consists of the substitutions S283G+N456E of the mature polypeptide of SEQ ID NO: 6.

In another aspect, the variant comprises or consists of the substitutions S283G+F512Y of the mature polypeptide of SEQ ID NO: 6.

In another aspect, the variant comprises or consists of the substitutions N456E+F512Y of the mature polypeptide of SEQ ID NO: 6.

In another aspect, the variant comprises or consists of the substitutions F100D+S283G+N456E of the mature polypeptide of SEQ ID NO: 6.

In another aspect, the variant comprises or consists of the substitutions F100D+S283G+F512Y of the mature polypeptide of SEQ ID NO: 6.

In another aspect, the variant comprises or consists of the substitutions F100D+N456E+F512Y of the mature polypeptide of SEQ ID NO: 6.

In another aspect, the variant comprises or consists of the substitutions S283G+N456E+F512Y of the mature polypeptide of SEQ ID NO: 6.

In another aspect, the variant comprises or consists of the substitutions F100D+S283G+N456E+F512Y of the mature polypeptide of SEQ ID NO: 6.

The variants may consist of 720 to 863 amino acids, e.g., 720 to 739, 740 to 759, 760 to 779, 780 to 799, 800 to 819, 820 to 839, and 840 to 863 amino acids.

The variants may further comprise an alteration at one or more (several) other positions.

The enzyme composition may further comprise one or more (e.g., several) enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

One or more (e.g., several) of the enzymes may be wild-type proteins, recombinant proteins, or a combination of wild-type proteins and recombinant proteins. For example, one or more (e.g., several) enzymes may be native proteins of a cell, which is used as a host cell to express recombinantly the enzyme composition.

Examples of bacterial endoglucanases that can be used in the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention, include, but are not limited to, a *Trichoderma reesei* endoglucanase I (Penttila et al., 1986, Gene 45: 253-263, *Trichoderma reesei* Cel7B endoglucanase I (GENBANK™ accession no. M15665), *Trichoderma reesei* endoglucanase II (Saloheimo, et al., 1988, Gene 63:11-22), *Trichoderma reesei* Cel5A endoglucanase II (GENBANK™ accession no. M19373), *Trichoderma reesei* endoglucanase III (Okada et al., 1988, *Appl. Environ. Microbiol.* 64: 555-563, GENBANK™ accession no. AB003694), *Trichoderma reesei* endoglucanase V (Saloheimo et al., 1994, *Molecular Microbiology* 13: 219-228, GENBANK™ accession no. Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Erwinia carotovara* endoglucanase (Saarilahti et al., 1990, *Gene* 90: 9-14), *Fusarium oxysporum* endoglucanase (GENBANK™ accession no. L29381), *Humicola grisea* var. *thermoidea* endoglucanase (GENBANK™ accession no. AB003107), *Melanocarpus albomyces* endoglucanase (GENBANK™ accession no. MAL515703), *Neurospora crassa* endoglucanase (GENBANK™ accession no. XM_324477), *Humicola insolens* endoglucanase V, *Myceliophthora thermophila* CBS 117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris* NRRL 8126 CEL7C endoglucanase, *Thielavia terrestris* NRRL 8126 CEL7E endoglucanase, *Thielavia terrestris* NRRL 8126 CEL7F endoglucanase, *Cladorrhinum foecundissimum* ATCC 62373 CEL7A endoglucanase, and *Trichoderma reesei* strain No. VTT-D-80133 endoglucanase (GENBANK™ accession no. M15665).

In one aspect, the enzyme composition further comprises a *Trichoderma* endoglucanase I. In another aspect, the enzyme composition further comprises a *Trichoderma reesei* endoglucanase I. In another aspect, the enzyme composition further comprises a *Trichoderma reesei* Cel7B endoglucanase I (GENBANK™ accession no. M15665). In another aspect, the *Trichoderma reesei* endoglucanase I is native to the host cell. In another aspect, the *Trichoderma reesei* endoglucanase I is the mature polypeptide of SEQ ID NO: 90.

In another aspect, the enzyme composition further comprises a *Trichoderma* endoglucanase II. In another aspect, the enzyme composition further comprises a *Trichoderma reesei* endoglucanase II. In another aspect, the enzyme composition further comprises a *Trichoderma reesei* Cel5A endoglucanase II (GENBANK™ accession no. M19373). In another aspect, the *Trichoderma reesei* endoglucanase II is native to the host cell. In another aspect, the *Trichoderma reesei* endoglucanase I is the mature polypeptide of SEQ ID NO: 92.

The compositions may be prepared in accordance with methods known in the art and may be in the form of a liquid or a dry composition. The compositions may be stabilized in accordance with methods known in the art.

The enzyme composition may also be a fermentation broth formulation or a cell composition.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Host Cells

The present invention also relates to recombinant filamentous fungal host cells, comprising polynucleotides encoding (i) an *Aspergillus fumigatus* cellobiohydrolase I; (ii) an *Aspergillus fumigatus* cellobiohydrolase II; (iii) an *Aspergillus fumigatus* beta-glucosidase or a variant thereof; and (iv) a *Penicilllium* sp. GH61 polypeptide having cellulolytic enhancing activity; or homologs thereof. The term "host cell" encompasses any progeny of a parent cell that is not identical to the parent cell due to mutations that occur during replication.

The host cell may be any filamentous fungal cell useful in the recombinant production of an enzyme or protein.

"Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phiebia*, *Piromyces*, *Pleurotus*, *Schizophyllum*, *Talaromyces*, *Thermoascus*, *Thielavia*, *Tolypocladium*, *Trametes*, or *Trichoderma* cell.

For example, the filamentous fungal host cell may be an *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Bjerkandera adusta*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Coprinus cinereus*, *Coriolus hirsutus*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium suiphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phiebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

In one aspect, the filamentous fungal cell is any *Trichoderma* cell useful in the recombinant production of an enzyme or protein. For example, the *Trichoderma* cell may be a *Trichoderma harzianum, Trichoderma koningii, Trichoderma longibrachiatum, Trichoderma reesei*, or *Trichoderma viride* cell. In another aspect, the *Trichoderma* cell is a *Trichoderma harzianum* cell. In another aspect, the *Trichoderma* cell is a *Trichoderma koningii* cell. In another aspect, the *Trichoderma* cell is a *Trichoderma longibrachiatum* cell. In another aspect, the *Trichoderma* cell is a *Trichoderma reesei* cell. In another aspect, the *Trichoderma* cell is a *Trichoderma viride* cell.

In another aspect, the *Trichoderma reesei* cell is *Trichoderma reesei* RutC30. In another aspect, the *Trichoderma reesei* cell is *Trichoderma reesei* TV10. In another aspect, the *Trichoderma reesei* cell is a mutant of *Trichoderma reesei* RutC30. In another aspect, the *Trichoderma reesei* cell is mutant of *Trichoderma reesei* TV10. In another aspect, the *Trichoderma reesei* cell is a morphological mutant of *Trichoderma reesei*. See, for example, WO 97/26330, which is incorporated herein by reference in its entirety.

A *Trichoderma* cell may be transformed by a process involving protoplast formation, transformation of the protoplasts, and regeneration of the cell wall in a manner known per se. Suitable procedures for transformation of *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422.

One or more (e.g., several) native cellulase and/or hemicellulase genes may be inactivated in the *Trichoderma* host cell by disrupting or deleting the genes, or a portion thereof, which results in the mutant cell producing less or none of the cellulase and/or hemicellulase than the parent cell when cultivated under the same conditions. In one aspect, the one or more (e.g., several) cellulase genes encode enzymes selected from the group consisting of cellobiohydrolase I, cellobiohydrolase II, endoglucanase I, endoglucanase II, beta-glucosidase, and swollenin. In another aspect, the one or more (e.g., several) hemicellulase genes encode enzymes selected from the group consisting of xylanase I, xylanase II, xylanase III, and beta-xylosidase. In another aspect, the one or more (e.g., several) hemicellulase genes encode enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, and a mannosidase.

The mutant cell may be constructed by reducing or eliminating expression of a polynucleotide encoding a *Trichoderma* cellulase or hemicellulase using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may also be accomplished by insertion, substitution, or deletion of one or more (e.g., several) nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

Modification or inactivation of the polynucleotide may also be accomplished by inhibiting expression of an enzyme encoded by the polynucleotide in a cell by administering to the cell or expressing in the cell a double-stranded RNA (dsRNA) molecule, wherein the dsRNA comprises a subsequence of a polynucleotide encoding the enzyme. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA for inhibiting transcription. In another preferred aspect, the dsRNA is micro RNA for inhibiting translation. In another aspect, the double-stranded RNA (dsRNA) molecules comprise a portion of the mature polypeptide coding sequence of SEQ ID NO: 17, SEQ ID NO: 19, SEQ ID NO: 21, SEQ ID NO: 23, SEQ ID NO: 25, SEQ ID NO: 27, and/or SEQ ID NO: 29 for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs can be used in gene-silencing to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

In one aspect, the *Trichoderma* cellobiohydrolase I or a homolog thereof is selected from the group consisting of: (i) a cellobiohydrolase I comprising or consisting of the mature polypeptide of SEQ ID NO: 18; (ii) a cellobiohydrolase I comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 18; (iii) a cellobiohydrolase I encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 17; and (iv) a cellobiohydrolase I encoded by a polynucleotide that hybridizes under at least high stringency conditions, e.g., very high stringency conditions, with the mature polypeptide coding sequence of SEQ ID NO: 17 or the full-length complement thereof.

In another aspect, the *Trichoderma* cellobiohydrolase II or a homolog thereof is selected from the group consisting of: (i) a cellobiohydrolase II comprising or consisting of the mature polypeptide of SEQ ID NO: 20; (ii) a cellobiohydrolase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 20; (iii) a cellobiohydrolase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 19; and (iv) a cellobiohydrolase II encoded by a polynucleotide that hybridizes under at least high stringency conditions, e.g., very high stringency conditions, with the mature polypeptide coding sequence of SEQ ID NO: 19 or the full-length complement thereof.

In another aspect, the *Trichoderma* beta-glucosidase or a homolog thereof is selected from the group consisting of: (i) a beta-glucosidase comprising or consisting of the mature polypeptide of SEQ ID NO: 22; (ii) a beta-glucosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 22; (iii) a beta-glucosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 21; and (iv) a beta-glucosidase encoded by a polynucleotide that hybridizes under at least high stringency conditions, e.g., very high stringency conditions, with the mature polypeptide coding sequence of SEQ ID NO: 21 or the full-length complement thereof.

In another aspect, the *Trichoderma* xylanase or a homolog thereof is selected from the group consisting of: (i) a xylanase comprising or consisting of the mature polypeptide of SEQ ID NO: 24, SEQ ID NO: 26, or SEQ ID NO: 28; (ii) a xylanase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 24, SEQ ID NO: 26, or SEQ ID NO: 28; (iii) a xylanase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 23, SEQ ID NO: 25, or SEQ ID NO: 27; and (iv) a xylanase encoded by a polynucleotide that hybridizes under at least high stringency conditions, e.g., very high stringency conditions, with the mature polypeptide coding sequence of SEQ ID NO: 23, SEQ ID NO: 25, or SEQ ID NO: 27; or the full-length complement thereof.

In another aspect, the *Trichoderma* beta-xylosidase or a homolog thereof is selected from the group consisting of: (i) a beta-xylosidase comprising or consisting of the mature polypeptide of SEQ ID NO: 30; (ii) a beta-xylosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 30; (iii) a beta-xylosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 29; and (iv) a beta-xylosidase encoded by a polynucleotide that hybridizes under at least high stringency conditions, e.g., very high stringency conditions, with the mature polypeptide coding sequence of SEQ ID NO: 29 or the full-length complement thereof.

In one aspect, a *Trichoderma* cellobiohydrolase I gene is inactivated. In another aspect, a *Trichoderma* cellobiohydrolase II gene is inactivated. In another aspect, a *Trichoderma* beta-glucosidase gene is inactivated. In another aspect, a *Trichoderma* xylanase gene is inactivated. In another aspect, a *Trichoderma* beta-xylosidase gene is inactivated.

In another aspect, a *Trichoderma* cellobiohydrolase I gene and a *Trichoderma* cellobiohydrolase II gene are inactivated.

In another aspect, two or more (e.g., several) genes selected from the group consisting of cellobiohydrolase I, cellobiohydrolase II, beta-glucosidase, xylanase I, xylanase II, xylanase III, and beta-xylosidase are inactivated. In another aspect, three or more (e.g., several) genes selected from the group consisting of cellobiohydrolase I, cellobiohydrolase II, beta-glucosidase, xylanase I, xylanase II, xylanase III, and beta-xylosidase genes are inactivated. In another aspect, four or more (e.g., several) genes selected from the group consisting of cellobiohydrolase I, cellobiohydrolase II, beta-glucosidase, xylanase I, xylanase II, xylanase III, and beta-xylosidase genes are inactivated. In another aspect, five or more (e.g., several) genes selected from the group consisting of cellobiohydrolase I, cellobiohydrolase II, beta-glucosidase, xylanase I, xylanase II, xylanase III, and beta-xylosidase genes are inactivated. In another aspect, six or more (e.g., several) genes selected from the group consisting of cellobiohydrolase I, cellobiohydrolase II, beta-glucosidase, xylanase I, xylanase II, xylanase III, and beta-xylosidase genes are inactivated.

In another aspect, the cellobiohydrolase I, cellobiohydrolase II, beta-glucosidase, xylanase I, xylanase II, xylanase III, and beta-xylosidase genes are inactivated.

In another aspect, one or more (e.g., several) protease genes are inactivated. In another aspect, the one or more (e.g., several) protease genes are subtilisin-like serine protease, aspartic protease, and trypsin-like serine protease genes as described in WO 2011/075677, which is incorporated herein by reference in its entirety.

Nucleic Acid Constructs

Nucleic acid constructs comprising a polynucleotide encoding an enzyme or protein can be constructed by operably linking one or more (e.g., several) control sequences to the polynucleotide to direct the expression of the coding sequence in a filamentous fungal host cell under conditions compatible with the control sequences. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a filamentous fungal host cell for expression of a polynucleotide encoding an enzyme or protein. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147, which is incorporated herein in its entirety.

The control sequence may also be a transcription terminator, which is recognized by a filamentous fungal host cell to terminate transcription. The terminator is operably linked to the 3'-terminus of the polynucleotide encoding the polypeptide. Any terminator that is functional in the host cell may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

The control sequence may also be a leader, a nontranslated region of an mRNA that is important for translation by a filamentous fungal host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

The control sequence may also be a polyadenylation sequence, a sequence operably linked to the 3'-terminus of the polynucleotide and, when transcribed, is recognized by a filamentous fungal host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, *Fusarium oxysporum* trypsin-like protease, *Trichoderma reesei* cellobiohydrolase I, *Trichoderma reesei* cellobiohydrolase II, and *Trichoderma reesei* endoglucanase V.

The control sequence may also be a signal peptide coding region that encodes a signal peptide linked to the N-terminus of a polypeptide and directs the polypeptide into a cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, *Rhizomucor miehei* aspartic proteinase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, and *Trichoderma reesei* endoglucanase V.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Myceliophthora thermophila* laccase (WO 95/33836) and *Rhizomucor miehei* aspartic proteinase.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of a filamentous fungal host cell. Examples of regulatory sequences are those that cause expression of the gene to be turned on or off in response to a chemical or physical stimulus, including the presence of a regulatory compound. Regulatory sequences include the *Aspergillus niger* glucoamylase promoter, *Aspergillus oryzae* TAKA alpha-amylase promoter, *Aspergillus oryzae* glucoamylase promoter, *Trichoderma reesei* cellobiohydrolase I promoter, and *Trichoderma reesei* cellobiohydrolase II promoter. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

Recombinant expression vectors can be constructed comprising a polynucleotide encoding an enzyme or protein, a promoter, a terminator, and transcriptional and translational stop signals. The various nucleotide and control sequences may be joined together to produce a recombinant expression vector that may include one or more (e.g., several) convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (e.g., several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes. Examples of bacterial selectable markers are markers that confer antibiotic resistance such as ampicillin, chloramphenicol, kanamycin, neomycin, spectinomycin, or tetracycline resistance.

The selectable marker may be a dual selectable marker system as described in WO 2010/039889 A2, which is incorporated herein by reference in its entirety. In one aspect, the selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in a filamentous fungal host cell. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication useful in a filamentous fungal host cell are AMA1 and ANSI (Gems et al., 1991, Gene 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide may be inserted into a filamentous fungal host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors are well known to one skilled in the art (see, e.g., Sambrook et al., 1989, supra).

Methods of Production

The present invention also relates to methods of producing an enzyme composition, comprising: (a) cultivating a filamentous fungal host cell of the present invention under conditions conducive for production of the enzyme composition; and optionally (b) recovering the enzyme composition.

The filamentous fungal host cells are cultivated in a nutrient medium suitable for production of the enzyme composition using methods known in the art. For example, the cell may be cultivated by shake flask cultivation, or small-scale or large-scale fermentation (including continuous, batch, fed-batch, or solid state fermentations) in laboratory or industrial fermentors in a suitable medium and under conditions allowing the enzymes to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection).

The enzymes may be detected using methods known in the art that are specific for the enzyme. These detection methods include, but are not limited to, use of specific antibodies, formation of an enzyme product, or disappearance of an enzyme substrate. For example, an enzyme assay may be used to determine activity.

The enzymes may be recovered using methods known in the art. For example, the enzyme may be recovered from the nutrient medium by conventional procedures including, but not limited to, collection, centrifugation, filtration, extraction, spray-drying, evaporation, or precipitation. In one aspect, the whole fermentation broth is recovered.

The enzymes may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

Uses

The present invention is also directed to the following processes for using an enzyme composition of the present invention.

The present invention also relates to processes for degrading a cellulosic material, comprising: treating the cellulosic material with an enzyme composition of the present invention. In one aspect, the processes further comprise recovering the degraded or converted cellulosic material. Soluble products of degradation or conversion of the cellulosic material can be separated from insoluble cellulosic material using a method known in the art such as, for example, centrifugation, filtration, or gravity settling.

The present invention also relates to processes of producing a fermentation product, comprising: (a) saccharifying a cellulosic material with an enzyme composition of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition of the present invention. In one aspect, the fermenting of the cellulosic material produces a fermentation product. In another aspect, the processes further comprise recovering the fermentation product from the fermentation.

The processes of the present invention can be used to saccharify the cellulosic material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic material typically involves pretreatment, enzymatic hydrolysis (saccharification), and fermentation.

The processing of the cellulosic material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include fluidized bed, upflow blanket, immobilized, and extruder type reactors for hydrolysis and/or fermentation.

Pretreatment. In practicing the processes of the present invention, any pretreatment process known in the art can be used to disrupt plant cell wall components of the cellulosic material (Chandra et al., 2007, Substrate pretreatment: The key to effective enzymatic hydrolysis of lignocellulosics?, *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.*

59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt %, e.g., 20-70 wt % or 30-60 wt %, such as around 40 wt %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification. In the hydrolysis step, also known as saccharification, the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition of the present invention.

Enzymatic hydrolysis is preferably carried out in a suitable aqueous environment under conditions that can be readily determined by one skilled in the art. In one aspect, hydrolysis is performed under conditions suitable for the activity of the enzyme(s), i.e., optimal for the enzyme(s). The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

In the processes of the present invention, the enzyme composition of the present invention can be added prior to or during fermentation, e.g., during saccharification or during or after propagation of the fermenting microorganism(s).

The enzyme composition of the present invention may be in any form suitable for use, such as, for example, a crude fermentation broth with or without cells removed, a cell lysate with or without cellular debris, a semi-purified or purified enzyme preparation, or a *Trichoderma* host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amount of *Aspergillus fumigatus* cellulases or hemicellulases depends on several factors including, but not limited to, the mixture of component cellulolytic and/or hemicellulolytic enzymes, the cellulosic material, the concentration of cellulosic material, the pretreatment(s) of the cellulosic material, temperature, time, pH, and inclusion of fermenting organism (e.g., yeast for Simultaneous Saccharification and Fermentation).

In one aspect, an effective amount of cellulolytic or hemicellulolytic enzyme to the cellulosic material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material.

In another aspect, the GH61 polypeptide having cellulolytic enhancing activity is used in the presence of a soluble activating divalent metal cation according to WO 2008/151043, e.g., manganese sulfate.

In another aspect, a GH61 polypeptide having cellulolytic enhancing activity is used in the presence of a dioxy compound, a bicyclic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1, 2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of the bicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothienopyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl)furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more (e.g., several) nitrogen atoms. In one aspect, the nitrogen-containing compound comprises an amine, imine, hydroxylamine, or nitroxide moiety. Non-limiting examples of the nitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more (e.g., several) sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

Fermentation. The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida*, *Kluyveromyces*, and *Saccharomyces*, e.g., *Candida sonorensis*, *Kluyveromyces marxianus*, and *Saccharomyces cerevisiae*.

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans; Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis*, and *C. scehatae; Clostridium*, such as *C. acetobutylicum, C. thermocellum*, and *C. phytofermentans; E. coli*, especially *E. coli* strains that have been genetically modified to improve the yield of ethanol; *Geobacillus* sp.; *Hansenula*, such as *Hansenula anomala; Klebsiella*, such as *K. oxytoca; Kluyveromyces*, such as *K. marxianus, K. lactis, K. thermotolerans*, and *K. fragilis; Schizosaccharomyces*, such as *S. pombe; Thermoanaerobacter*, such as *Thermoanaerobacter saccharolyticum*; and *Zymomonas*, such as *Zymomonas mobilis*.

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida* blankii. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida* scehatae. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Saccharomyces* spp. In another more preferred aspect, the yeast is *Saccharomyces cerevisiae*. In another more preferred aspect, the yeast is *Saccharomyces distaticus*. In another more preferred aspect, the yeast is *Saccharomyces uvarum*.

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacillus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis*, *Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation products: A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more (e.g., several) hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, Water Science and Technology 36 (6-7): 41-47; and Gunaseelan V. N. in *Biomass and Bioenergy*, Vol. 13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more (e.g., several) ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery. The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

The present invention is further described by the following examples that should not be construed as limiting the scope of the invention.

EXAMPLES

Strains

*Trichoderma reesei* strain 981-O-8 (D4) is a mutagenized strain of *Trichoderma reesei* RutC30 (ATCC 56765; Montenecourt and Eveleigh, 1979, *Adv. Chem. Ser.* 181: 289-301).

*Trichoderma reesei* strain AgJg115-104-7B1 (PCT/US2010/061105; WO 2011/075677) is a *T. reesei* ku70-derivative of strain 981-O-8 (D4).

Media and Buffer Solutions

2XYT plus ampicillin plates were composed of 16 g of tryptone, 10 g of yeast extract, 5 g of sodium chloride, 15 g of Bacto agar, and deionized water to 1 liter. One ml of a 100 mg/ml solution of ampicillin was added after the autoclaved medium was cooled to 55° C.

SOC medium was composed of 20 g of Bacto-tryptone, 5 g of Bacto yeast extract, 0.5 g of NaCl, 2.5 ml of 1 M KCl, and deionized water to 1 liter. The pH was adjusted to 7.0 with 10 N NaOH before autoclaving. Then 20 ml of sterile 1 M glucose was added immediately before use.

COVE salt solution was composed of 26 g of KCl, 26 g of $MgSO_4.7H_2O$, 76 g of $KH_2PO_4$, 50 ml of COVE trace metals solution, and deionized water to 1 liter.

COVE trace metals solution was composed of 0.04 g of $NaB_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, 10 g of $ZnSO_4.7H_2O$, and deionized water to 1 liter.

COVE plates were composed of 342.3 g of sucrose, 20 ml of COVE salt solution, 10 ml of 1 M acetamide, 10 ml of 1.5 M CsCl, 25 g of Noble agar (Difco), and deionized water to 1 liter.

COVE2 plates were composed of 30 g of sucrose, 20 ml of COVE salt solution, 10 ml of 1 M acetamide, 25 g of Noble agar (Difco), and deionized water to 1 liter.

*Trichoderma* trace metals solution was composed of 216 g of $FeCl_3.6H_2O$, 58 g of $ZnSO_4.7H_2O$, 27 g of $MnSO_4.H_2O$, 10 g of $CuSO_4.5H_2O$, 2.4 g of $H_3BO_3$, 336 g of citric acid, and deionized water to 1 liter.

CIM medium was composed of 20 g of cellulose, 10 g of corn steep solids, 1.45 g of $(NH_4)_2SO_4$, 2.08 g of $KH_2PO_4$, 0.28 g of $CaCl_2$, 0.42 g of $MgSO_4.7H_2O$, 0.42 ml of *Trichoderma* trace metals solution, 1-2 drops of antifoam, and deionized water to 1 liter; pH adjusted to 6.0.

YP medium was composed of 10 g of yeast extract, 20 g of Bacto peptone, and deionized water to 1 liter.

PEG buffer was composed of 500 g of polyethylene glycol 4000 (PEG 4000), 10 mM $CaCl_2$, 10 mM Tris-HCl pH 7.5, and deionized water to 1 liter; filter sterilized.

PDA plates were composed of 39 g of Potato Dextrose Agar (Difco) and deionized water to 1 liter.

PDA overlay medium was composed of 39 g of Potato Dextrose Agar (Difco), 2.44 g uridine, and deionized water to 1 liter. The previously autoclaved medium was melted in a microwave and then tempered to 55° C. before use.

STC was composed of 1 M sorbitol, 10 mM mM $CaCl_2$, and 10 mM Tris-HCl, pH 7.5; filter sterilized.

TE buffer was composed of 1 M Tris pH 8.0 and 0.5 M EDTA pH 8.0.

20×SSC was composed of 175.3 g of NaCl, 88.2 g of sodium citrate, and deionized water to 1 liter.

TrMM-G medium was composed of 20 ml of COVE salt solution, 6 g of $(NH_4)_2SO_4$, 0.6 g of $CaCl_2$, 25 g of Nobel agar (Difco), 20 g of glucose, and deionized water to 1 liter.

NZY+medium was composed of 5 g of NaCl, 3 g of $MgSO_4.7H_2O$, 5 g of yeast extract, 10 g of NZ amine, 1.2 g of $MgCl_2$, 4 g of glucose, and deionized water to 1 liter.

Example 1: Construction of a *Trichoderma reesei* cbhl-*Aspergillus fumigatus* cbhl Replacement Construct pJfyS139

The *Aspergillus fumigatus* cellobiohydrolase I (cbhl) coding sequence (SEQ ID NO: 1 [DNA sequence] and SEQ ID NO: 2 [deduced amino acid sequence]) was amplified from pEJG93 (WO 2011/057140) using the gene-specific forward and reverse primers shown below. The region in italics represents vector homology to the site of insertion for an IN-FUSION® reaction and the underlined portion is an introduced Pac I site.

```
Forward primer:
                                    (SEQ ID NO: 31)
5'-cgcggactgcgcaccATGCTGGCCTCCACCTTCTCCTACC-3'

Reverse primer:
                                    (SEQ ID NO: 32)
5'-ctttcgccacggagcttaattaaCTACAGGCACTGAGAGT

AATAATCA-3'
```

The amplification reaction was composed of 20 ng of pEJG93, 200 µM dNTP's, 0.4 µM primers, 1× HERCULASE® Reaction Buffer (Stratagene, La Jolla, Calif., USA), and 1.875 units of HERCULASE® Hot Start High-Fidelity DNA Polymerase (Stratagene, La Jolla, Calif., USA) in a final volume of 50 µl. The amplification reaction was incubated in an EPPENDORF® MASTERCYCLER® 5333 epgradient S (Eppendorf Scientific, Inc., Westbury, N.Y., USA) programmed for 1 cycle at 95° C. for 2 minutes; 30 cycles each at 95° C. for 30 seconds, 55° C. for 30 seconds, and 72° C. for 1 minute; and 1 cycle at 72° C. for 7 minutes. The PCR products were separated by 1% agarose gel electrophoresis using 40 mM Tris base, 20 mM sodium acetate, 1 mM disodium EDTA (TAE) buffer where a 1.6 kb fragment was excised from the gel and extracted using a MINELUTE® Gel Extraction Kit (QIAGEN Inc., Valencia, Calif., USA) according to the manufacturer's protocol.

The 1.6 kb PCR product was inserted into Nco I/Pac I-digested pSMai155 (WO 05/074647) using an IN-FUSION® Advantage PCR Cloning Kit (Clontech, Palo Alto, Calif., USA) according to the manufacturer's protocol. The IN-FUSION® reaction was composed of 1× IN-FUSION® Reaction Buffer (Clontech, Palo Alto, Calif., USA), 125 ng of Nco I/Pac I-digested pSMai155, 100 ng of the 1.6 kb PCR product, and 1 µl of IN-FUSION® Enzyme (Clontech, Palo Alto, Calif., USA) in a 10 µl reaction volume. The reaction was incubated for 15 minutes at 37° C. followed by 15 minutes at 50° C. After the incubation period 40 µl of TE buffer were added to the reaction. A 2 µl aliquot was used to transform ONE SHOT® TOP10 competent cells (Invitrogen, Carlsbad, Calif., USA) according to the manufacturer's protocol. The cells were heat shocked at 42° C. for 30 seconds and 250 µl of SOC medium were added. The tubes were incubated at 37° C., 200 rpm for 1 hour and 250 µl were plated onto 150 mm diameter 2XYT plus ampicillin plates and incubated at 37° C. overnight. The resulting transformants were screened by sequencing and one clone containing the insert with no PCR errors was identified and designated pJfyS139-A. Plasmid pJfyS139-A was used for insertion of the Herpes simplex virus thymidine kinase (tk) gene.

The Herpes simplex virus tk coding sequence (SEQ ID NO: 33 [DNA sequence] and SEQ ID NO: 34 [deduced amino acid sequence]) was liberated from pJfyS1579-8-6 (WO 2010/039840) by digesting the plasmid with Bgl II and Bam HI. The digestion was subjected to 1% agarose gel electrophoresis using TAE buffer where a 2.3 kb band was excised from the gel and extracted using a MINELUTE® Gel Extraction Kit. The tk gene cassette was inserted into Bam HI-digested, calf intestine phosphatase-treated pJfyS139-A using a QUICK LIGATION™ Kit (New England Biolabs, Inc., Ipswich, Mass. USA) according to the manufacturer's protocol. The ligation reaction was composed of 50 ng of the Bam HI-digested, calf intestine phosphatase-treated pJfyS139-A, 50 ng of the 2.3 kb tk gene insert, 1× QUICK LIGATION™ Buffer (New England Biolabs, Inc., Ipswich, Mass. USA), and 5 units of QUICK LIGASE™ (New England Biolabs, Inc., Ipswich, Mass. USA) in a final volume of 20 µl. The reaction was incubated at room temperature for 5 minutes and 2 µl of the reaction were used to transform ONE SHOT® TOP10 competent cells according to the manufacturer's protocol. The cells were heat shocked at 42° C. for 30 seconds and 250 µl of SOC medium were added. The tubes were incubated at 37° C., 200 rpm for 1 hour and 250 µl were plated onto 150 mm diameter 2XYT plus ampicillin plates and incubated at 37° C. overnight. The resulting transformants were screened by restriction digestion analysis with Xma I to determine the presence and orientation of the insert and a clone containing the insert was identified and designated pJfyS139-B. Plasmid pJfyS139-B was used for insertion of a *T. reesei* 3' cbhl gene flanking sequence.

The 3' cbhl gene flanking sequence was amplified from *T. reesei* RutC30 genomic DNA using the forward and reverse primers below. The underlined portion represents an introduced Not I site for cloning.

```
Forward Primer:
                                    (SEQ ID NO: 35)
5'-ttagactgcggccgcGTGGCGAAAGCCTGACGCACCGGTAGAT-3'

Reverse Primer:
                                    (SEQ ID NO: 36)
5'-agtagttagcggccgcACGGCACGGTTAAGCAGGGTCTTGC-3'
```

*Trichoderma reesei* RutC30 was grown in 50 ml of YP medium supplemented with 2% glucose (w/v) in a 250 ml baffled shake flask at 28° C. for 2 days with agitation at 200 rpm. Mycelia were harvested by filtration using MIRACLOTH® (Calbiochem, La Jolla, Calif., USA), washed twice in deionized water, and frozen under liquid nitrogen. Frozen mycelia were ground by mortar and pestle to a fine powder. Total DNA was isolated using a DNEASY® Plant Maxi Kit (QIAGEN Inc., Valencia, Calif., USA) with the lytic incubation extended to 2 hours.

The amplification reaction was composed of 150 ng of *T. reesei* RutC30 genomic DNA, 200 µM dNTP's, 0.4 µM primers, 1× HERCULASE® Reaction Buffer, and 1.875 units of HERCULASE® Hot Start High-Fidelity DNA Polymerase in a final volume of 50 µl. The amplification reaction was incubated in an EPPENDORF® MASTERCY- CLER® 5333 epgradient S programmed for 1 cycle at 95° C. for 2 minutes; 30 cycles each at 95° C. for 30 seconds, 60° C. for 30 seconds, and 72° C. for 1 minute 30 seconds; and 1 cycle at 72° C. for 7 minutes.

The PCR reaction was subjected to a MINELUTE® Nucleotide Removal Kit (QIAGEN Inc., Valencia, Calif., USA) according to the manufacturer's protocol. The resulting PCR mixture was digested with Not I and the digested PCR products were separated by 1% agarose gel electrophoresis using TAE buffer. A 1.3 kb fragment containing the 3' cbh1 gene flanking sequence was excised from the gel and extracted using a MINELUTE® Gel Extraction Kit. The 1.3 kb fragment was inserted into Not I-linearized, calf intestine phosphatase-treated pJfyS139-B using a QUICK LIGATION™ Kit. The QUICK LIGATION™ reaction was composed of 100 ng of the Not I-linearized, calf intestine phosphatase-treated pJfyS139-B, 20 ng of the 1.3 kb fragment, 1× QUICK LIGATION™ Buffer, and 5 units of QUICK LIGASE™ in a final volume of 20 µl. The reaction was incubated at room temperature for 5 minutes and 2 µl of the reaction was used to transform ONE SHOT® TOP10 competent cells according to the manufacturer's protocol. The cells were heat shocked at 42° C. for 30 seconds and 250 µl of SOC medium were added. The tubes were incubated at 37° C., 200 rpm for 1 hour and 250 µl were plated onto 150 mm diameter 2XYT plus ampicillin plates and incubated at 37° C. overnight. The resulting transformants were screened by restriction digestion analysis with Xma I to determine the presence and orientation of the insert and positive clones were sequenced. A clone containing the 3' cbh1 gene flanking sequence with no PCR errors was designated pJfyS139 (FIG. 1). Plasmid pJfyS139 was used as the vector to replace the *T. reesei* cbh1 gene.

Example 2: *Trichoderma reesei* Protoplast Generation and Transformation

Protoplast preparation and transformation were performed using a modified protocol by Penttila et al., 1987, Gene 61: 155-164. Briefly, *Trichoderma reesei* strain AgJg115-104-7B1 (PCT/US2010/061105, WO 2011/075677) was cultivated in 25 ml of YP medium supplemented with 2% (w/v) glucose and 10 mM uridine at 27° C. for 17 hours with gentle agitation at 90 rpm. Mycelia were collected by filtration using a Vacuum Driven Disposable Filtration System (Millipore, Bedford, Mass., USA) and washed twice with deionized water and twice with 1.2 M sorbitol. Protoplasts were generated by suspending the washed mycelia in 20 ml of 1.2 M sorbitol containing 15 mg of GLUCANEX® 200 G (Novozymes A/S, Bagsvaerd, Denmark) per ml and 0.36 units of chitinase (Sigma Chemical Co., St. Louis, Mo., USA) per ml for 15-25 minutes at 34° C. with gentle shaking at 90 rpm. Protoplasts were collected by centrifuging for 7 minutes at 400×g and washed twice with cold 1.2 M sorbitol. The protoplasts were counted using a haemocytometer and re-suspended to a final concentration of 1×10⁸ protoplasts per ml in STC. Excess protoplasts were stored in a Cryo 1° C. Freezing Container (Nalgene, Rochester, N.Y., USA) at −80° C.

Approximately 100 µg of a transforming plasmid described in the following Examples were digested with Pme I. The digestion reaction was purified by 1% agarose gel electrophoresis using TAE buffer. A DNA band was excised from the gel and extracted using a QIAQUICK® Gel Extraction Kit (QIAGEN Inc., Valencia, Calif., USA). The resulting purified DNA was added to 100 µl of the protoplast solution and mixed gently. PEG buffer (250 µl) was added, mixed, and incubated at 34° C. for 30 minutes. STC (3 ml) was then added, mixed, and spread onto PDA plates supplemented with 1 M sucrose. After incubation at 28° C. for 16 hours, 20 ml of an overlay PDA medium supplemented with 35 µg of hygromycin B per ml were added to each plate. The plates were incubated at 28° C. for 4-7 days.

Example 3: Replacement of the Native *Trichoderma reesei* Cbh1 Gene with the *Aspergillus fumigatus* cbh1 Coding Sequence In order to replace the *Trichoderma reesei* native cbh1 gene (SEQ ID NO: 17 [DNA sequence] and SEQ ID NO: 18 [deduced amino acid sequence]) with the *Aspergillus fumigatus* cbh1 coding sequence (SEQ ID NO: 1 [DNA sequence] and SEQ ID NO: 2 [deduced amino acid sequence]), *Trichoderma reesei* ku70-strain AgJg115-104-7B1 (PCT/US2010/061105, WO 2011/075677) was transformed with 4×2 µg of Pme I-linearized pJfyS139 (Example 1) according to the procedure described in Example 2. Seven transformants were obtained and each one was picked and transferred to a PDA plate and incubated for 7 days at 28° C. Genomic DNA was isolated from the transformants according to the procedure described in Example 1 and each transformant submitted to Southern analysis.

For Southern analysis, 2 µg of genomic DNA was digested with 33 units of Bgl II in a 50 µl reaction volume and subjected to 1% agarose electrophoresis in TAE buffer. The DNA in the gel was depurinated with one 10 minute wash in 0.25 N HCl, denatured with two 15 minute washes in 0.5 N NaOH-1.5 M NaCl, neutralized with one 30 minute wash in 1 M Tris pH 8-1.5 M NaCl, and incubated in 20×SSC for 5 minutes. The DNA was transferred to a NYTRAN® Supercharge membrane (Whatman, Inc., Florham Park, N.J., USA) using a TURBOBLOTTER™ System (Whatman, Inc., Florham Park, N.J., USA) according to the manufacturer's protocol. The DNA was UV crosslinked to the membrane using a STRATALINKER™ UV Crosslinker (Stratagene, La Jolla, Calif., USA) and prehybridized for 1 hour at 42° C. in 20 ml of DIG Easy Hyb (Roche Diagnostics Corporation, Indianapolis, Ind., USA).

A probe hybridizing to the 3' cbh1 gene flanking sequence was generated using a PCR Dig Probe Synthesis Kit (Roche Diagnostics Corporation, Indianapolis, Ind., USA) according to the manufacturer's instructions with the forward and reverse primers shown below. The PCR reaction was composed of 1× HERCULASE® Reaction Buffer, 400 nM of each primer, 200 µM DIG-labeled dUTP-containing dNTPs, 20 ng of pJfyS139, and 1.5 units of HERCULASE® Hot Start High-Fidelity DNA Polymerase. The amplification reaction was incubated in an EPPENDORF® MASTERCYCLER® 5333 epgradient S programmed for 1 cycle at 95° C. for 2 minutes; 25 cycles each at 95° C. for 30 seconds, 55° C. for 30 seconds, and 72° C. for 40 seconds; and 1 cycle at 72° C. for 7 minutes.

```
Forward primer:
                               (SEQ ID NO: 37)
5'-AAAAAACAAACATCCCGTTCATAAC-3'

Reverse primer:
                               (SEQ ID NO: 38)
5'-AACAAGGTTTACCGGTTTCGAAAAG-3'
```

The probe was purified by 1% agarose gel electrophoresis using TAE buffer where a 0.5 kb band corresponding to the probe was excised from the gel and extracted using a MINELUTE® Gel Extraction Kit. The probe was boiled for 5 minutes, chilled on ice for 2 minutes, and added to 10 ml of DIG Easy Hyb to produce the hybridization solution. Hybridization was performed at 42° C. for 15-17 hours. The membrane was then washed under low stringency conditions in 2×SSC plus 0.1% SDS for 5 minutes at room temperature followed by two high stringency washes in 0.5×SSC plus 0.1% SDS for 15 minutes each at 65° C. The probe-target hybrids were detected by chemiluminescent assay (Roche Diagnostics, Indianapolis, Ind., USA) according to the manufacturer's instructions. Southern analysis indicated that 3 of the 7 transformants contained the replacement cassette at the cbh1 locus and one transformant, *T. reesei* JfyS139-8, was chosen for curing the hpt and tk markers.

A fresh plate of spores was generated by transferring spores of a 7 day old PDA plate grown at 28° C. to a PDA plate and incubating for 7 days at 28° C. Spores were collected in 10 ml of 0.01% TWEEN® 20 using a sterile spreader. The concentration of spores was determined using a hemocytometer and $10^5$ spores were spread onto 150 mm plates containing TrMM-G medium supplemented with 1 µM 5-fluoro-2'-deoxyuridine (FdU).

Three hundred FdU-resistant spore isolates were obtained and DNA was extracted from 2 of the spore isolates as described above. The isolates were submitted to Southern analysis as described above and the results indicated that both spore isolates had excised the hpt/tk region between the homologous repeats of the replacement cassette. One strain designated *T. reesei* JfyS139-8A was chosen for replacing the cbh1l gene.

Example 4: Construction of an Empty *Trichoderma reesei* cbh1l Replacement Construct pJfyS142

To generate a construct to replace the *Trichoderma reesei* cbh1l gene (SEQ ID NO: 19 [DNA sequence] and SEQ ID NO: 20 [deduced amino acid sequence]) with the *Aspergillus fumigatus* cbh1l coding sequence (SEQ ID NO: 3 [DNA sequence] and SEQ ID NO: 4 [deduced amino acid sequence]), the *T. reesei* cbh1l promoter was first amplified from *T. reesei* RutC30 genomic DNA using the gene-specific forward and reverse primers shown below. The region in italics represents vector homology to the site of insertion in an IN-FUSION® reaction. *T. reesei* RutC30 genomic DNA was prepared according to the procedure described in Example Forward primer:
(SEQ ID NO: 39)
5'-*acgaattgtttaaacgtcgac*CCAAGTATCCAGAGGTGTATGGAAAT
ATCAGAT-3'

Reverse primer:
(SEQ ID NO: 40)
5'-*cgcgtagatctgcggccat*GGTGCAATACACAGAGGGTGATCTT-3'

The amplification reaction was composed of 20 ng of *T. reesei* RutC30 genomic DNA, 200 µM dNTP's, 0.4 µM primers, 1× HERCULASE® Reaction Buffer, and 1.875 units of HERCULASE® Hot Start High-Fidelity DNA Polymerase in a final volume of 50 µl. The amplification reaction was incubated in an EPPENDORF® MASTERCYCLER® programmed for 1 cycle at 95° C. for 2 minutes; 25 cycles each at 95° C. for 30 seconds, 55° C. for 30 seconds, and 72° C. for 1 minute 30 seconds; and 1 cycle at 72° C. for 7 minutes. The PCR products were separated by 1% agarose gel electrophoresis using TAE buffer where a 1.6 kb fragment was excised from the gel and extracted using a MINELUTE® Gel Extraction Kit.

The 1.6 kb PCR product was inserted into Nco I/Sal I-digested pSMai155 (WO 05/074647) using an IN-FUSION® Advantage PCR Cloning Kit according to the manufacturer's protocol. The IN-FUSION® reaction was composed of 1× IN-FUSION® Reaction Buffer, 125 ng of the Nco I/Sal I-digested pSMai155, 100 ng of the 1.6 kb PCR product, and 1 µl of IN-FUSION® Enzyme in a 10 µl reaction volume. The reaction was incubated for 15 minutes at 37° C. and 15 minutes at 50° C. After the incubation period 40 µl of TE were added to the reaction. A 2 µl aliquot was used to transform ONE SHOT® TOP10 competent cells according to the manufacturer's protocol. The cells were heat shocked at 42° C. for 30 seconds and 250 µl of SOC medium were added. The tubes were incubated at 37° C., 200 rpm for 1 hour and 250 µl were plated onto 150 mm diameter 2XYT plus ampicillin plates and incubated at 37° C. overnight. The resulting transformants were screened by restriction digestion analysis with Pci I and positive clones sequenced to ensure the absence of PCR errors. One clone containing the insert with no PCR errors was identified and designated pJfyS142-A. Plasmid pJfyS142-A was used to insert the *T. reesei* cbh1l terminator.

The cbh1l terminator was amplified from *T. reesei* RutC30 genomic DNA using the gene-specific forward and reverse primers shown below. The region in italics represents vector homology to the site of insertion in an IN-FUSION® reaction.

Forward primer:
(SEQ ID NO: 41)
5'-*atctacgcgtactagttaattaa*GGCTTTCGTGACCGGGCTTCAA
ACA-3'

Reverse primer:
(SEQ ID NO: 42)
5'-*gcggccgttactagtggatcc*ACTCGGAGTTGTTATACGCTAC
TCG-3'

The amplification reaction was composed of 150 ng of *T. reesei* RutC30 genomic DNA, 200 µM dNTP's, 0.4 µM primers, 1× HERCULASE® Reaction Buffer, and 1.875 units of HERCULASE® Hot Start High-Fidelity DNA Polymerase in a final volume of 50 µl. The amplification reaction was incubated in an EPPENDORF® MASTERCYCLER® programmed for 1 cycle at 95° C. for 2 minutes; 25 cycles each at 95° C. for 30 seconds, 54° C. for 30 seconds, and 72° C. for 50 seconds; and 1 cycle at 72° C. for 7 minutes. PCR products were separated by 1% agarose gel electrophoresis using TAE buffer where a 0.3 kb fragment was excised from the gel and extracted using a MINELUTE® Gel Extraction Kit.

The 0.3 kb PCR product was inserted into Pac 1l Bam HI-digested pJfyS142-A using an IN-FUSION® Advantage PCR Cloning Kit according to the manufacturer's protocol. The IN-FUSION® reaction was composed of 1× IN-FUSION® Reaction Buffer, 150 ng of the PacI/Bam HI-digested pJfyS142-A, 50 ng of the 0.3 kb PCR product, and 1 µl of IN-FUSION® Enzyme in a 10 µl reaction volume. The reaction was incubated for 15 minutes at 37° C. and 15 minutes at 50° C. After the incubation period 40 µl of TE were added to the reaction. A 2 µl aliquot was used to transform ONE SHOT® TOP10 competent cells according to the manufacturer's protocol. The cells were heat shocked at 42° C. for 30 seconds and 250 µl of SOC medium were added. The tubes were incubated at 37° C., 200 rpm for 1 hour and 250 µl were plated onto 150 mm diameter 2XYT plus ampicillin plates and incubated at 37° C. overnight. The transformants were screened by sequence analysis to identify positive clones and to ensure the absence of PCR errors. One clone containing the insert with no PCR errors was identified and designated pJfyS142-B. Plasmid pJfyS142-B was used for insertion of the Herpes simplex tk gene.

The Herpes simplex tk gene was liberated from pJfyS1579-8-6 (WO 2010/039840) by digesting the plasmid with Bgl II and Bam HI. The digestion was submitted to 1% agarose gel electrophoresis using TAE buffer where a 2.3 kb band was excised from the gel and extracted using a MINELUTE® Gel Extraction Kit. The tk cassette was inserted into Bam HI-digested, calf Intestine phosphatase-dephosphorylated pJfyS142-B using a QUICK LIGATION™ Kit according to the manufacturer's protocol. The ligation reaction was composed of 50 ng of the Bam HI-digested, calf Intestine phosphatase-dephosphorylated pJfyS142-B, 50 ng of the 2.3 kb tk gene insert, 1× QUICK LIGATION™ Buffer, and 5 units of QUICK LIGASE™ in a 20 µl ligation volume. The reaction was incubated at room temperature for 5 minutes and 2 µl of the reaction was used to transform ONE SHOT® TOP10 competent cells according to the manufacturer's protocol. The cells were heat shocked at 42° C. for 30 seconds and 250 µl of SOC medium were added. The tubes were incubated at 37° C., 200 rpm for 1 hour and 250 µl were plated onto 150 mm diameter 2XYT plus ampicillin plates and incubated at 37° C. overnight. The resulting transformants were screened by restriction digestion analysis with Xma I and Bam HI to determine the presence and orientation of the insert and a clone containing the insert was identified and designated pJfyS142-C. Plasmid pJfyS142-C was used for insertion of the *T. reesei* 3' cbhII gene flanking sequence.

The 3' cbhII gene flanking sequence was amplified from *T. reesei* RutC30 genomic DNA using the forward and reverse primers shown below. The region in italics represents vector homology to the site of insertion in an IN-FUSION® reaction.

```
Forward primer:
                                     (SEQ ID NO: 43)
5'-atccatcacactggcggccgcGCTTCAAACAATGATGTGCGAT

GGT-3'

Reverse primer:
                                     (SEQ ID NO: 44)
5'-gatgcatgctcgagcggccgcCTACCTTGGCAGCCCTACGAGA

GAG-3'
```

Figure 2:
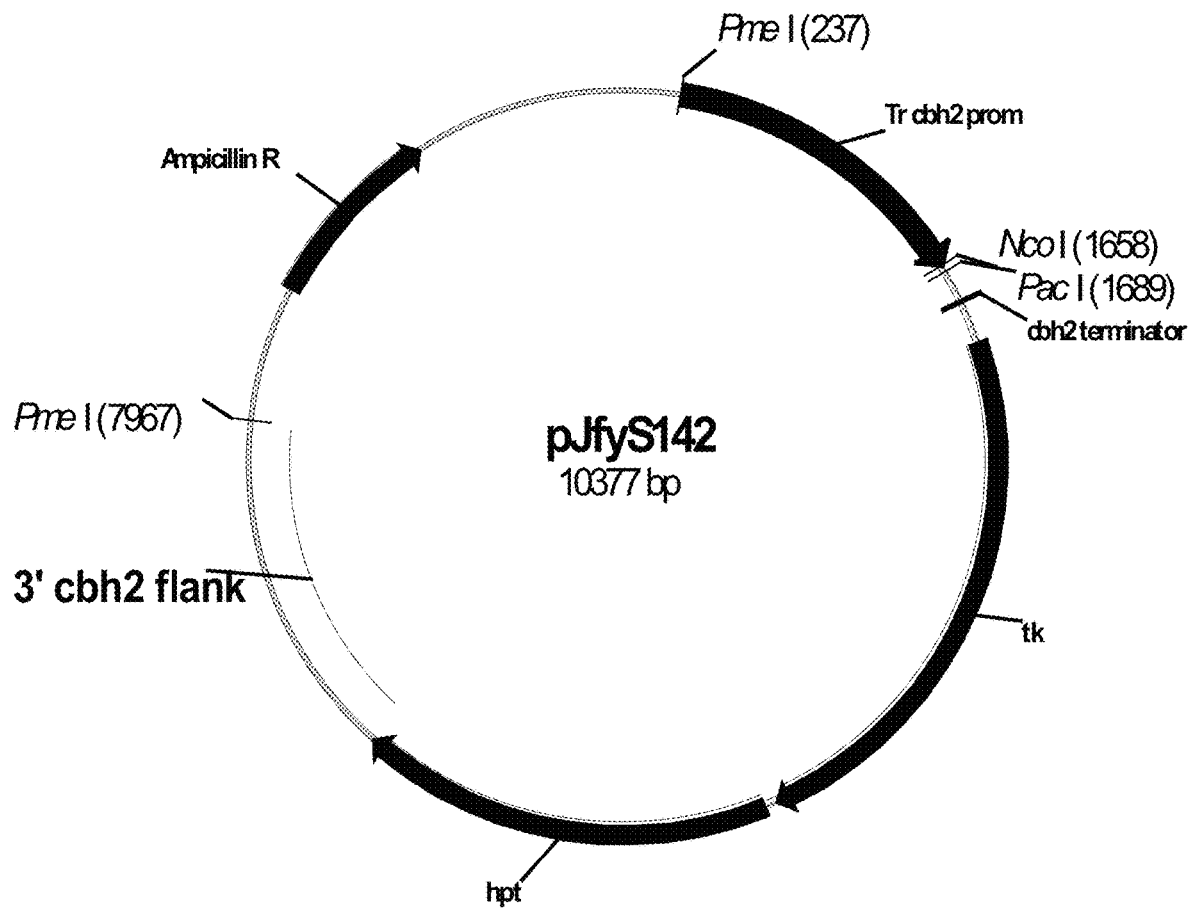
FIG. 2 shows a restriction map of plasmid pJfyS142.

The amplification reaction was composed of 150 ng of *T. reesei* RutC30 genomic DNA, 200 µM dNTP's, 0.4 µM primers, 1× HERCULASE® Reaction Buffer, and 1.875 units of HERCULASE® Hot Start High-Fidelity DNA Polymerase in a final volume of 50 µl. The amplification reaction was incubated in an EPPENDORF® MASTERCYCLER® programmed for 1 cycle at 95° C. for 2 minutes; 30 cycles each at 95° C. for 30 seconds, 56° C. for 30 seconds, and 72° C. for 1 minute 50 seconds; and 1 cycle at 72° C. for 7 minutes. The PCR reaction was subjected to 1% agarose gel electrophoresis using TAE buffer where a 1.5 kb band was excised from the gel and extracted using a MINELUTE® Gel Extraction Kit. The 3' cbhII gene flanking sequence was inserted into Not I-linearized pJfyS142-C using an IN-FUSION® Advantage PCR Cloning Kit according to the manufacturer's protocol. The IN-FUSION® reaction was composed of 1× IN-FUSION® Reaction Buffer, 150 ng of pJfyS142-C, 80 ng of the 1.5 kb PCR product, and 1 µl of IN-FUSION® Enzyme in a 10 µl reaction volume. The reaction was incubated for 15 minutes at 37° C. and 15 minutes at 50° C. After the incubation period 40 µl of TE were added to the reaction. A 2 µl aliquot was used to transform ONE SHOT® TOP10 competent cells according to the manufacturer's protocol. The cells were heat shocked at 42° C. for 30 seconds and 250 µl of SOC medium were added. The tubes were incubated at 37° C., 200 rpm for 1 hour and 250 µl were plated onto 150 mm diameter 2XYT plus ampicillin plates and incubated at 37° C. overnight. The resulting transformants were screened by restriction digestion analysis with Bgl II and positive clones were sequenced to ensure the absence of PCR errors. One clone containing the insert with no PCR errors was identified and designated pJfyS142 (FIG. 2). Plasmid pJfyS142 was used to insert the *A. fumigatus* cbhII coding sequence.

Example 5: Construction of a *Trichoderma reesei* cbhII-*Aspergillus fumigatus* cbhII Replacement Construct pJfyS144

The *Aspergillus fumigatus* cbhII coding sequence (SEQ ID NO: 3 [DNA sequence] and SEQ ID NO: 4 [deduced amino acid sequence]) was amplified from pAlLo33 (WO 2011/057140) using the forward and reverse primers shown below. The region in italics represents vector homology to the site of insertion for an IN-FUSION® reaction.

```
Forward primer:
                                     (SEQ ID NO: 45)
5'-ctctgtgtattgcaccATGAAGCACCTTGCATCTTCCATCG-3'

Reverse primer:
                                     (SEQ ID NO: 46)
5'-ccggtcacgaaagccTTAATTAAAAGGACGGGTTAGCGTT-3'
```

The amplification reaction was composed of 20 ng of pAlLo33, 200 µM dNTP's, 0.4 µM primers, 1 mM HERCULASE® Reaction Buffer, and 1.875 units of HERCULASE® Hot Start High-Fidelity DNA Polymerase in a final volume of 50 µl. The amplification reaction was incubated in an EPPENDORF® MASTERCYCLER® programmed for 1 cycle at 95° C. for 2 minutes; 30 cycles each at 95° C. for 30 seconds, 55° C. for 30 seconds, and 72° C. for 2 minutes; and 1 cycle at 72° C. for 7 minutes.

Figure 3:
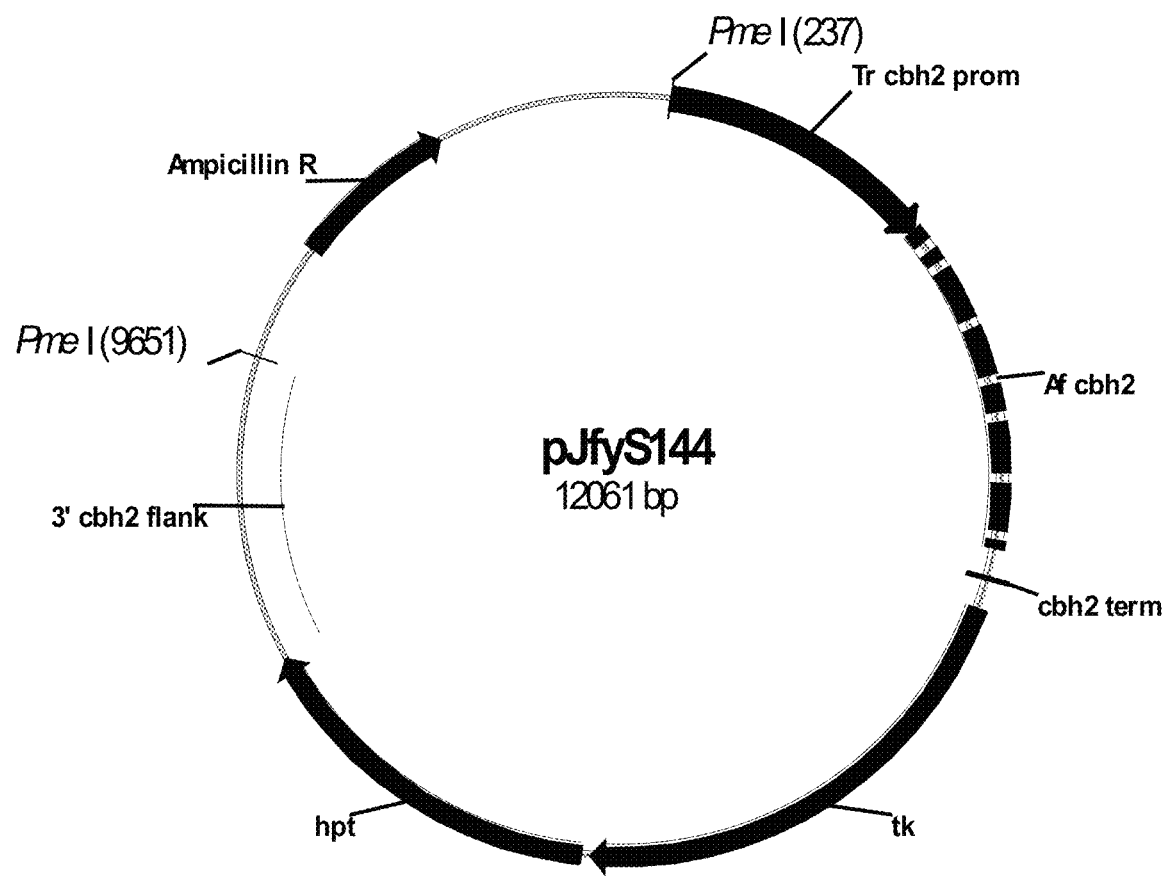
FIG. 3 shows a restriction map of plasmid pJfyS144.

The PCR reaction was subjected to 1% agarose gel electrophoresis using TAE buffer where a 1.7 kb band was excised from the gel and extracted using a MINELUTE® Gel Extraction Kit. The 1.7 kb PCR product was inserted into Nco I/Pac I-digested pJfyS142 (Example 4) using an IN-FUSION® Advantage PCR Cloning Kit according to the manufacturer's protocol. The IN-FUSION® reaction was composed of 1× IN-FUSION® Reaction Buffer, 120 ng of the Nco I/Pac I-digested pJfyS142, 70 ng of the 1.7 kb PCR product, and 1 µl of IN-FUSION® Enzyme in a 10 µl reaction volume. The reaction was incubated for 15 minutes at 37° C. and 15 minutes at 50° C. After the incubation period 40 µl of TE were added to the reaction. A 2 µl aliquot was used to transform ONE SHOT® TOP10 competent cells according to the manufacturer's protocol. The cells were heat shocked at 42° C. for 30 seconds and 250 µl of SOC medium were added. The tubes were incubated at 37° C., 200 rpm for 1 hour and 250 µl were plated onto 150 mm diameter 2XYT plus ampicillin plates and incubated at 37° C. overnight. The resulting transformants were sequenced to ensure the absence of PCR errors and determine the presence of the insert. One clone with error-free sequence was identified and designated pJfyS144 (FIG. 3). Plasmid pJfyS144 was used to replace the native cbhll gene with the cbhll coding sequence from *A. fumigatus*.

Example 6: Replacement of the Native *Trichoderma reesei* cbhll Gene with the *Aspergillus fumigatus* cbhll Coding Sequence In order to replace the native *T. reesei* cbhll gene (SEQ ID NO: 19 [DNA sequence] and SEQ ID NO: 20 [deduced amino acid sequence]) with the *Aspergillus fumigatus* cbhll coding sequence (SEQ ID NO: 3 [DNA sequence] and SEQ ID NO: 4 [deduced amino acid sequence]), *Trichoderma reesei* JfyS139-8A (Example 3) was transformed according to the procedure described in Example 2 with 2 µg of Pme I-linearized and gel purified pJfyS144 (Example 5). Seven transformants were obtained and each one was picked and transferred to a PDA plate and incubated for 7 days at 28° C. A fungal spore PCR method described below was used to screen for transformants bearing gene replacement using the forward primer shown below annealing to a region upstream of the 5' cbhll gene flanking sequence beyond the region of integration, and the reverse primer shown below annealing in the *A. fumigatus* cbhll coding sequence.

```
Forward primer:
                                     (SEQ ID NO: 47)
5'-AGCCACATGCCGCATATTGACAAAG-3'

Reverse primer:
                                     (SEQ ID NO: 48)
5'-AGGGATTCAGTGTGCTACAGGCTGC-3'
```

A 1.8 kb PCR product would be generated only upon the occurrence of a precise gene replacement at the cbhll locus. If the cassette had integrated elsewhere in the genome, no amplification would result.

A small amount of spores from each transformant was suspended in 25 µl of TE buffer and heated on high in a microwave oven for 1 minute. Each microwaved spore suspension was used as a template in the PCR reaction. The reaction was composed of 1 µl of the microwaved spore suspension, 1 µl of a 10 mM dNTPs, 12.5 µl of 2×ADVANTAGE® GC-Melt LA Buffer (Clontech, Mountain View, Calif., USA), 25 pmol of forward primer, 25 pmol of reverse primer, 1.25 units of ADVANTAGE® GC Genomic LA Polymerase Mix (Clontech, Mountain View, Calif., USA), and 9.25 µl of water. The reaction was incubated in an EPPENDORF® MASTERCYCLER® 5333 epgradient S programmed for 1 cycle at 95° C. for 10 minutes; 35 cycles each at 95° C. for 30 seconds, 56° C. for 30 seconds, and 72° C. for 1 minute 40 seconds; 1 cycle at 72° C. for 7 minutes; and a 4° C. hold. The PCR reactions were subjected to 1% agarose gel electrophoresis using TAE buffer. The spore PCR indicated that four of the seven transformants contained the replacement cassette at the targeted locus and three of them were submitted to Southern analysis to confirm the replacement cassette was in a single copy.

Genomic DNA was isolated from the three transformants according to the procedure described in Example 1 and each transformant submitted to Southern analysis. For Southern analysis, 2 µg of genomic DNA was digested with 50 units of Dra I in a 50 µl reaction volume and subjected to 1% agarose electrophoresis in TAE buffer. The DNA in the gel was depurinated with one 10 minute wash in 0.25 N HCl, denatured with two 15 minute washes in 0.5 N NaOH-1.5 M NaCl, neutralized with one 30 minute wash in 1 M Tris pH 8-1.5 M NaCl, and incubated in 20×SSC for 5 minutes. The DNA was transferred to a NYTRAN® Supercharge membrane. The DNA was UV crosslinked to the membrane using a STRATALINKER™ UV crosslinker and prehybridized for 1 hour at 42° C. in 20 ml of DIG Easy Hyb.

A probe hybridizing to the 3' cbhll gene flanking sequence was generated using a PCR Dig Probe Synthesis Kit according to the manufacturer's instructions with the forward and reverse primers indicated below. The PCR reaction was composed of 1× HERCULASE® Reaction Buffer, 400 nM each primer, 200 µM DIG-labeled dUTP-containing dNTPs, 150 ng of *T. reesei* RutC30 genomic DNA, and 1.5 units of HERCULASE® Hot Start High-Fidelity DNA Polymerase. The reaction was incubated in an EPPENDORF® MASTERCYCLER® 5333 epgradient S programmed for 1 cycle at 95° C. for 2 minutes; 30 cycles each at 95° C. for 30 seconds, 51° C. for 30 seconds, and 72° C. for 40 seconds; and 1 cycle at 72° C. for 7 minutes.

```
Forward primer:
                                     (SEQ ID NO: 49)
5'-AAAAAACAAACATCCCGTTCATAAC-3'

Reverse primer:
                                     (SEQ ID NO: 50)
5'-AACAAGGTTTACCGGTTTCGAAAAG-3'
```

The probe was purified by 1% agarose gel electrophoresis using TAE buffer where a 0.5 kb band corresponding to the probe was excised from the gel and extracted using a QIAQUICK® Gel Extraction Kit. The probe was boiled for 5 minutes, chilled on ice for 2 minutes, and added to 10 ml of DIG Easy Hyb to produce the hybridization solution. Hybridization was performed at 42° C. for approximately 17 hours. The membrane was then washed under low stringency conditions in 2×SSC plus 0.1% SDS for 5 minutes at room temperature followed by two high stringency washes in 0.5×SSC plus 0.1% SDS for 15 minutes each at 65° C. The probe-target hybrids were detected by chemiluminescent assay (Roche Diagnostics, Indianapolis, Ind., USA) according to the manufacturer's instructions. Southern analysis indicated that the three transformants contained the replacement cassette at the cbhll locus and all three (designated JfyS139/144-5, -6, and -10) were chosen for curing the hpt and tk markers.

A fresh plate of spores for each transformant was generated by transferring a plug of a 7 day old culture grown on a PDA plate at 28° C. to a new PDA plate and incubating for 7 days at 28° C. Spores were collected in 10 ml of 0.01% TWEEN® 20 using a sterile spreader. The concentration of spores was determined using a hemacytometer and $10^5$ and $10^4$ spores were spread onto 150 mm plates containing TrMM-G medium supplemented with 1 µM FdU.

Approximately 500 FdU-resistant spore isolates for each transformant were obtained from the plate containing $10^5$ spores and approximately 100 FdU-resistant spore isolates for each transformant from the plate containing $10^4$ spores. Eight spore isolates were picked for strains JfyS139/144-5 and -6 and four were picked for strain JfyS139/144-10. Each isolate 1 to 8 from primary transformant 5 was designated JfyS139/144-5A to -5H. Isolates 1 to 8 from primary transformant 6 were designated JfyS139/144-6A to 6H. Isolates from primary transformant 10 were designated JfyS139/

144-10A to 10D for isolates 1 to 4. Spore PCR was conducted as described above, using the forward and reverse primers shown below, to confirm the hpt and tk markers had been correctly excised.

Forward primer:
(SEQ ID NO: 51)
5'-GTTAAGCATACAATTGAACGAGAATGG-3'

Reverse primer:
(SEQ ID NO: 52)
5'-GATGATATAATGGAGCAAATAAGGG-3'

The PCR reactions were performed as described above with the following cycling parameters: 1 cycle at 95° C. for 2 minutes; 30 cycles each at 95° C. for 30 seconds, 55° C. for 30 seconds, and 72° C. for 6 minutes seconds; and 1 cycle at 72° C. for 7 minutes.

The primers annealed to the 5' (forward) and 3' (reverse) flanking sequences used for the cbhII gene replacement. Strains from which the hpt/tk cassette had been correctly excised would display a 3.5 kb fragment while those with the markers intact would display an 8 kb fragment. The PCR screen indicated that all of the spore isolates had correctly excised the hpt/tk cassette.

DNA was extracted from the A and B spore isolates from each primary transformant and submitted to Southern analysis as described above. The Southern analysis confirmed that each spore isolate had correctly excised the hpt/tk cassette. Spore isolate *T. reesei* JfyS139/144-10B was chosen to represent the strain containing both the *T. reesei* cbhI and cbhII genes replaced with the respective homologs from *Aspergillus fumigatus*.

Example 7: Generation of *Trichoderma reesei* Ku70 Gene Repair Plasmid pTH239

Four DNA segments were combined using an IN-FUSION® Advantage PCR Cloning Kit to generate a construct to replace the disrupted *Trichoderma reesei* ku70 coding sequence with the native *Trichoderma reesei* ku70 coding sequence [(SEQ ID NO: 53 [DNA sequence] and SEQ ID NO: 54 [deduced amino acid sequence]). The ampicillin resistance marker region including the prokaryotic origin of replication was amplified from pJfyS139-B (Example 4) using the sequence-specific forward and reverse primers shown below (SEQ ID NOs: 55 and 56). The *T. reesei* ku70 gene upstream sequence (consisting of 989 bp from upstream of the ku70 coding sequence and the first 1010 bp of the ku70 coding sequence) was amplified from *T. reesei* 981-O-8 genomic DNA using the sequence-specific forward and reverse primers shown below (SEQ ID NOs: 57 and 58). The *T. reesei* ku70 gene downstream sequence (consisting of a 500 bp segment repeated from the 3' end of the 1010 bp segment of the ku70 coding sequence amplified in the upstream PCR product, and a 1067 bp segment containing the remainder of the ku70 coding sequence, and 461 bp from downstream of the ku70 coding sequence) was amplified from *T. reesei* 981-O-8 genomic DNA using the sequence-specific forward and reverse primers shown below (SEQ ID NOs: 59 and 60). *T. reesei* 981-O-8 genomic DNA was prepared according to the procedure described in Example 1.

Forward primer:
(SEQ ID NO: 55)
5'-GTGTGCGGCCGCTCGAGCATGCATGTTTAAACAGCTTGGCACTGGCC

GTCGTTTT-3'

Reverse primer:
(SEQ ID NO: 56)
5'-ATCAGOOOOGAGACGGCGCCGCGTTTAAACAATTCGTAATCATGGTC

ATAGCTGT-3'

Forward primer:
(SEQ ID NO: 57)
5'-CATGATTACGAATTGTTTAAACGCGGCGCCGTCTCGGGGCTGATCTT

GTCGAGGA-3'

Reverse primer:
(SEQ ID NO: 58)
5'-GGCGGCCGTTACTAGTGGATCCAGOOOTTGACAGTGATCTTGAGTCC

AGGTGCAA-3'

Forward primer:
(SEQ ID NO: 59)
5'-TGCAGATATCCATCACACTGGCGGCCGCAGTTTCCATGTCCAACGTG

TTGTTTTGCGC-3'

Reverse primer:
(SEQ ID NO: 60)
5'-GCCAGTGCCAAGCTGTTTAAACATGCATGCTCGAGCGGCCGCACACG

CCCTCTCCTCG-3'

For amplification of the ampicillin resistance marker and prokaryotic origin of replication region, the reaction was composed of 100 ng of *T. reesei* 981-O-8 genomic DNA, 200 μM dNTPs, 1 μM of each primer (SEQ ID NO: 55 and 56), 1× PHUSION® High-Fidelity Hot Start DNA Polymerase Buffer (New England Biolabs, Inc., Ipswich, Mass., USA), and 1.0 unit of PHUSION® High-Fidelity Hot Start DNA Polymerase (New England Biolabs, Inc., Ipswich, Mass., USA) in a final volume of 50 μl. The amplification reaction was incubated in an EPPENDORF® MASTERCYCLER® 5333 epgradient S programmed for 1 cycle at 98° C. for 30 seconds; 30 cycles each at 98° C. for 10 seconds, 55° C. for 30 seconds, and 72° C. for 1 minute 30 seconds; and 1 cycle at 72° C. for 7 minutes. The PCR product was separated by 1% agarose gel electrophoresis using TAE buffer where a 2.692 kb fragment was excised from the gels and extracted using a MINELUTE® Gel Extraction Kit.

For amplification of the ku70 gene upstream sequence or downstream sequence, the reactions were composed of 100 ng of pJfyS139-B, 200 μM dNTPs, 1 μM of each primer (SEQ ID NOs: 57 and 58 or 59 and 60, respectively), 1× PHUSION® High-Fidelity Hot Start DNA Polymerase Buffer, and 1.0 unit of PHUSION® High-Fidelity Hot Start DNA Polymerase in a final volume of 50 μl. The amplification reactions were incubated in an EPPENDORF® MASTERCYCLER® 5333 epgradient S programmed for 1 cycle at 98° C. for 30 seconds; 30 cycles each at 98° C. for 10 seconds, 55° C. for 30 seconds, and 72° C. for 1 minute 30 seconds; and 1 cycle at 72° C. for 7 minutes. The PCR products were separated by 1% agarose gel electrophoresis using TAE buffer where 1.999 kb and 2.028 kb fragments were separately excised from the gels and extracted using a MINELUTE® Gel Extraction Kit.

The fourth DNA segment was generated from a restriction enzyme digestion of pJfyS139-B with Not I and Bam HI. The reaction was composed of 5 μg of pJfyS139-B, 10 units of Not I, 20 units of Bam HI, and 20 μl of Restriction Enzyme Buffer 2 (New England Biolabs, Inc., Ipswich, Mass., USA) in a total volume of 50 µl. The reaction was incubated for 1 hour at 37° C. and then separated by 1% agarose gel electrophoresis using TAE buffer where a 4.400 kb fragment was excised from the gel and extracted using a MINELUTE® Gel Extraction Kit.

The three PCR products of 2,028 bp, 1,999 bp and 2,692 bp were inserted into Not I and Bam HI-digested pJfyS139-B using an IN-FUSION® Advantage PCR Cloning Kit according to the manufacturer's protocol. The IN-FUSION® reaction was composed of 1× IN-FUSION® Reaction Buffer, 50 ng of the Not II Bam HI-digested pJfyS139-B, 50 ng of the 1.999 kb ku70 gene upstream PCR product, 50 ng of the 2.028 kb ku70 gene downstream PCR product, 50 ng of the 2.692 kb ampicillin resistance marker and prokaryotic origin of replication PCR product, and 1 µl of IN-FUSION® Enzyme in a 10 µl reaction volume. The reaction was incubated for 15 minutes at 37° C. followed by 15 minutes at 50° C. After the incubation period 40 µl of TE were added to the reaction. A 3 µl aliquot was used to transform E. coli XL10 GOLD® competent cells (Stratagene, La Jolla, Calif., USA) according to the manufacturer's protocol. The cells were heat shocked at 42° C. for 30 seconds and then 500 µl of NZY+medium, pre-heated to 42° C., were added. The tubes were incubated at 37° C. with shaking at 200 rpm for 40 minutes and then plated onto 150 mm diameter 2XYT plus ampicillin plates and incubated at 37° C. overnight. The resulting transformants were screened by restriction digestion analysis with Hind III and Xba I and positive clones sequenced to ensure the absence of PCR errors. One clone containing the insert with no PCR errors was identified and designated pTH239.

Example 8: Repair of the ku70 Gene in the A. fumigatus cbh1 and cbh2 Replacement Strain JfyS139/144-10B The native Trichoderma reesei ku70 gene was repaired in strain T. reesei JfyS139/144-10B (Example 6) in order to facilitate strain manipulation steps requiring the function of the ku70 gene in non-homologous end-joining. T. reesei JfyS129/144-10B was transformed with 23×2 µg of Pme I-linearized pTH239 (Example 7) according to the procedure described in Example 2. Nineteen transformants were obtained and each one was separately transferred to a PDA plate and incubated for 7 days at 28° C.

All nineteen transformants were screened by PCR to confirm homologous integration of the pTH239 Pme I fragment at the disrupted ku70 gene locus. For each of the transformants a sterile inoculation loop was used to collect spores from a 7 day old PDA plate. The spores were transferred to a tube containing 25 µl of 1 mM EDTA-10 mM Tris buffer and microwaved on high for 1 minute. A 1 µl aliquot of the microwaved spore mixture was added directly to the PCR reaction as template DNA. A set of PCR primers shown below were designed to amplify across the disrupted region of the ku70 coding sequence to distinguish between the host genome with the disruption in the ku70 coding sequence (848 bp) and the pTH239 targeted strain of interest (606 bp). The PCR reaction was composed of 1× ADVANTAGE® Genomic LA Polymerase Reaction Buffer (Clontech, Mountain View, Calif., USA), 400 nM of each primer, 200 µM dNTPs, 1 µl of microwaved TE-spore mixture (described above), and 1.0 unit of ADVANTAGE® Genomic LA Polymerase (Clontech, Mountain View, Calif., USA). The amplification reaction was incubated in an EPPENDORF® MASTERCYCLER® 5333 epgradient S programmed for 1 cycle at 95° C. for 10 minutes; 30 cycles each at 95° C. for 30 seconds, 55° C. for 30 seconds, and 72° C. for 60 seconds; and 1 cycle at 72° C. for 7 minutes.

```
Forward primer:
                                   (SEQ ID NO: 61)
5'-CAATGACGATCCGCACGCGT-3'

Reverse primer:
                                   (SEQ ID NO: 62)
5'-CAATGACGATCCGCACGCGT-3'
```

Only one of the nineteen transformants (#19) was positive for the 606 bp PCR product and negative for the 848 bp PCR product indicative of a strain containing the pTH239 PmeI fragment homologously integrated at the ku70 locus.

Spores from the 7 day old PDA plate of transformant #19 were collected in 10 ml of 0.01% TWEEN® 20 using a sterile spreader. The concentration of spores was determined using a hemocytometer and $10^6$ spores were spread onto 150 mm plates containing TrMM-G medium supplemented with 1 µM 5-fluoro-2'-deoxyuridine (FdU) and cultured for 5 days at 28° C. Twenty-two FdU-resistant spore isolates were obtained and transferred to PDA plates and cultivated at 28° C. for five days.

All twenty-two spore isolates (#19A-V) were screened by PCR for excision of the hpt/tk marker region present between the homologous repeats of the ku70 coding sequence within the repair cassette. For each of the spore isolates a sterile inoculating loop was used to collect spores from a 7 day old PDA plate. The spores were transferred to a tube containing 25 µl of 1 mM EDTA-10 mM Tris buffer and microwaved on high for 1 minute. A 1 µl aliquot of the spore mixture was added directly to the PCR reaction as template genomic DNA. A set of PCR primers shown below were designed to amplify across the hpt/tk region to distinguish between the presence (6 kb) or absence (1.1 kb) of the hpt/tk region. The PCR reaction was composed of 1× ADVANTAGE® Genomic LA Polymerase Reaction Buffer, 400 nM of each primer (below), 200 µM dNTPs, 1 µl of microwaved TE-spore mixture (described above), and 1.0 unit of ADVANTAGE® Genomic LA Polymerase. The amplification reaction was incubated in an EPPENDORF® MASTERCYCLER® 5333 epgradient S programmed for 1 cycle at 95° C. for 10 minutes; 30 cycles each at 95° C. for 30 seconds, 50° C. for 30 seconds, and 72° C. for 6 minutes; and 1 cycle at 72° C. for 7 minutes.

```
Forward primer:
                                   (SEQ ID NO: 63)
5'-GACACTCTTTTCTCCCATCT-3'

Reverse primer:
                                   (SEQ ID NO: 64)
5'-GAGGAGCAGAAGAAGCTCCG-3'
```

All twenty-two spore isolates were negative for the 6 kb PCR product corresponding to the hpt/tk marker region.

Spores from the 7 day old PDA plates of isolates #19A and #19L were collected in 10 ml of 0.01% TWEEN® 20 using a sterile spreader. The concentration of spores was determined using a hemocytometer and $10^3$, $10^2$, and $10^1$ spores were spread onto 150 mm PDA plates containing 1 M sucrose and cultured for 3 days at 28° C. Ten spore isolates were selected from the PDA plates for both strains #19A and #19L and transferred to fresh PDA plates and placed at 28° C.

Genomic DNA was extracted from 6 spore isolates of both #19L and #19A, according to the procedure described in Example 1 and submitted to Southern analysis.

For Southern analysis, 2 µg of genomic DNA was digested with (1) 5 units and 10 units, respectively, of Asc I and Xho I or (2) 5 units and 25 units, respectively, of Asc I and Apa I in a 50 µl reaction volume and subjected to 1% agarose electrophoresis using TAE buffer. The DNA in the gel was depurinated with one 10 minute wash in 0.25 N HCl, denatured with two 15 minute washes in 0.5 N NaOH-1.5 M NaCl, neutralized with one 30 minute wash in 1 M Tris pH 8-1.5 M NaCl, and incubated in 20×SSC for 5 minutes. The DNA was transferred to a NYTRAN® Supercharge membrane using a TURBOBLOTTER™ System according to the manufacturer's protocol. The DNA was UV crosslinked to the membrane using a STRATALINKER™ UV Crosslinker and prehybridized for 1 hour at 42° C. in 20 ml of DIG Easy Hyb.

A probe hybridizing to the 3' end of the ku70 coding sequence was generated using a PCR Dig Probe Synthesis Kit (Roche Diagnostics Corporation, Indianapolis, Ind., USA) according to the manufacturer's instructions with the forward and reverse primers shown below. In order to generate a pure template for the probe PCR reaction, the 3' end of the ku70 coding sequence was amplified from *T. reesei* 981-O-8 genomic DNA. The PCR reaction was composed of 1× PHUSION® High-Fidelity Hot Start DNA Polymerase Buffer, 1 µM of each primer, 200 µM dNTPs, 165 ng of *T. reesei* 981-O-8 genomic DNA, and 1.0 unit of PHUSION® High-Fidelity Hot Start DNA Polymerase. The amplification reaction was incubated in an EPPENDORF® MASTERCYCLER® 5333 epgradient S programmed for 1 cycle at 98° C. for 30 seconds; 35 cycles each at 98° C. for 10 seconds, 60° C. for 30 seconds, and 72° C. for 15 seconds; and 1 cycle at 72° C. for 10 minutes.

```
Forward primer:
                                     (SEQ ID NO: 65)
5'-gcatatataacccactcaagta-3'

Reverse primer:
                                     (SEQ ID NO: 66)
5'-attatcttggaccggccgcagg-3'
```

The 0.5 kb probe template was purified by 1% agarose gel electrophoresis using TAE buffer and excised from the gel and extracted using a MINELUTE® Gel Extraction Kit. The purified PCR product was used to generate a DIG-labeled probe as specified by the manufacturer's instructions using the primers and amplification conditions specified above. The 0.5 kb DIG-labeled probe was purified by 1% agarose gel electrophoreseis using TAE buffer and excised from the gel and extracted using a MINELUTE® Gel Extraction Kit. The probe was boiled for 5 minutes, chilled on ice for 2 minutes, and added to 10 ml of DIG Easy Hyb to produce the hybridization solution. Hybridization was performed at 42° C. for 15-17 hours. The membrane was then washed under low stringency conditions in 2×SSC plus 0.1% SDS for 5 minutes at room temperature followed by two high stringency washes in 0.5×SSC plus 0.1% SDS for 15 minutes each at 65° C. The probe-target hybrids were detected by chemiluminescent assay (Roche Diagnostics, Indianapolis, Ind., USA) according to the manufacturer's instructions. Southern analysis indicated that all spore isolates contained the repair/replacement cassette at the ku70 locus and were cured of the hpt and tk markers. One strain designated *T. reesei* 981-O-8.5 #10B+Ku70 #19L3 was chosen for further transformations.

Example 9: Construction of pDM286 Expressing a *Penicillium* sp. GH61A Polypeptide The *Penicillium* sp. (*emersonii*) GH61A polypeptide coding sequence (SEQ ID NO: 7 [DNA sequence] and SEQ ID NO: 8 [deduced amino acid sequence]) was amplified from plasmid pGH61D23Y4 (WO 2011/041397) using the gene-specific forward and reverse primers shown below. The region in italics represents vector homology to the site of insertion for an IN-FUSION® reaction.

```
Forward primer:
                                     (SEQ ID NO: 67)
5'-CGGACTGCGCACCATGCTGTCTTCGACGACTCGCAC-3'

Reverse primer:
                                     (SEQ ID NO: 68)
5'-TCGCCACGGAGCTTATCGACTTCTTCTAGAACGTC-3'
```

The amplification reaction was composed of 30 ng of pGH61D23Y4 DNA, 50 µmoles of each of the primers listed above, 1 µl of a 10 mM blend of dATP, dTTP, dGTP, and dCTP, 1× PHUSION™ High-Fidelity Hot Start DNA Polymerase Buffer, and 1 unit of PHUSION™ High-Fidelity Hot Start DNA Polymerase in a final volume of 50 µl. The amplification reaction was incubated in an EPPENDORF® MASTERCYCLER® 5333 epgradient S programmed for 1 cycle at 98° C. for 30 seconds; 35 cycles each at 98° C. for 10 seconds, 60° C. for 30 seconds, and 72° C. for 30 seconds; and 1 cycle at 72° C. for 10 minutes. The PCR products were separated by 1% agarose gel electrophoresis using TAE buffer where an approximately 0.9 kb fragment was excised from the gel and extracted using a QIAQUICK® Gel Extraction Kit according to the manufacturer's protocol.

Plasmid pMJ09 (WO 2005/047499) was digested with Nco I and Pac I, isolated by 1.0% agarose gel electrophoresis in 1 mM disodium EDTA-50 mM Tris base-50 mM boric acid (TBE) buffer, excised from the gel, and extracted using a QIAQUICK® Gel Extraction Kit according to the manufacturer's instructions.

Figure 4:
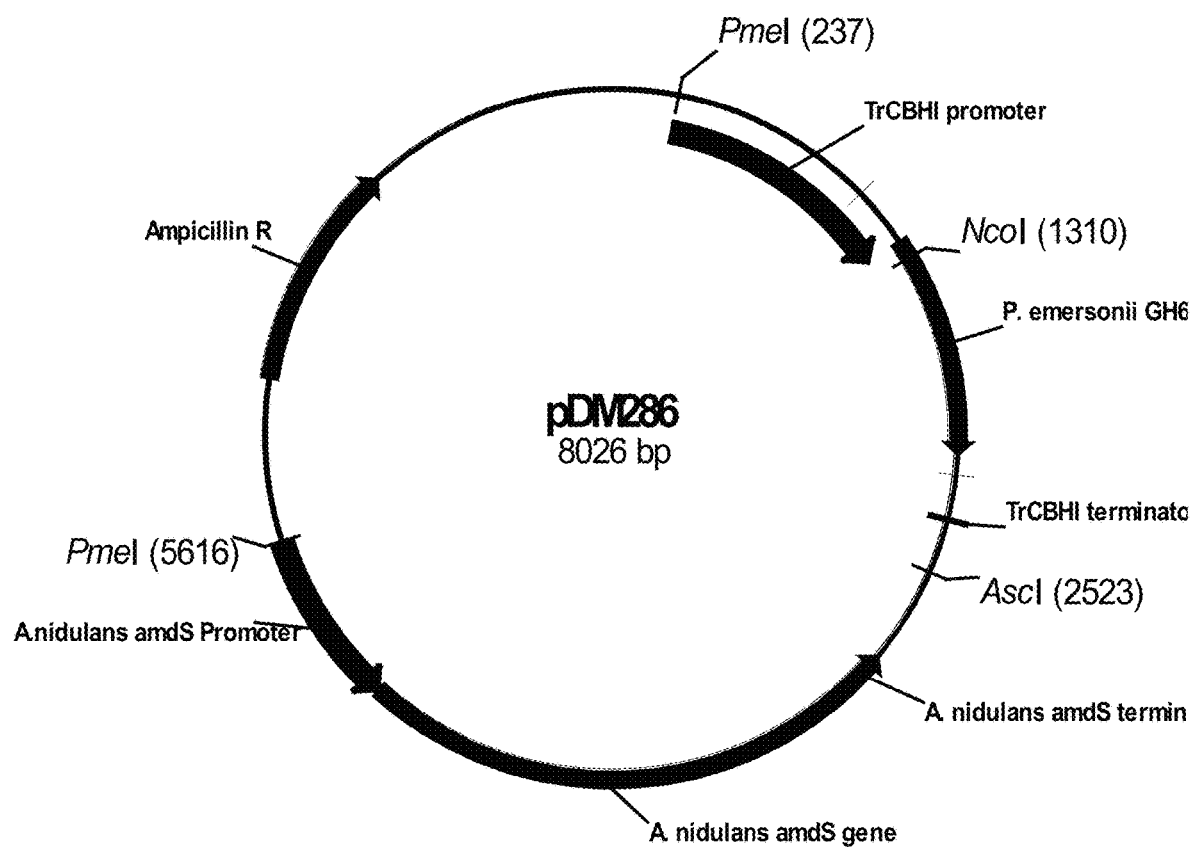
FIG. 4 shows a restriction map of plasmid pDM286.

The 0.9 kb PCR product was inserted into the gel-purified Nco I/Pac I digested pMJ09 using an IN-FUSION™ Advantage PCR Cloning Kit according to the manufacturer's protocol. The IN-FUSION™ reaction was composed of 1× IN-FUSION™ Reaction Buffer, 180 ng of the gel-purified Nco I/Pac I digested pMJ09, 108 ng of the 0.9 kb PCR product, and 1 µl of IN-FUSION™ Enzyme in a 10 µl reaction volume. The reaction was incubated for 15 minutes at 37° C. and 15 minutes at 50° C. After the incubation period 40 µl of TE were added to the reaction. A 2 µl aliquot was used to transform ONE SHOT® TOP10 competent cells according to the manufacturer's protocol. The *E. coli* transformation reactions were spread onto 2XYT plus ampicillin plates. The transformants were screened by sequencing and one clone containing the insert with no PCR errors was identified and designated pDM286 (FIG. 4). Plasmid pDM286 can be digested with Pme I to generate an approximately 5.4 kb fragment for *T. reesei* transformation. The 5.4 kb fragment contains the expression cassette composed of the *T. reesei* Cel7A cellobiohydrolase I gene promoter, *P. emersonii* GH61A polypeptide coding sequence, and *T.* reesei Cel7A cellobiohydrolase I gene terminator. The 5.4 kb fragment also contains the *Aspergillus nidulans* acetamidase (amdS) gene.

Example 10: Generation of a *Trichoderma reesei* Expression Vector Encoding *Aspergillus fumigatus* Beta-Glucosidase (Cel3A) Mutant Gene A variant of the *Aspergillus fumigatus* Family 3A beta-glucosidase containing the substitutions G142S, Q183R, H266Q, and D703G was constructed by performing site-directed mutagenesis on pEJG97 (WO 2005/074647) using a QUIKCHANGE® Multi Site-Directed Mutagenesis Kit (Stratagene, La Jolla, Calif., USA). A summary of the oligos used for the site-directed mutagenesis are shown in Table 1.

The resulting variant plasmid pDFng128-6 was prepared using a BIOROBOT® 9600 (QIAGEN Inc., Valencia, Calif., USA). The variant plasmid construct was sequenced using an Applied Biosystems 3130xl Genetic Analyzer (Applied Biosystems, Foster City, Calif., USA) to verify the changes.

TABLE 1

| Amino acid changes | Primer name | Sequences | Cloning Plasmid Name |
|---|---|---|---|
| F100D | AfBGmutF100DF | ccctttgggtatccgt GACtgtgagctatacc cgcg (SEQ ID NO: 69) | pDFng128-6 |
| S283G | AfBGmutS283GF | cgtcatgagtgactgg GGCgctcaccacagcg gtg (SEQ ID NO: 70) | |
| N456E | AfBGmutN456EF | gggtagtggtactgcc GAGttcccttaccttgt cac (SEQ ID NO: 71) | |
| F512Y | AfBGmutF512YF | gccgactctggagaggt TACatcagtgtcgacggc aac (SEQ ID NO: 72) | |

Two synthetic oligonucleotide primers shown below were designed to PCR amplify the *Aspergillus fumigatus* beta-glucosidase mutant coding sequence from plasmid pDFng128-6. An IN-FUSION™ Cloning Kit was used to clone the fragment directly into the expression vector pMJ09. Bold letters represent coding sequence. The remaining sequence is homologous to insertion sites of pMJ09.

Forward primer:
(SEQ ID NO: 73)
5'-CGGACTGCGCACCATGAGATTCGGTTGGCTCGA-3'

Reverse primer:
(SEQ ID NO: 74)
5'-TCGCCACGGAGCTTACTAGTAGACACGGGGCAGAG-3'

Fifty picomoles of each of the primers above were used in a PCR reaction composed of 50 ng of pDFng128-6, 1× EXPAND® High Fidelity PCR Buffer with MgCl$_2$ (Roche Diagnostics Corporation, Indianapolis, Ind., USA), 0.25 mM each of dATP, dTTP, dGTP, and dCTP, and 2.6 units of EXPAND® High Fidelity Enzyme Mix (Roche Diagnostics Corporation, Indianapolis, Ind., USA) in a final volume of 50 μl. The amplification was performed in an EPPENDORF® MASTERCYCLER® 5333 epgradient S programmed for 1 cycle at 94° C. for 2 minute; 30 cycles each at 94° C. for 15 seconds, 65° C. for 30 seconds, and 68° C. for 1 minute; and a final elongation at 68° C. for 7 minutes. The heat block then went to a 4° C. soak cycle. The reaction products were isolated by 0.7% agarose gel electrophoresis in TBE buffer where an approximately 3.1 kb product band was observed on the gel. The PCR reaction was purified using a QIAQUICK® Gel Extraction Kit according to the manufacturer's instructions.

Plasmid pMJ09 was digested with Nco I and Pac I, isolated by 1.0% agarose gel electrophoresis in TBE buffer, excised from the gel, and extracted using a QIAQUICK® Gel Extraction Kit according to the manufacturer's instructions.

Figure 5:
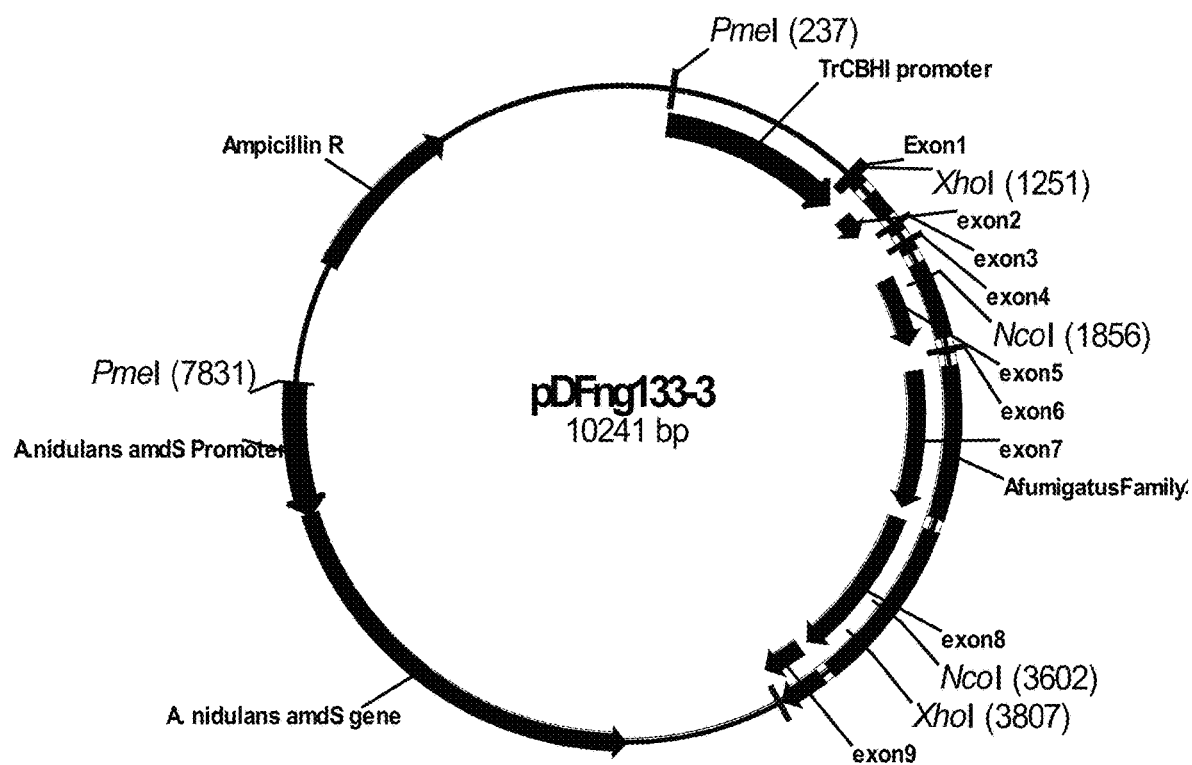
FIG. 5 shows a restriction map of plasmid pDFng113-3.

The 3.1 kb gene fragment and the digested vector were ligated together using an IN-FUSION™ Cloning Kit resulting in pDFng113-3 (FIG. 5) in which transcription of the beta-glucosidase mutant coding sequence was under the control of a promoter from the *Trichoderma reesei* cbhl gene. The ligation reaction (20 μl) was composed of 1× IN-FUSION™ Buffer, 1×BSA, 1 μl of IN-FUSION™ Enzyme (diluted 1:10), 200 ng of the gel-purified Nco I/Pac I digested pMJ09, and 172.2 ng of the purified 3.1 kb PCR product. The reaction was incubated at 37° C. for 15 minutes followed by 50° C. for 15 minutes. Two μl of the reaction was used to transform *E. coli* XL10 SOLOPACK® Gold Supercompetent cells (Stratagene, La Jolla, Calif., USA). The *E. coli* transformation reactions were spread onto 2XYT plus ampicillin plates. An *E. coli* transformant containing pDFng133-3 was prepared using a BIOROBOT® 9600. The *Aspergillus fumigatus* beta-glucosidase mutant insert in pDFng133 was confirmed by DNA sequencing.

Example 11: Construction of Plasmid pSMai139

To construct pSMai139, the *Humicola insolens* endoglucanase V full-length coding region was PCR amplified from pMJ05 (US 2004/0248258 A1) as template with the primers shown below. The underlined portions are Sph I and a Hind III sites introduced by the Car-F2 sense primer. The bold portion is an Eco RI site introduced by the Car-R2 antisense primer.

Car-F2 sense primer:
(SEQ ID NO: 75)
5'-TATAAGCTTAAGCATGCGTTCCTCCCCCCTC-3'

Car-R2 antisense primer:
(SEQ ID NO: 76)
5'-CTGCAGAATTCTACAGGCACTGATGGTACCAG-3'

The amplification reactions (50 μl) were composed of 1× ThermoPol Reaction Buffer (New England Biolabs, Inc., Ipswich, Mass. USA), 0.3 mM dNTPs, 10 ng of pMJ05 DNA, 0.3 μM Car-F2 sense primer, 0.3 μM Car-R2 antisense primer, and 2.5 units of VENT® DNA polymerase (New England Biolabs, Inc., Ipswich, Mass. USA). The reactions were incubated in an EPPENDORF® MASTERCYCLER® 5333 epgradient S programmed for 30 cycles each at 94° C. for 30 seconds, 55° C. for 30 seconds, and 72° C. for 60 seconds (15 minute final extension). The reaction products were isolated by 1.0% agarose gel electrophoresis using TAE buffer where a 900 bp product band was excised from the gel and purified using a QIAQUICK® Gel Extraction Kit according to the manufacturer's instructions. The 900 bp PCR fragment was then digested with Eco RI and Hind III and subjected to a QIAQUICK® PCR Purification Kit (QIAGEN Inc., Valencia, Calif., USA) according to the manufacturer's protocol.

Plasmid pMJ05 was digested with Eco RI and Hind III, isolated by 0.7% agarose gel electrophoresis in TAE buffer, excised from the gel, and extracted using a QIAQUICK® Gel Extraction Kit according to the manufacturer's instructions.

Figure 6:
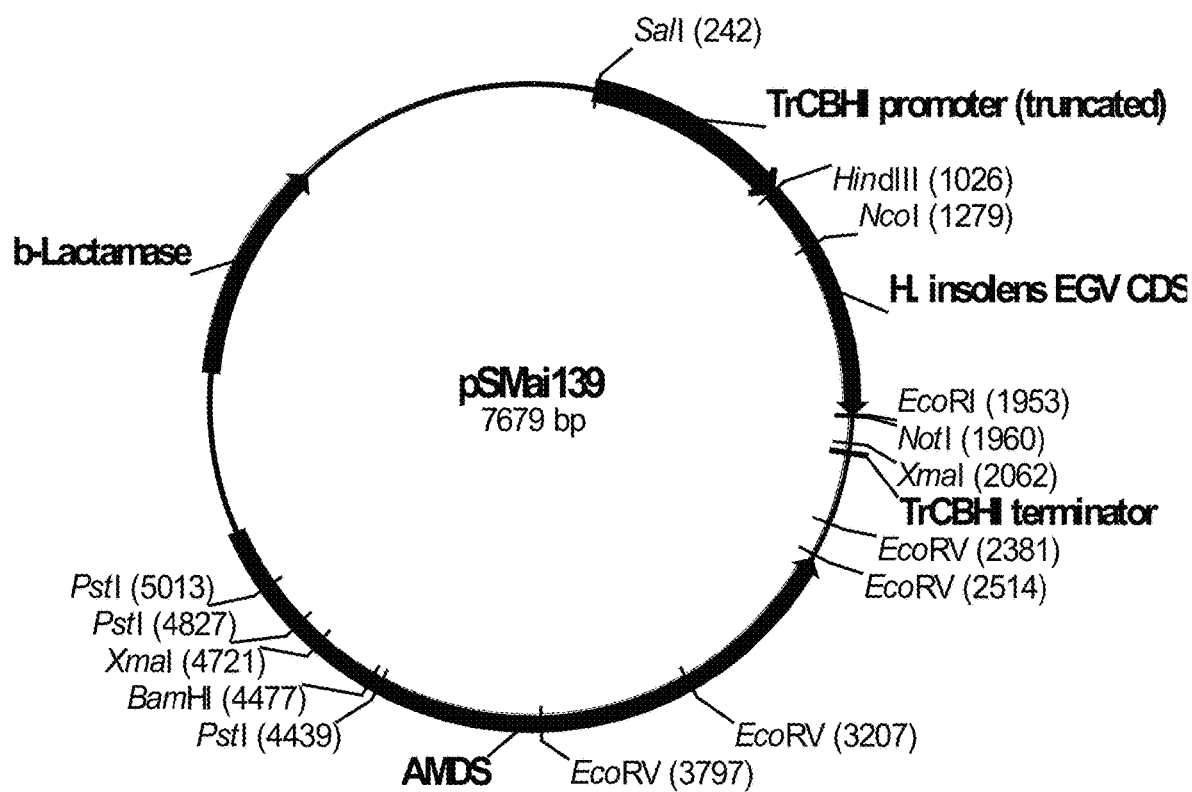
FIG. 6 shows a restriction map of plasmid pSMai139.

The 900 bp Eco RI and Hind III digested PCR fragment was ligated using T4 DNA ligase (Roche, Indianapolis, Ind., USA) into Eco RI and Hind III digested pMJ05. The ligation reaction was composed of 50 ng of the Eco RI and Hind III digested pMJ05, 33 ng of the Eco RI and Hind III digested 0.9 kb PCR fragment, 1× Ligase Buffer (Roche, Indianapolis, Ind., USA), and 2 units of T4 DNA ligase in a final volume of 20 µl. The reaction was incubated at 15° C. for 17 hours and 2 µl of the reaction was used to transform ONE SHOT® TOP10 competent cells according to the manufacturer's protocol. The cells were heat shocked at 42° C. for 30 seconds and 250 µl of SOC medium were added. The tubes were incubated at 37° C., 200 rpm for 1 hour and 250 µl were plated onto 150 mm diameter 2XYT plus ampicillin plates and incubated at 37° C. overnight. The resulting transformants were screened by restriction digestion analysis with Sph I and Bam HI to determine the presence and orientation of the insert and positive clones were sequenced. A clone containing the *Humicola insolens* endoglucanase V coding region with no PCR errors was designated pSMai139 (FIG. 6).

Example 12: Construction of pSMai143 Plasmid

Plasmid pSMai143 was constructed by amplifying 620 bp of the *Trichoderma reesei* cellobiohydrolase Cel6A promoter from *Trichoderma reesei* RutC30 genomic DNA using primers 994148 and 994149 shown below. The underlined portion is a Sal I site introduced by primer 994148. The bold portion is a "CAT" sequence introduced by primer 994149.

```
Primer 994148:
                                     (SEQ ID NO: 77)
5'-ACGCGTCGACGAATTCTAGGCTAGGTATGCGAGGCA-3'

Primer 994149:
                                     (SEQ ID NO: 78)
5'-CATGGTGCAATACACAGAGGGTG-3'
```

The amplification reactions (50 µl) were composed of 1× ThermoPol Reaction Buffer, 0.3 mM dNTPs, 100 ng of *Trichoderma reesei* RutC30 genomic DNA, 0.3 µM 994148 sense primer, 0.3 µM 994149 antisense primer, and 2.5 units of Vent DNA polymerase. The reactions were incubated in an EPPENDORF® MASTERCYCLER® 5333 epgradient S programmed for 30 cycles each at 94° C. for 60 seconds, 55° C. for 60 seconds, and 72° C. for 60 seconds (15 minute final extension). The reaction products were isolated by 1.0% agarose gel electrophoresis using TAE buffer where a 620 bp product band was excised from the gel and purified using a QIAQUICK® Gel Extraction Kit according to the manufacturer's instructions.

Plasmid pSMai139 was digested with Sph I, 3'-protruding end blunted with T4 DNA polymerase and then digested with Sal I. The digested DNA was isolated by 0.7% agarose gel electrophoresis in TAE buffer, excised from the gel, and extracted using a QIAQUICK® Gel Extraction Kit according to the manufacturer's instructions.

Figure 7:
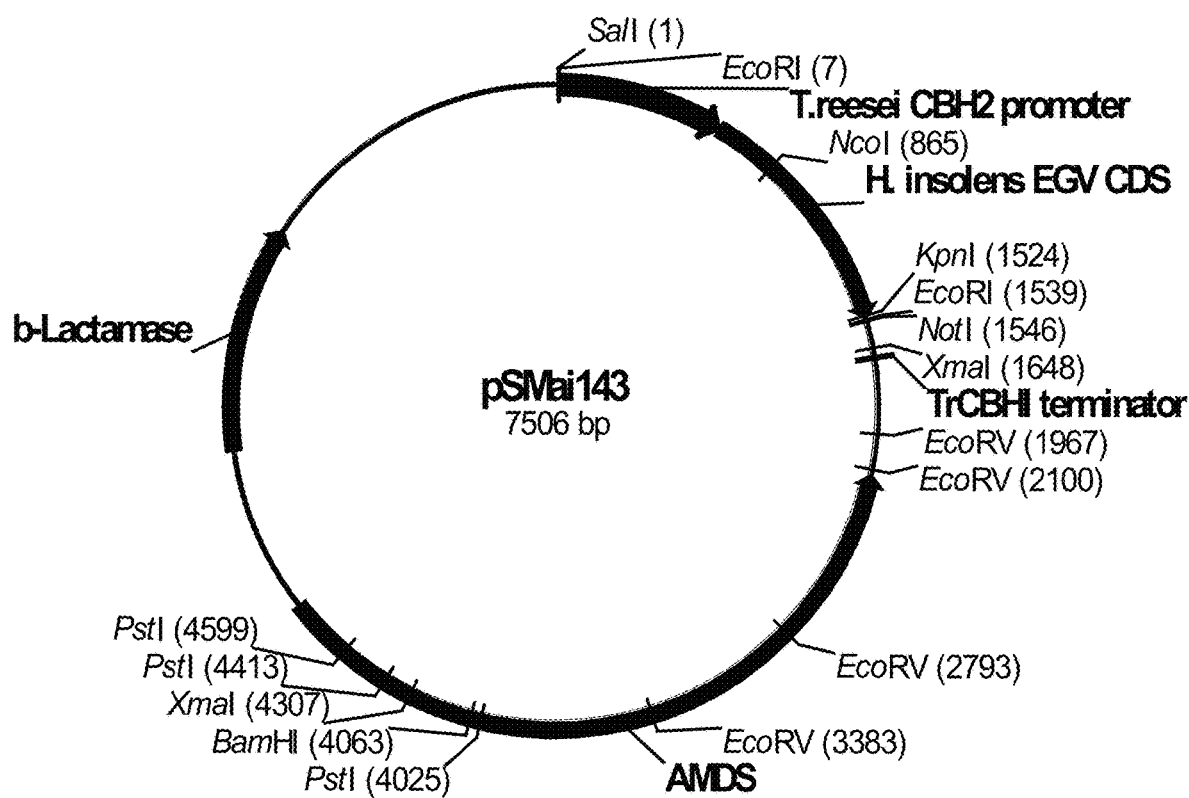
FIG. 7 shows a restriction map of plasmid pSMai143.

The 620 bp Sal I digested PCR fragment was ligated using T4 DNA ligase into Sph I and Sal I digested pSMai139. The ligation reaction was composed of 50 ng of the Sph I and Sal I digested pSMai139, 22 ng of the Sal I digested 0.62 kb PCR fragment, 1× Ligase Buffer, and 2 units of T4 DNA ligase in a final volume of 20 µl. The reaction was incubated at 15° C. for 17 hours and 2 µl of the reaction was used to transform ONE SHOT® TOP10 competent cells according to the manufacturer's protocol. The cells were heat shocked at 42° C. for 30 seconds and 250 µl of SOC medium were added. The tubes were incubated at 37° C., 200 rpm for 1 hour and 250 µl were plated onto 150 mm diameter 2XYT plus ampicillin plates and incubated at 37° C. overnight. The resulting transformants were screened by restriction digestion analysis with Eco RI to determine the presence and orientation of the insert and positive clones were sequenced. A clone containing the *Trichoderma reesei* cellobiohydrolase Cel6A promoter with no PCR errors was designated pSMai143 (FIG. 7).

Example 13: Construction of Plasmid pAG121

Expression vector pAG121 with an Nco I restriction site was constructed by performing site-directed mutagenesis on pSMai143 (Example 12) using a QUIKCHANGE® Site-Directed Mutagenesis Kit (Stratagene, La Jolla, Calif., USA) using the primers shown below. The mutagenesis was performed according to manufacturer's recommendations using 20 ng of plasmid pAG121 and 12.5 µM primers in a final volume of 50 µl.

```
Smai143 SDM Fwd:
                                     (SEQ ID NO: 79)
gtgtattgcaccatggcgttcctcccccctcc Smai143 SDM Rev
                                     (SEQ ID NO: 80)
ggagggggaggaacgccatggtgcaataca
```

The resulting variant plasmid pAG121 was prepared using a BIOROBOT® 9600. The variant plasmid construct was sequenced using an Applied Biosystems 3130xl Genetic Analyzer to verify the changes.

Example 14: Construction of a *Trichoderma reesei* Expression Vector, pSMai229, Encoding an *Aspergillus fumigatus* Beta-Glucosidase (Cel3A) Mutant Gene A *Trichoderma reesei* expression vector, pSMai229, encoding the *Aspergillus fumigatus* beta-glucosidase (Cel3A) mutant coding sequence of Example 9, was constructed from pDFng133-3 (Example 10) and pAG121 (Example 13).

The *Aspergillus fumigatus* beta-glucosidase (Cel3A) mutant coding sequence was PCR amplified from pDFng133-3 using primers 0611689 and 0611690 shown below. The regions in bold represent pAG121 vector homology to the site of insertion for IN-FUSION® cloning.

```
Primer 0611689:
                                     (SEQ ID NO: 81)
CACCCTCTGTGTATTGCACCATGAGATTCGGTTGGCTCGA Primer 0611690:
                                     (SEQ ID NO: 82)
TTCGCCACGGAGCTACTAGTCTAGTAGACACGGGGCAGAG
```

The amplification reaction was composed of 25 ng of pDFng133-3 DNA, 200 µm dNTP's, 0.4 µM primers, 1× PHUSION® Buffer, and 1 unit of PHUSION® Hot Start High Fidelity DNA Polymerase in a final volume of 50 µl. The amplification reaction was incubated in an EPPENDORF® MASTERCYCLER® 5333 epgradient S programmed for 1 cycle at 98° C. for 30 seconds; 30 cycles each at 98° C. for 30 seconds, 56° C. for 30 seconds, and 72° C. for 3 minutes 30 seconds; and 1 cycle at 72° C. for 15 minutes.

Figure 8:
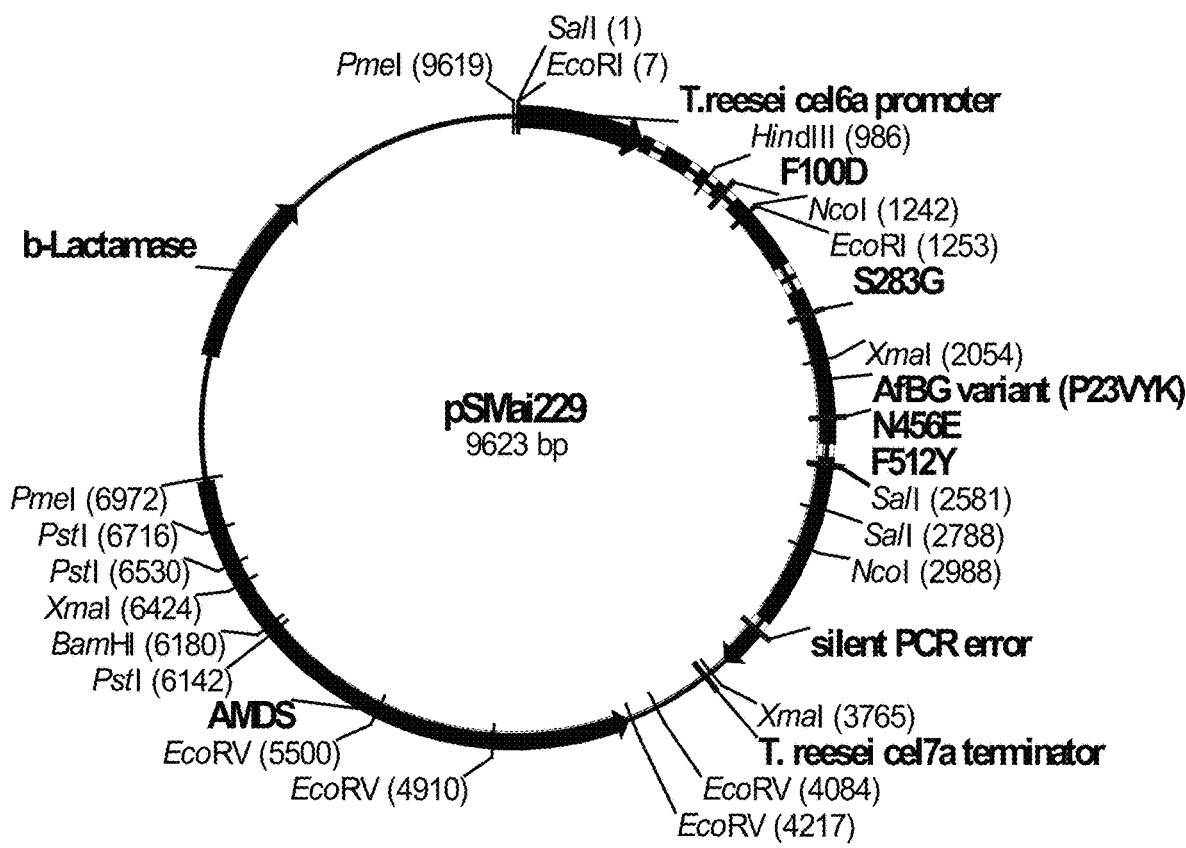
FIG. 8 shows a restriction map of plasmid pSMai229.

PCR products were separated by 1% agarose gel electrophoresis using TAE buffer where a 3100 bp fragment was excised from the gel and purified using a MINELUTE® Gel Extraction Kit according to the manufacturer's instructions. The fragment was then cloned to the largest fragment of pAG121 digested with NcoI and SpeI using an IN-FUSION™ Advantage PCR Cloning Kit resulting in pSMai229 (FIG. 8). The ligation reaction (10 µl) was composed of 1× IN-FUSION™ Buffer, 1 µl of IN-FUSION™ Enzyme, 100 ng of pAG121 digested with Nco I and Spe I, and 142 ng of 3100 bp purified PCR product. The reaction was incubated at 37° C. for 15 minutes followed by 15 minutes at 50° C. After diluting the reaction mix with 50 µl of TE buffer (pH 8), 2.5 µl of the reaction was used to transform *E. coli* ONE SHOT® TOP10 competent cells according to the manufacturer's protocol. An *E. coli* transformant containing pSMai229 was detected by restriction digestion and plasmid DNA was prepared using a BIOROBOT® 9600. The *Aspergillus fumigatus* beta-glucosidase (Cel3A) mutant insert in pSMai229 was confirmed by DNA sequencing.

Example 15: Co-Transformation of pDM286 and pSMai229 into *Trichoderma reesei* 981-O-8.5 #10B+Ku70 #19L3

Protoplast preparation and transformation of *Trichoderma reesei* strain 981-O-8.5 #10B+Ku70 #19L3 was performed as described in Example 2.

Approximately 100 µg of pDM286 and pSMai229 were digested with Pme I. Each digestion reaction was purified by 1% agarose gel electrophoresis in TAE buffer, a DNA band was excised from the gel, and extracted using a QIAQUICK® Gel Extraction Kit. Transformation was performed by adding 0.7-1.7 µg of Pme I digested and gel-purified pSMai229 and 0.7-2.0 µg of pDM286 to 100 µl of *Trichoderma reesei T. reesei* 981-O-8 #10B+Ku70 #19L3 protoplast solution and mixed gently. PEG buffer (250 µl) was added, mixed, and incubated at 34° C. for 30 minutes. STC (4 ml) was then added, mixed, and plated onto COVE plates. The plates were incubated at 28° C. for 7-10 days. After a single round of spore purification on COVE2 plus 10 mM Uridine plates, 362 transformants were grown in 125 ml baffled shake flasks containing 25 ml of cellulase-inducing medium for 5 days at 28° C. with agitation at 200 rpm. Culture broth samples were removed 5 days post-inoculation, centrifuged at 2000 rpm for 20 minutes, and the supernatants transferred to new tubes and stored at −20° C. until enzyme assay.

The supernatants were assayed for beta-glucosidase activity using p-nitrophenyl-beta-D-glucopyranoside as substrate. Briefly, culture supernatants were diluted appropriately in 0.1 M succinate-0.01% TRITON® X-100 pH 5.0 buffer (sample buffer) followed by a series dilution from 0-fold to 1/3-fold to 1/9-fold of the diluted sample. *T. reesei* RutC30 fermentation broth was initially diluted 1/64 followed with 2-fold dilution steps down to a 16-fold dilution in the sample buffer to establish the assay linear range. A total of 20 µl of each dilution was transferred to a 96-well flat bottom plate. Two hundred microliters of a 1 mg/ml p-nitrophenyl-beta-D-glucopyraniside substrate in 0.1 M succinate pH 5.0 buffer was added to each well and then incubated at ambient temperature for 45 minutes. Upon completion of the incubation period 50 µl of quenching solution (1 M Tris pH 9 buffer) was added per well. An endpoint was measured at an optical density of 405 nm for the 96-well plate. Sample activity was determined according to the following equation: $(((OD405/ec)*1 \times 10^6)/\text{incubation time})/\text{sample volume}$, where ec=17,749, incubation time=45 minutes, and sample volume=0.02 ml.

A number of transformants showed beta-glucosidase activity several-fold higher than that of *Trichoderma reesei* 981-O-8.5 #10B+Ku70 #19L3. All samples with beta-glucosidase activity values greater than 7000 µM/min/ml were analyzed by SDS-PAGE using CRITERION® 8-16% Tris-HCl gels (Bio-Rad Laboratories, Inc., Hercules, Calif., USA) with a CRITERION® Cell (Bio-Rad Laboratories, Inc. Hercules, Calif., USA) to determine *Penicillium emersonii* GH61A polypeptide expression. Five µl of day 5 samples were suspended in 2× concentration of Laemmli Sample Buffer (Bio-Rad Laboratories, Hercules, Calif., USA) and heated at 95° C. for 5 minutes in the presence of 5% beta-mercaptoethanol. All samples were loaded onto the CRITERION® 8-16% Tris-HCl gels and subjected to electrophoresis in 1× Tris/Glycine/SDS running buffer (Bio-Rad Laboratories, Hercules, Calif., USA). The resulting gels were stained with BIO-SAFE® Coomassie Stain (Bio-Rad Laboratories, Hercules, Calif., USA). SDS-PAGE profiles of the cultures showed the presence of both the *Aspergillus fumigatus* beta-glucosidase variant and the *Penicillium emersonii* GH61A in samples #1, 64, 79, 82, 83, 116, 147, 167, 193, 198, 210, 219, 908, 922, 928, 930, 935, 951, 963, and 980.

Example 16: Construction of pAG57

The *Aspergillus fumigatus* strain NN051616 GH3 beta-xylosidase (SEQ ID NO: 15 [DNA sequence] and SEQ ID NO: 16 [deduced amino acid sequence]) was recombinantly prepared according to the following procedure.

Two synthetic oligonucleotide primers shown below were designed to PCR amplify the *Aspergillus fumigatus* beta-xylosidase gene from genomic DNA. Genomic DNA was prepared as described in Example 1. An IN-FUSION™ Advantage PCR Cloning Kit was used to clone the fragment directly into the expression vector, pAILo2 (WO 2005/074647), without the need for restriction digests and ligation.

```
Forward primer:
                                          (SEQ ID NO: 83)
5'-ACTGGATTTACCATGGCGGTTGCCAAATCTATTGCT-3'

Reverse primer:
                                          (SEQ ID NO: 84)
5'-TCACCTCTAGTTAATTAATCACGCAGACGAAATCTGCT-3'
```

Bold letters represent coding sequence. The remaining sequence is homologous to the insertion sites of pAILo2.

Fifteen picomoles of each of the primers above were used in a PCR reaction containing 250 ng of *Aspergillus fumigatus* genomic DNA, 1× EXPAND® High Fidelity PCR Buffer with MgCl$_2$, 1 µl of a 10 mM blend of dATP, dTTP, dGTP, and dCTP, and 0.75 units of EXPAND® High Fidelity Enzyme Mix in a final volume of 50 µl. The amplification was performed using an EPPENDORF® MASTERCYCLER® 5333 epgradient S programmed for 1 cycle at 94° C. for 2 minutes; 10 cycles each at 94° C. for 15 seconds, 56.5° C. for 30 seconds, and 72° C. for 2 minutes; and 20 cycles each at 94° C. for 15 seconds, 56.5° C. for 30 seconds, and 72° C. for 2 minutes plus 5 seconds per successive cycle. The heat block was then held at 72° C. for 7 minutes followed by a 4° C. soak cycle.

The reaction products were isolated by 1.0% agarose gel electrophoresis using TAE buffer where a 2.4 kb product band was excised from the gel and purified using a MIN-ELUTE® Gel Extraction Kit according to the manufacturer's instructions.

Figure 9:
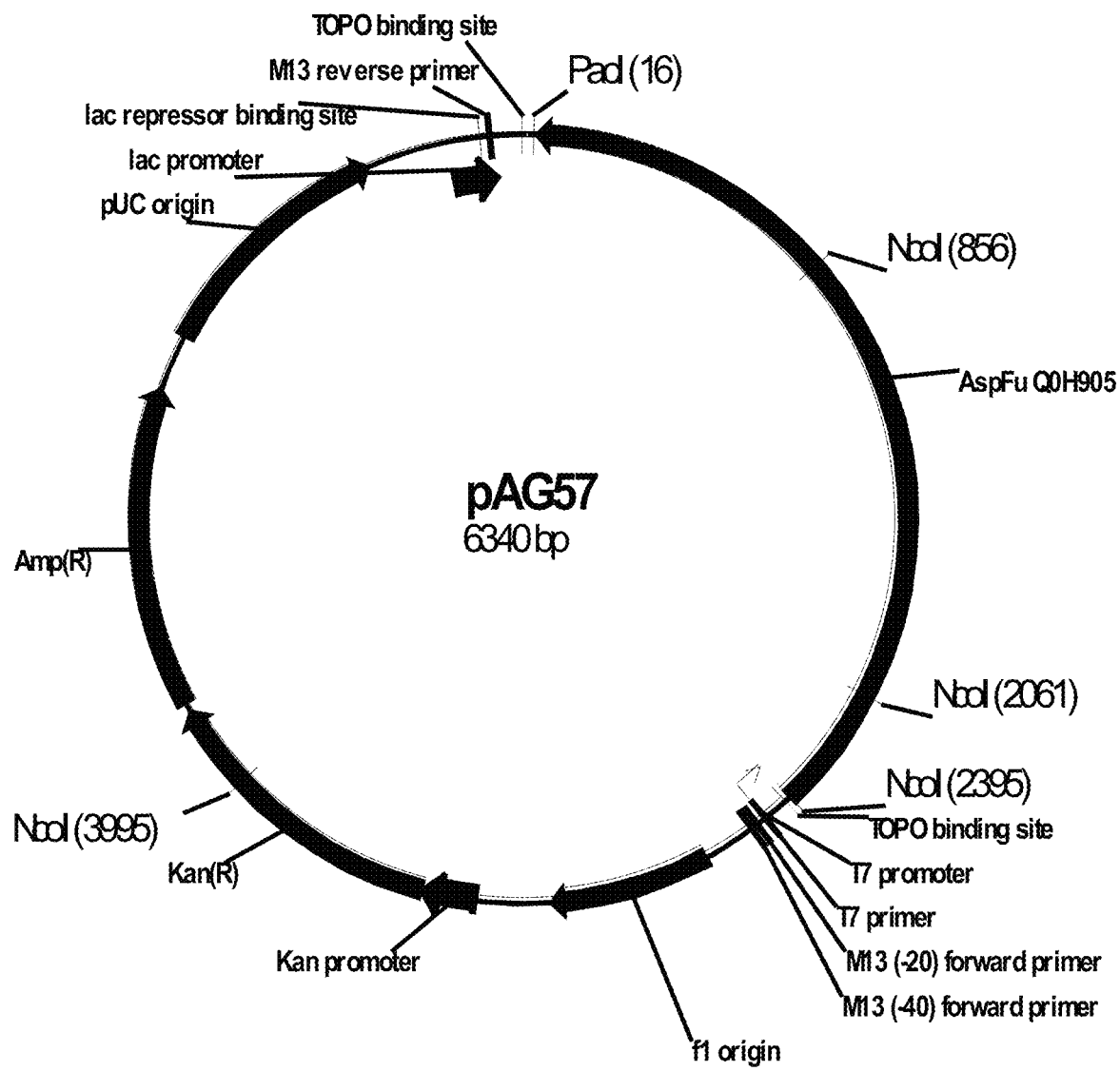
FIG. 9 shows a restriction map of plasmid pAG57.

The fragment was then cloned into pAlLo2 using an IN-FUSION™ Advantage PCR Cloning Kit. The vector was digested with Nco 1 and Pac 1. The fragment was purified by 1% agarose gel electrophoresis using TAE buffer, excised from the gel, and extracted using a QIAQUICK® Gel Extraction Kit. The gene fragment and the digested vector were combined together in a reaction resulting in the expression plasmid pAG57, in which transcription of the *Aspergillus fumigatus* beta-xylosidase coding sequence was under the control of the NA2-tpi promoter (a hybrid of the promoters from the genes for *Aspergillus niger* neutral alpha-amylase and *Aspergillus oryzae* triose phosphate isomerase). The reaction (20 µl) was composed of 1× IN-FUSION™ Buffer, 1× BSA, 1 µl of IN-FUSION™ Enzyme (diluted 1:10), 182 ng of pAlLo2 digested with Nco I and Pac 1, and 97.7 ng of the *Aspergillus fumigatus* beta-xylosidase purified PCR product. The reaction was incubated at 37° C. for 15 minutes followed by 15 minutes at 50° C. The reaction was diluted with 40 µl of TE buffer and 2.5 µl of the diluted reaction were used to transform *E. coli* TOP10 Competent cells. An *E. coli* transformant containing pAG57 (FIG. 9) was identified by restriction enzyme digestion and plasmid DNA was prepared using a BIOROBOT® 9600. The pAG57 plasmid construct was sequenced using an Applied Biosystems 3130xl Genetic Analyzer to verify the sequence.

Example 17: Construction of pDFng124-1 Expressing an *Aspergillus fumigatus* Beta-Xylosidase Two synthetic oligonucleotide primers shown below were designed to PCR amplify the *Aspergillus fumigatus* beta-xylosidase from pAG57 (Example 16). An IN-FUSION™ Advantage PCR Cloning Kit was used to clone the fragment directly into the expression vector, pMJ09, without the need for restriction digestion and ligation.

```
Forward primer:
                                   (SEQ ID NO: 85)
5'-CGGACTGCGCACCATGGCGGTTGCCAAATC-3'

Reverse primer:
                                   (SEQ ID NO: 86)
5'-TCGCCACGGAGCTTATCACGCAGACGAAATCT-3'
```

Bold letters represent coding sequence. The remaining sequence was homologous to insertion sites of pMJ09.

Fifty picomoles of each of the primers above were used in a PCR reaction composed of 100 ng of pAG57, 1× EXPAND® High Fidelity PCR buffer with MgCl$_2$, 0.25 mM each of dATP, dTTP, dGTP, and dCTP, and 2.6 units of EXPAND® Enzyme Mix in a final volume of 50 µl. The amplification was performed using an EPPENDORF® MASTERCYCLER® 5333 epgradient S programmed for 1 cycle at 94° C. for 2 minutes; 30 cycles each at 94° C. for 15 seconds, 65° C. for 30 seconds, and 72° C. for 2 minutes; and a final elongation at 72° C. for 7 minutes. The heat block then went to a 4° C. soak cycle.

The reaction products were isolated by 0.7% agarose gel electrophoresis in TBE buffer where a 2.4 kb product band was excised from the gel and purified using a QIAQUICK® Gel Extraction Kit according to the manufacturer's instructions.

Plasmid pMJ09 was digested with Nco I and Pac I, isolated by 0.7% agarose gel electrophoresis in TBE buffer, and purified using a QIAQUICK® Gel Extraction Kit according to the manufacturer's instructions.

Figure 10:
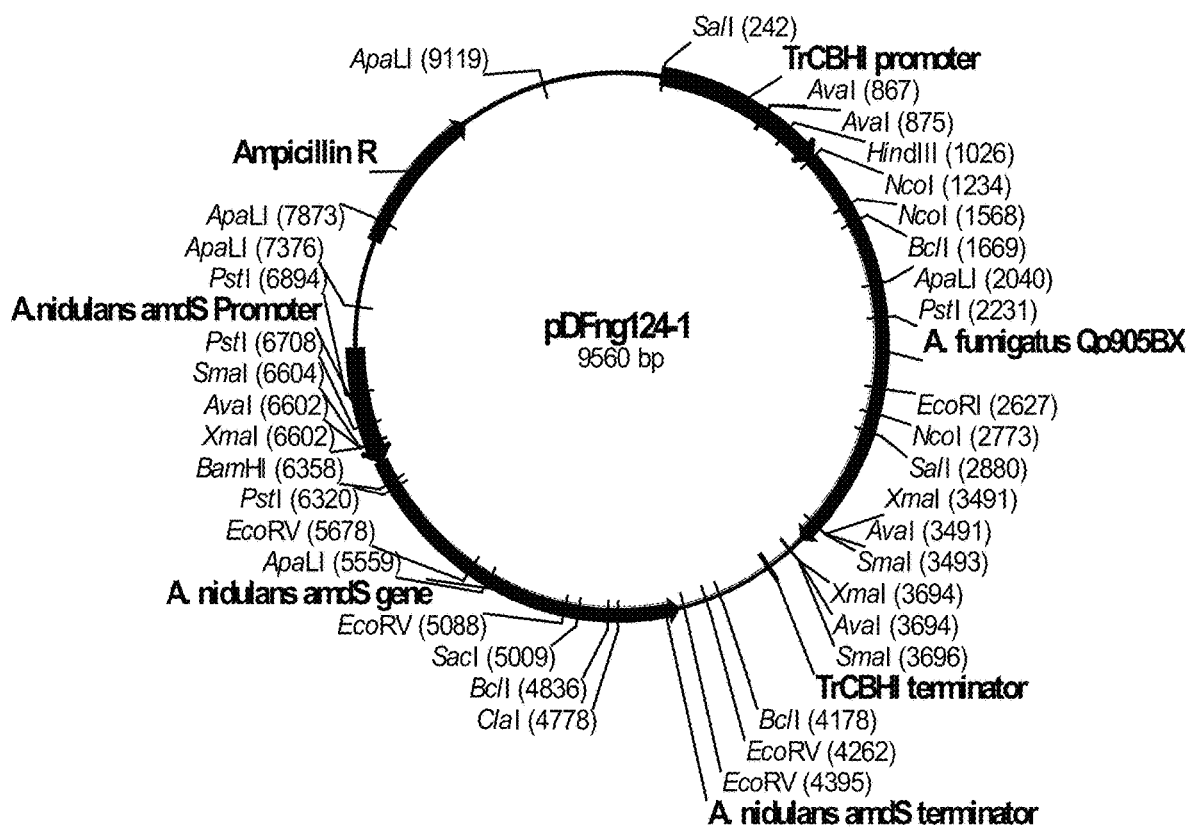
FIG. 10 shows a restriction map of plasmid pDFng124-1.

The gene fragment and the digested vector were ligated together using an IN-FUSION™ Advantage PCR Cloning Kit resulting in pDFng124-1 (FIG. 10) in which transcription of the beta-xylosidase coding sequence was under the control of the *Trichoderma reesei* cbhl gene promoter. The ligation reaction (20 µl) was composed of 1× IN-FUSION™ Buffer, 1 µl of IN-FUSION™ Enzyme (diluted 1:10), 200 ng of pMJ09 digested with Nco I and Pac I, and 100 ng of the purified beta-xylosidase PCR product. The reaction was incubated at 37° C. for 15 minutes followed by 50° C. for 15 minutes. Two µl of the reaction were used to transform *E. coli* XL10 SOLOPACK® Gold Supercompetent cells according to manufacturer's instructions. An *E. coli* transformant containing pDFng124-1 was prepared using a BIOROBOT® 9600. The *Aspergillus fumigatus* beta-xylosidase insert in pDFng124-1 was confirmed by DNA sequencing.

Example 18: Construction pSaMe-AFGH10 Expressing an *Aspergillus fumigatus* Xylanase Two synthetic oligonucleotide primers shown below were designed to PCR amplify the *Aspergillus fumigatus* GH10 xylanase from pHyGe001 (WO 2006/078256). An IN-FUSION™ Advantage PCR Cloning Kit was used to clone the fragment directly into the expression vector, pMJ09, without the need for restriction digestion and ligation.

```
Forward primer:
                                   (SEQ ID NO: 87)
5'-CGGACTGCGCACCATGGTCCATCTATCTTCATT-3'

Reverse primer:
                                   (SEQ ID NO: 88)
5'-TCGCCACGGAGCTTATTACAGGCACTGTGAGTACC-3'
```

Bold letters represent coding sequence. The remaining sequence was homologous to the insertion sites of pMJ09.

Fifty picomoles of each of the primers above were used in a PCR reaction composed of 50 ng of pHYGE001, 1 µl of a 10 mM blend of dATP, dTTP, dGTP, and dCTP, 5 µl of 10× ACCUTAQ™ DNA Polymerase Buffer (Sigma-Aldrich, St. Louis, Mo., USA), and 5 units of ACCUTAQ™ DNA Polymerase (Sigma-Aldrich, St. Louis, Mo., USA) in a final volume of 50 µl. An EPPENDORF® MASTERCYCLER® 5333 epgradient S was used to amplify the DNA fragment programmed for 1 cycle at 95° C. for 2 minutes; and 30 cycles each at 94° C. for 15 seconds, 55° C. for 30 seconds, and 68° C. for 1 minute. After the 30 cycles, the reaction was incubated at 72° C. for 10 minutes and then cooled to 4° C. until further processing.

The reaction products were isolated by 1.0% agarose gel electrophoresis using TAE buffer where a 1.4 kb product band was excised from the gel and purified using a QIA-QUICK® Gel Extraction Kit according to the manufacturer's instructions.

Figure 11:
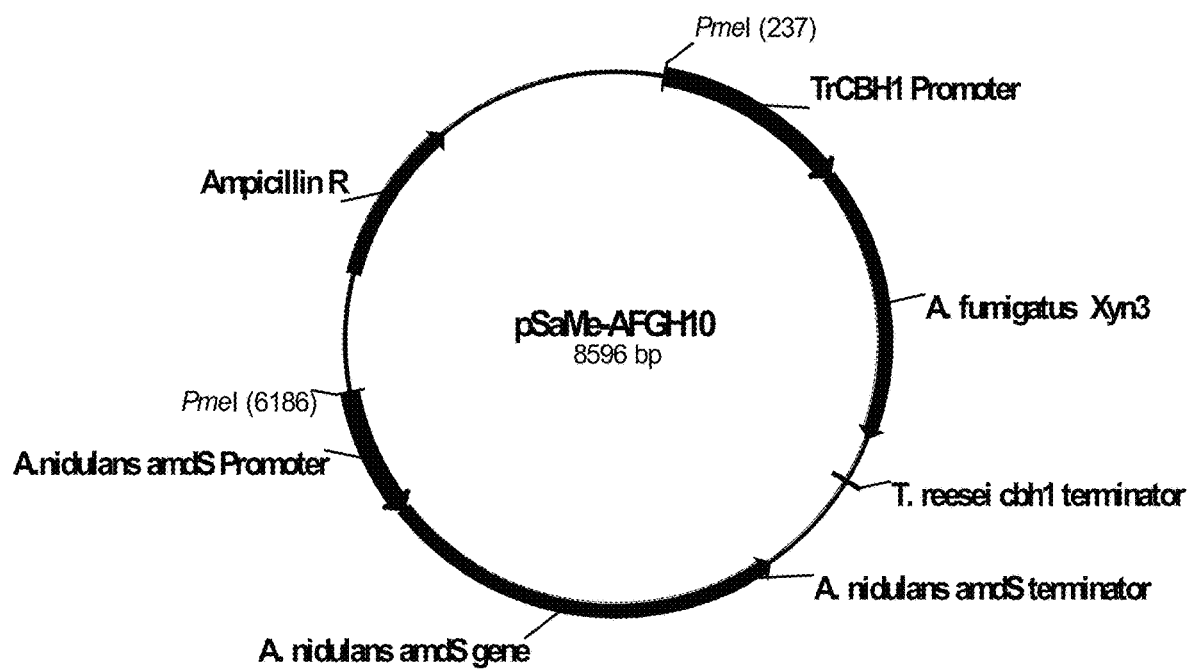
FIG. 11 shows a restriction map of plasmid pSaMe-AFGH10.

The 1.4 kb fragment was then cloned into pMJ09 using an IN-FUSION™ Cloning Kit. Plasmid pMJ09 was digested with Nco I and Pac I and purified by agarose gel electrophoresis as described above. The gene fragment and the digested vector were ligated together in a reaction resulting in the expression plasmid pSaMe-AfGH10 in which transcription of the xylanase coding sequence was under the control of the *T. reesei* cbhl gene promoter. The ligation reaction (50 µl) was composed of 1× IN-FUSION™ Buffer, 1× BSA, 1 µl of IN-FUSION™ enzyme (diluted 1:10), 100 ng of pMJ09 digested with Nco I and Pac I, and 100 ng of the *Aspergillus fumigatus* xylanase purified PCR product. The reaction was incubated at room temperature for 30 minutes. One µl of the reaction was used to transform *E. coli* XL10 SOLOPACK® Gold cells. An *E. coli* transformant containing pSaMe-AfGH10 (FIG. 11) was detected by restriction enzyme digestion and plasmid DNA was prepared using a BIOROBOT® 9600. DNA sequencing of the *Aspergillus fumigatus* xylanase coding sequence from pSaMe-AfGH10 was performed using dye-terminator chemistry (Giesecke et al., 1992, *Journal of Virology Methods* 38: 47-60) and primer walking strategy.

Example 19: Generation of *Trichoderma reesei* RutC30 Strain Expressing *Aspergillus fumigatus* Xylanase and *Aspergillus fumigatus* Beta-Xylosidase Protoplast preparation and transformation of *Trichoderma reesei* strain RutC30 was performed as described in Example 2.

Approximately 100 µg of pSaMe-AFGH10 and pDFng124-1 were digested with Pme I. Each digestion reaction was purified by 0.65% agarose gel electrophoresis in TAE buffer, a DNA band was excised from the gel, and extracted using a QIAQUICK® Gel Extraction Kit. Transformation was performed by adding 2 µg of Pme I digested and gel-purified pDFng124-1 and 1.72 µg of pSaMe-AfGH10 to 100 µl of *Trichoderma reesei* strain RutC30 protoplast solution and mixed gently. PEG buffer (250 µl) was added, mixed, and incubated at 34° C. for 30 minutes. STC (6 ml) was then added, mixed, and plated onto COVE plates. The plates were incubated at 28° C. for 7-10 days. After a single round of spore purification on COVE2 plus 10 mM uridine plates, 200 transformants were grown in 125 ml baffled shake flasks containing 25 ml of cellulase-inducing medium for 5 days at 28° C. with agitation at 200 rpm. Culture broth samples were removed 5 days post-inoculation, centrifuged at 2000 rpm for 20 minutes, and the supernatants transferred to new tubes and stored at −20° C. until enzyme assay.

Three to five µl of each supernatant were combined with 5 to 6 µl of Laemelli sample buffer (Bio-Rad Laboratories, Hercules, Calif., USA) with 5% beta-mercaptoethanol in a 0.2 ml microcentrifuge tube and boiled for 2 minutes at 95° C. in an EPPENDORF® MASTERCYCLER® 5333 epgradient S. Samples were analyzed by SDS-PAGE using a CRITERION® 8-16% Tris-HCl Gel according to the manufacturer's instructions and 10 µl of PRECISION PLUS™ All Blue Protein Standards (Bio-Rad Laboratories, Hercules, Calif., USA). Gels were stained with BIO-SAFE® Coomassie Stain.

Four strains were selected based on high expression of beta-xylosidase and xylanase polypeptide and were spore purified by adding spores collected on a 10 µl inoculation loop to 1.5 ml of 0.01% TWEEN® 20. Spore dilutions of 1:1500 and 1:150 were spread onto 150 mm COVE plates and cultured for 4 days at 28° C. Four spore isolates per strain (total of 16 isolates) were obtained and transferred to COVE2+10 mM uridine plates and cultivated at 28° C. for 9 days. The shake flask and SDS-PAGE procedures were repeated for the first round spore isolates. Eight strains were selected based on high expression of beta-xylosidase and xylanase polypeptide and were spore purified a second time as described above resulting in four spore isolates per strain (total of 32 isolates). The shake flask and SDS-PAGE procedures were repeated for the second round spore isolates. The final strain was selected based on high expression of beta-xylosidase and xylanase polypeptide and designated O6HY4.

Example 20: Pretreated Corn Stover Hydrolysis Assay

Corn stover was pretreated at the U.S. Department of Energy National Renewable Energy Laboratory (NREL) using 1.4 wt % sulfuric acid at 165° C. and 107 psi for 8 minutes. The water-insoluble solids in the pretreated corn stover (PCS) contained 56.5% cellulose, 4.6% hemicelluloses, and 28.4% lignin. Cellulose and hemicellulose were determined by a two-stage sulfuric acid hydrolysis with subsequent analysis of sugars by high performance liquid chromatography using NREL Standard Analytical Procedure #002. Lignin was determined gravimetrically after hydrolyzing the cellulose and hemicellulose fractions with sulfuric acid using NREL Standard Analytical Procedure #003.

Milled unwashed PCS was prepared by milling whole slurry PCS in a Cosmos ICMG 40 wet multi-utility grinder (EssEmm Corporation, Tamil Nadu, India).

The hydrolysis of PCS was conducted using 2.2 ml deep-well plates (Axygen, Union City, Calif., USA) in a total reaction volume of 1.0 ml. The hydrolysis was performed with 50 mg of insoluble PCS solids per ml of 50 mM sodium acetate pH 5.0 buffer containing 1 mM manganese sulfate and various protein loadings of various enzyme compositions (expressed as mg protein per gram of cellulose). Enzyme compositions were prepared and then added simultaneously to all wells in a volume ranging from 50 µl to 200 µl, for a final volume of 1 ml in each reaction. The plates were then sealed using an ALPS-300™ plate heat sealer (Abgene, Epsom, United Kingdom), mixed thoroughly, and incubated at a specific temperature for 72 hours. All experiments reported were performed in triplicate.

Following hydrolysis, samples were filtered using a 0.45 µm MULTISCREEN® 96-well filter plate (Millipore, Bedford, Mass., USA) and filtrates analyzed for sugar content as described below. When not used immediately, filtered aliquots were frozen at −20° C. The sugar concentrations of samples diluted in 0.005 M $H_2SO_4$ were measured using a 4.6×250 mm AMINEX® HPX-87H column (Bio-Rad Laboratories, Inc., Hercules, Calif., USA) by elution with 0.05% w/w benzoic acid-0.005 M $H_2SO_4$ at 65° C. at a flow rate of 0.6 ml per minute, and quantitation by integration of the glucose, cellobiose, and xylose signals from refractive index detection (CHEMSTATION®, AGILENT® 1100 HPLC, Agilent Technologies, Santa Clara, Calif., USA) calibrated by pure sugar samples. The resultant glucose and cellobiose equivalents were used to calculate the percentage of cellulose conversion for each reaction.

Glucose, cellobiose, and xylose were measured individually. Measured sugar concentrations were adjusted for the appropriate dilution factor. In case of unwashed PCS, the net concentrations of enzymatically-produced sugars were determined by adjusting the measured sugar concentrations for corresponding background sugar concentrations in unwashed PCS at zero time points. All HPLC data processing was performed using MICROSOFT EXCEL™ software (Microsoft, Richland, Wash., USA).

The degree of cellulose conversion to glucose was calculated using the following equation: % conversion=(glucose concentration/glucose concentration limit digest)×100. To calculate total conversion the glucose and cellobiose values were combined. The degree of total cellulose conversion was calculated using the following equation: % conversion=[glucose concentration]/[(glucose concentration in a limit digest]×100. In order to calculate % conversion, a 100% conversion point was set based on a cellulase control (50 mg of *Trichoderma reesei* cellulase per gram cellulose), and all values were divided by this number and then multiplied by 100. Triplicate data points were averaged and standard deviation was calculated.

An enzyme composition comprising an *Aspergillus fumigatus* cellobiohydrolase I; an *Aspergillus fumigatus* cellobiohydrolase II; an *Aspergillus fumigatus* beta-glucosidase variant; a *Penicillium* sp. GH61 polypeptide having cellulolytic enhancing activity, an *Aspergillus fumigatus* xylanase, and an *Aspergillus fumigatus* beta-xylosidase (designated "enzyme composition #1") was compared to an enzyme composition comprising a blend of an *Aspergillus aculeatus* GH10 xylanase (WO 94/021785) and a *Trichoderma reesei* cellulase preparation containing *Aspergillus fumigatus* beta-glucosidase (WO 2005/047499) and *Thermoascus aurantiacus* GH61A polypeptide (WO 2005/074656) (designated "enzyme composition #2").

Figure 12:
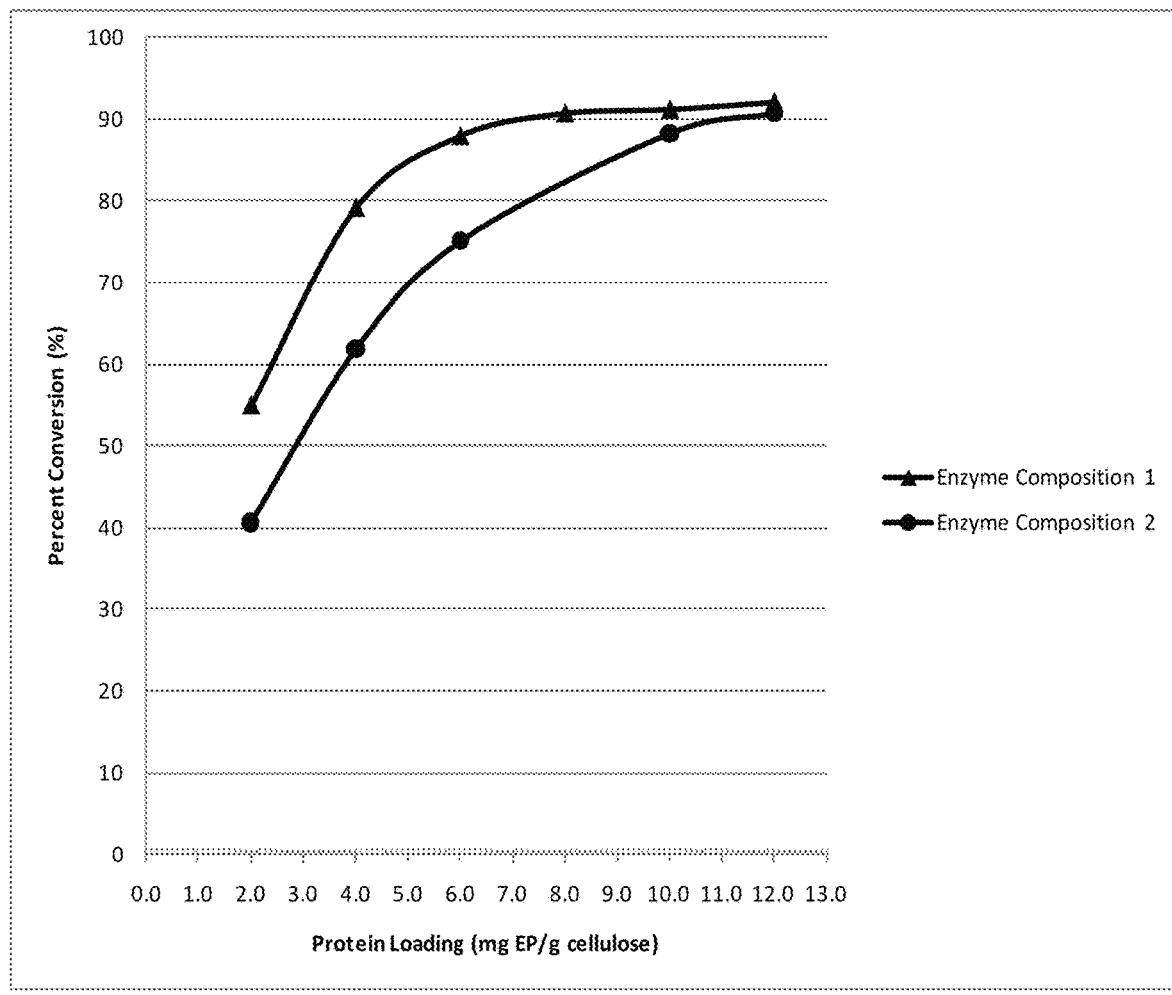
FIG. 12 shows a comparison of percent conversion of pretreated corn stover (PCS) by an enzyme composition comprising an *Aspergillus fumigatus* cellobiohydrolase I; an *Aspergillus fumigatus* cellobiohydrolase II; an *Aspergillus fumigatus* beta-glucosidase variant; a *Penicillium* sp. GH61 polypeptide having cellulolytic enhancing activity, an *Aspergillus fumigatus* xylanase, and an *Aspergillus fumigatus* beta-xylosidase ("enzyme composition #1") to an enzyme composition comprising a blend of an *Aspergillus aculeatus* GH10 xylanase and a *Trichoderma reesei* cellulase preparation containing *Aspergillus fumigatus* beta-glucosidase and *Thermoascus aurantiacus* GH61A polypeptide ("enzyme composition #2").

Upon completion of the hydrolysis assay, a Protein Loading (mg EP/g cellulose) versus Percent Conversion (%) graph was generated. Using linear interpolation the protein loading required to reach a certain percent conversion can be determined. In this case, 80% conversion of glucan to glucose equivalents was chosen to determine relative improvements of enzyme composition 1 as compared to enzyme composition 2. The results of this assay as shown in FIG. 12 indicated that enzyme composition 1 is able to reach 80% conversion with 4.1 mg EP/g cellulose, whereas enzyme composition 2 is able to reach the same conversion target with 7.3 mg EP/g cellulose. This represents a 1.78 fold improvement in performance per milligram of protein for enzyme composition 1 over enzyme composition 2 or a 1.78 fold reduction in protein requirement to reach 80% conversion.

The present invention is further described by the following numbered paragraphs:

[1] An enzyme composition, comprising: (i) an *Aspergillus fumigatus* cellobiohydrolase I; (ii) an *Aspergillus fumigatus* cellobiohydrolase II; (iii) an *Aspergillus fumigatus* beta-glucosidase or variant thereof; and (iv) a *Penicillium* sp. GH61 polypeptide having cellulolytic enhancing activity; or homologs thereof.

[2] The enzyme composition of paragraph 1, wherein the *Aspergillus fumigatus* cellobiohydrolase I or homolog thereof is selected from the group consisting of: (i) a cellobiohydrolase I comprising or consisting of the mature polypeptide of SEQ ID NO: 2; (ii) a cellobiohydrolase I comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 2; (iii) a cellobiohydrolase I encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 1; and (iv) a cellobiohydrolase I encoded by a polynucleotide that hybridizes under at least high stringency conditions, e.g., very high stringency conditions, with the mature polypeptide coding sequence of SEQ ID NO: 1 or the full-length complement thereof.

[3] The enzyme composition of paragraph 1, wherein the *Aspergillus fumigatus* cellobiohydrolase II or homolog thereof is selected from the group consisting of: (i) a cellobiohydrolase II comprising or consisting of the mature polypeptide of SEQ ID NO: 4; (ii) a cellobiohydrolase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 4; (iii) a cellobiohydrolase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 3; and (iv) a cellobiohydrolase II encoded by a polynucleotide that hybridizes under at least high stringency conditions, e.g., very high stringency conditions, with the mature polypeptide coding sequence of SEQ ID NO: 3 or the full-length complement thereof.

[4] The enzyme composition of paragraph 1, wherein the *Aspergillus fumigatus* beta-glucosidase or homolog thereof is selected from the group consisting of: (i) a beta-glucosidase comprising or consisting of the mature polypeptide of SEQ ID NO: 6; (ii) a beta-glucosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 6; (iii) a beta-glucosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 5; and (iv) a beta-glucosidase encoded by a polynucleotide that hybridizes under at least high stringency conditions, e.g., very high stringency conditions, with the mature polypeptide coding sequence of SEQ ID NO: 5 or the full-length complement thereof.

[5] The enzyme composition of paragraph 1, wherein the beta-glucosidase variant comprises a substitution at one or more positions corresponding to positions 100, 283, 456, and 512 of the mature polypeptide of SEQ ID NO: 6, wherein the variant has beta-glucosidase activity.

[6] The enzyme composition of paragraph 5, wherein the parent beta-glucosidase of the variant is (a) a polypeptide comprising or consisting of the mature polypeptide of SEQ ID NO: 6; (b) a polypeptide having at least 80% sequence identity to the mature polypeptide of SEQ ID NO: 6; (c) a polypeptide encoded by a polynucleotide that hybridizes under high or very high stringency conditions with (i) the mature polypeptide coding sequence of SEQ ID NO: 5, (ii) the cDNA sequence contained in the mature polypeptide coding sequence of SEQ ID NO: 5, or (iii) the full-length complementary strand of (i) or (ii); (d) a polypeptide encoded by a polynucleotide having at least 80% sequence identity to the mature polypeptide coding sequence of SEQ ID NO: 5 or the cDNA sequence thereof; or (e) a fragment of the mature polypeptide of SEQ ID NO: 6, which has beta-glucosidase activity.

[7] The enzyme composition of paragraph 5 or 6, wherein the variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100%, sequence identity to the amino acid sequence of the parent beta-glucosidase.

[8] The enzyme composition of any of paragraphs 5-7, wherein the variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100% sequence identity to the mature polypeptide of SEQ ID NO: 6.

[9] The enzyme composition of any of paragraphs 5-8, wherein the number of substitutions is 1-4, such as 1, 2, 3, or 4 substitutions.

[10] The enzyme composition of any of paragraphs 5-9, wherein the variant comprises a substitution at a position corresponding to position 100, a substitution at a position corresponding to position 283, a substitution at a position corresponding to position 456, and/or a substitution at a position corresponding to position 512.

[11] The enzyme composition of paragraph 10, wherein the substitution at the position corresponding to position 100 is Ser; the substitution at the position corresponding to position 456 is Gly; the substitution at the position corresponding to position 456 is Gln; and the substitution at the position corresponding to position 512 is Gly.

[12] The enzyme composition of any of paragraphs 5-11, wherein the variant comprises one or more (several) substitutions selected from the group consisting of G142S, Q183R, H266Q, and D703G.

[13] The enzyme composition of any of paragraphs 5-12, wherein the variant comprises the substitutions G142S and Q183R; G142S and H266Q; G142S and D703G; Q183R and H266Q; Q183R and D703G; H266Q and D703G; G142S, Q183R, and H266Q; G142S, Q183R, and D703G; G142S, H266Q, and D703G; Q183R, H266Q, and D703G; or G142S, Q183R, H266Q, and D703G.

[14] The enzyme composition of paragraph 1, wherein the *Penicillium* sp. GH61 polypeptide having cellulolytic enhancing activity or homolog thereof is selected from the group consisting of: (i) a GH61 polypeptide having cellulolytic enhancing activity comprising or consisting of the mature polypeptide of SEQ ID NO: 6; (ii) a GH61 polypeptide having cellulolytic enhancing activity comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 8; (iii) a GH61 polypeptide having cellulolytic enhancing activity encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 7; and (iv) a GH61 polypeptide having cellulolytic enhancing activity encoded by a polynucleotide that hybridizes under at least high stringency conditions, e.g., very high stringency conditions, with the mature polypeptide coding sequence of SEQ ID NO: 7 or the full-length complement thereof.

[15] The enzyme composition of any of paragraphs 1-14, which further comprises one or more enzymes selected from the group consisting of: (i) an *Aspergillus fumigatus* xylanase or homolog thereof; (ii) an *Aspergillus fumigatus* beta-xylosidase or homolog thereof; or (iii) a combination of (i) and (ii).

[16] The enzyme composition of paragraph 15, wherein the *Aspergillus fumigatus* xylanase or homolog thereof is selected from the group consisting of: (i) an *Aspergillus fumigatus* xylanase comprising or consisting of the mature polypeptide of SEQ ID NO: 10, SEQ ID NO: 12, or SEQ ID NO: 14; (ii) a xylanase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 10, SEQ ID NO: 12, or SEQ ID NO: 14; (iii) a xylanase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 9, SEQ ID NO: 11, or SEQ ID NO: 13; and (iv) a xylanase encoded by a polynucleotide that hybridizes under at least high stringency conditions, e.g., very high stringency conditions, with the mature polypeptide coding sequence of SEQ ID NO: 9, SEQ ID NO: 11, or SEQ ID NO: 13; or the full-length complement thereof.

[17] The enzyme composition of paragraph 15, wherein the *Aspergillus fumigatus* beta-xylosidase or homolog thereof is selected from the group consisting of: (i) a beta-xylosidase comprising or consisting of the mature polypeptide of SEQ ID NO: 16; (ii) a beta-xylosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 16; (iii) a beta-xylosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 15; and (iv) a beta-xylosidase encoded by a polynucleotide that hybridizes under at least high stringency conditions, e.g., very high stringency conditions, with the mature polypeptide coding sequence of SEQ ID NO: 15 or the full-length complement thereof.

[18] The enzyme composition of any of paragraphs 1-17, which further comprises one or more enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

[19] The enzyme composition of paragraph 18, wherein the cellulase is one or more enzymes selected from the group consisting of an endoglucanase, a cellobiohydrolase, and a beta-glucosidase.

[20] The enzyme composition of paragraph 19, wherein the endoglucanase is an endoglucanase I.

[21] The enzyme composition of paragraph 19, wherein the endoglucanase is an endoglucanase II.

[22] The enzyme composition of paragraph 18, wherein the hemicellulase is one or more enzymes selected from the group consisting of a xylanase, an acetylxylan esterase, a feruloyl esterase, an arabinofuranosidase, a xylosidase, and a glucuronidase.

[23] A recombinant filamentous fungal host cell, comprising polynucleotides encoding: (i) an *Aspergillus fumigatus* cellobiohydrolase I; (ii) an *Aspergillus fumigatus* cellobiohydrolase II; (iii) an *Aspergillus fumigatus* beta-glucosidase or variant thereof; and (iv) a *Penicillium* sp. GH61 polypeptide having cellulolytic enhancing activity; or homologs thereof.

[24] The recombinant filamentous fungal host cell of paragraph 23, wherein the *Aspergillus fumigatus* cellobiohydrolase I or homolog thereof is selected from the group consisting of: (i) a cellobiohydrolase I comprising or consisting of the mature polypeptide of SEQ ID NO: 2; (ii) a cellobiohydrolase I comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 2; (iii) a cellobiohydrolase I encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 1; and (iv) a cellobiohydrolase I encoded by a polynucleotide that hybridizes under at least high stringency conditions, e.g., very high stringency conditions, with the mature polypeptide coding sequence of SEQ ID NO: 1 or the full-length complement thereof.

[25] The recombinant filamentous fungal host cell of paragraph 23, wherein the *Aspergillus fumigatus* cellobiohydrolase II or homolog thereof is selected from the group consisting of: (i) a cellobiohydrolase II comprising or consisting of the mature polypeptide of SEQ ID NO: 4; (ii) a cellobiohydrolase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 4; (iii) a cellobiohydrolase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 3; and (iv) a cellobiohydrolase II encoded by a polynucleotide that hybridizes under at least high stringency conditions, e.g., very high stringency conditions, with the mature polypeptide coding sequence of SEQ ID NO: 3 or the full-length complement thereof.

[26] The recombinant filamentous fungal host cell of paragraph 23, wherein the *Aspergillus fumigatus* beta-glucosidase or homolog thereof is selected from the group consisting of: (i) a beta-glucosidase comprising or consisting of the mature polypeptide of SEQ ID NO: 6; (ii) a beta-glucosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 6; (iii) a beta-glucosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 5; and (iv) a beta-glucosidase encoded by a polynucleotide that hybridizes under at least high stringency conditions, e.g., very high stringency conditions, with the mature polypeptide coding sequence of SEQ ID NO: 5 or the full-length complement thereof.

[27] The recombinant filamentous fungal host cell of paragraph 23, wherein the beta-glucosidase variant comprises a substitution at one or more positions corresponding to positions 100, 283, 456, and 512 of the mature polypeptide of SEQ ID NO: 6, wherein the variant has beta-glucosidase activity.

[28] The recombinant filamentous fungal host cell of paragraph 27, wherein the parent beta-glucosidase of the variant is (a) a polypeptide comprising or consisting of the mature polypeptide of SEQ ID NO: 6; (b) a polypeptide having at least 80% sequence identity to the mature polypeptide of SEQ ID NO: 6; (c) a polypeptide encoded by a polynucleotide that hybridizes under high or very high stringency conditions with (i) the mature polypeptide coding sequence of SEQ ID NO: 5, (ii) the cDNA sequence contained in the mature polypeptide coding sequence of SEQ ID NO: 5, or (iii) the full-length complementary strand of (i) or (ii); (d) a polypeptide encoded by a polynucleotide having at least 80% sequence identity to the mature polypeptide coding sequence of SEQ ID NO: 5 or the cDNA sequence thereof; or (e) a fragment of the mature polypeptide of SEQ ID NO: 6, which has beta-glucosidase activity.

[29] The recombinant filamentous fungal host cell of paragraph 27 or 28, wherein the variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100%, sequence identity to the amino acid sequence of the parent beta-glucosidase.

[30] The recombinant filamentous fungal host cell of any of paragraphs 27-29, wherein the variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100% sequence identity to the mature polypeptide of SEQ ID NO: 6.

[31] The recombinant filamentous fungal host cell of any of paragraphs 27-30, wherein the number of substitutions is 1-4, such as 1, 2, 3, or 4 substitutions.

[32] The recombinant filamentous fungal host cell of any of paragraphs 27-31, wherein the variant comprises a substitution at a position corresponding to position 100, a substitution at a position corresponding to position 283, a substitution at a position corresponding to position 456, and/or a substitution at a position corresponding to position 512.

[33] The recombinant filamentous fungal host cell of paragraph 32, wherein the substitution at the position corresponding to position 100 is Ser; the substitution at the position corresponding to position 456 is Gly; the substitution at the position corresponding to position 456 is Gln; and the substitution at the position corresponding to position 512 is Gly.

[34] The recombinant filamentous fungal host cell of any of paragraphs 27-33, wherein the variant comprises one or more (several) substitutions selected from the group consisting of G142S, Q183R, H266Q, and D703G.

[35] The recombinant filamentous fungal host cell of any of paragraphs 27-34, wherein the variant comprises the substitutions G142S and Q183R; G142S and H266Q; G142S and D703G; Q183R and H266Q; Q183R and D703G; H266Q and D703G; G142S, Q183R, and H266Q; G142S, Q183R, and D703G; G142S, H266Q, and D703G; Q183R, H266Q, and D703G; or G142S, Q183R, H266Q, and D703G.

[36] The recombinant filamentous fungal host cell of paragraph 23, wherein the *Penicillium* sp. GH61 polypeptide having cellulolytic enhancing activity or homolog thereof is selected from the group consisting of: (i) a GH61 polypeptide having cellulolytic enhancing activity comprising or consisting of the mature polypeptide of SEQ ID NO: 8; (ii) a GH61 polypeptide having cellulolytic enhancing activity comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 8; (iii) a GH61 polypeptide having cellulolytic enhancing activity encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 7; and (iv) a GH61 polypeptide having cellulolytic enhancing activity encoded by a polynucleotide that hybridizes under at least high stringency conditions, e.g., very high stringency conditions, with the mature polypeptide coding sequence of SEQ ID NO: 7 or the full-length complement thereof.

[37] The recombinant filamentous fungal host cell of any of paragraphs 23-36, which further comprises one or more polynucleotides encoding one or more enzymes selected from the group consisting of: (i) an *Aspergillus fumigatus* xylanase; (ii) an *Aspergillus fumigatus* beta-xylosidase; and (iii) a combination of (i) and (ii).

[38] The recombinant filamentous fungal host cell of paragraph 37, wherein the *Aspergillus fumigatus* xylanase or homolog thereof is selected from the group consisting of: (i) an *Aspergillus fumigatus* xylanase comprising or consisting of the mature polypeptide of SEQ ID NO: 10, SEQ ID NO: 12, or SEQ ID NO: 14; (ii) a xylanase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 10, SEQ ID NO: 12, or SEQ ID NO:; (iii) a xylanase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 9, SEQ ID NO: 11, or SEQ ID NO: 13; and (iv) a xylanase encoded by a polynucleotide that hybridizes under at least high stringency conditions, e.g., very high stringency conditions, with the mature polypeptide coding sequence of SEQ ID NO: 9, SEQ ID NO: 11, or SEQ ID NO: 13; or the full-length complement thereof.

[39] The recombinant filamentous fungal host cell of paragraph 37, wherein the *Aspergillus fumigatus* beta-xylosidase or homolog thereof is selected from the group consisting of: (i) a beta-xylosidase comprising or consisting of the mature polypeptide of SEQ ID NO: 16; (ii) a beta-xylosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 16; (iii) a beta-xylosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 15; and (iv) a beta-xylosidase encoded by a polynucleotide that hybridizes under at least high stringency conditions, e.g., very high stringency conditions, with the mature polypeptide coding sequence of SEQ ID NO: 15 or the full-length complement thereof.

[40] The recombinant filamentous fungal host cell of any of paragraphs 23-39, which is a *Trichoderma* cell.

[41] The recombinant filamentous fungal host cell of paragraph 40, wherein the *Trichoderma* cell is selected from the group consisting of *Trichoderma harzianum*, *Trichoderma koningii*, *Trichoderma longibrachiatum*, *Trichoderma reesei*, and *Trichoderma viride*.

[42] The recombinant filamentous fungal host cell of paragraph 40, which is *Trichoderma reesei*.

[43] The recombinant filamentous fungal host cell of any of paragraphs 23-42, wherein one or more of the cellulase genes, one or more of hemicellulase genes, or a combination thereof, endogenous to the filamentous fungal host cell have been inactivated.

[44] The recombinant filamentous fungal host cell of paragraph 43, wherein a cellobiohydrolase I gene has been inactivated.

[45] The recombinant filamentous fungal host cell of paragraph 44, wherein the cellobiohydrolase I gene encodes a cellobiohydrolase I selected from the group consisting of: (i) a cellobiohydrolase I comprising or consisting of the mature polypeptide of SEQ ID NO: 18; (ii) a cellobiohydrolase I comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 18; (iii) a cellobiohydrolase I encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 17; and (iv) a cellobiohydrolase I encoded by a polynucleotide that hybridizes under at least high stringency conditions, e.g., very high stringency conditions, with the mature polypeptide coding sequence of SEQ ID NO: 17 or the full-length complement thereof.

[46] The recombinant filamentous fungal host cell of any of paragraphs 43-45, wherein a cellobiohydrolase II gene has been inactivated.

[47] The recombinant filamentous fungal host cell of paragraph 46, wherein the cellobiohydrolase II gene encodes a cellobiohydrolase II selected from the group consisting of: (i) a cellobiohydrolase I comprising or consisting of the mature polypeptide of SEQ ID NO: 20; (ii) a cellobiohydrolase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 20; (iii) a cellobiohydrolase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 19; and (iv) a cellobiohydrolase II encoded by a polynucleotide that hybridizes under at least high stringency conditions, e.g., very high stringency conditions, with the mature polypeptide coding sequence of SEQ ID NO: 19 or the full-length complement thereof.

[48] The recombinant filamentous fungal host cell of any of paragraphs 43-47, wherein a beta-glucosidase gene has been inactivated.

[49] The recombinant filamentous fungal host cell of paragraph 48, wherein the beta-glucosidase gene encodes a beta-glucosidase selected from the group consisting of: (i) a beta-glucosidase comprising or consisting of the mature polypeptide of SEQ ID NO: 22; (ii) a beta-glucosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 22; (iii) a beta-glucosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 21; and (iv) a beta-glucosidase encoded by a polynucleotide that hybridizes under at least high stringency conditions, e.g., very high stringency conditions, with the mature polypeptide coding sequence of SEQ ID NO: 21 or the full-length complement thereof.

[50] The recombinant filamentous fungal host cell of any of paragraphs 43-49, wherein a xylanase I gene has been inactivated.

[51] The recombinant filamentous fungal host cell of paragraph 50, wherein the xylanase I gene encodes a xylanase I selected from the group consisting of: (i) a xylanase I comprising or consisting of the mature polypeptide of SEQ ID NO: 24; (ii) a xylanase I comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 24; (iii) a xylanase I encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 23; and (iv) a xylanase I encoded by a polynucleotide that hybridizes under at least high stringency conditions, e.g., very high stringency conditions, with the mature polypeptide coding sequence of SEQ ID NO: 23 or the full-length complement thereof.

[52] The recombinant filamentous fungal host cell of any of paragraphs 43-51, wherein a xylanase II gene has been inactivated.

[53] The recombinant filamentous fungal host cell of paragraph 52, wherein the xylanase II gene encodes a xylanase II selected from the group consisting of: (i) a xylanase II comprising or consisting of the mature polypeptide of SEQ ID NO: 26; (ii) a xylanase II comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 26; (iii) a xylanase II encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 25; and (iv) a xylanase II encoded by a polynucleotide that hybridizes under at least high stringency conditions, e.g., very high stringency conditions, with the mature polypeptide coding sequence of SEQ ID NO: 25 or the full-length complement thereof.

[54] The recombinant filamentous fungal host cell of any of paragraphs 43-53, wherein a *Trichoderma reesei* xylanase III gene has been inactivated.

[55] The recombinant filamentous fungal host cell of paragraph 54, wherein the xylanase III gene encodes a xylanase III selected from the group consisting of: (i) a xylanase III comprising or consisting of the mature polypeptide of SEQ ID NO: 28; (ii) a xylanase III comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 28; (iii) a xylanase III encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 27; and (iv) a xylanase III encoded by a polynucleotide that hybridizes under at least high stringency conditions, e.g., very high stringency conditions, with the mature polypeptide coding sequence of SEQ ID NO: 27 or the full-length complement thereof.

[56] The recombinant filamentous fungal host cell of any of paragraphs 43-55, wherein a beta-xylosidase gene has been inactivated.

[57] The recombinant filamentous fungal host cell of paragraph 56, wherein the beta-xylosidase gene encodes a beta-xylosidase selected from the group consisting of: (i) a beta-xylosidase comprising or consisting of the mature polypeptide of SEQ ID NO: 30 (ii) a beta-xylosidase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 30; (iii) a beta-xylosidase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide coding sequence of SEQ ID NO: 29; and (iv) a beta-xylosidase encoded by a polynucleotide that hybridizes under at least high stringency conditions, e.g., very high stringency conditions, with the mature polypeptide coding sequence of SEQ ID NO: 29 or the full-length complement thereof.

[58] The recombinant filamentous fungal host cell of any of paragraphs 23-55, which further comprises one or more polynucleotides encoding one or more enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

[59] The recombinant filamentous fungal host cell of paragraph 58, wherein the cellulase is one or more enzymes selected from the group consisting of an endoglucanase, a cellobiohydrolase, and a beta-glucosidase.

[60] The recombinant filamentous fungal host cell of paragraph 58, wherein the hemicellulase is one or more enzymes selected from the group consisting of a xylanase, an acetylxylan esterase, a feruloyl esterase, an arabinofuranosidase, a xylosidase, and a glucuronidase.

[61] The recombinant filamentous fungal host cell of any of paragraphs 58-60, wherein one or more of the enzymes are native to the filamentous fungal host cell.

[62] The recombinant filamentous fungal host cell of paragraph 61, wherein the enzyme native to the filamentous fungal host cell is an endoglucanase.

[63] The recombinant filamentous fungal host cell of paragraph 62, wherein the endoglucanase is an endoglucanase I.

[64] The recombinant filamentous fungal host cell of paragraph 62, wherein the endoglucanase is an endoglucanase II.

[65] A method of producing an enzyme composition, comprising: (a) cultivating the host cell of any of paragraphs 23-64 under conditions conducive for production of the enzyme composition; and optionally (b) recovering the enzyme composition.

[66] A process for degrading a cellulosic material, comprising: treating the cellulosic material with the enzyme composition of any of paragraphs 1-22.

[67] The process of paragraph 66, wherein the cellulosic material is pretreated.

[68] The process of paragraph 66 or 67, further comprising recovering the degraded cellulosic material.

[69] The process of paragraph 68, wherein the degraded cellulosic material is a sugar

[70] The process of paragraph 69, wherein the sugar is selected from the group consisting of glucose, xylose, mannose, galactose, and arabinose.

[71] A process for producing a fermentation product, comprising: (a) saccharifying a cellulosic material with the enzyme composition of any of paragraphs 1-22; (b) fermenting the saccharified cellulosic material with one or more fermenting microorganisms to produce the fermentation product; and (c) recovering the fermentation product from the fermentation.

[72] The process of paragraph 71, wherein the cellulosic material is pretreated.

[73] The process of paragraph 71 or 72, wherein steps (a) and (b) are performed simultaneously in a simultaneous saccharification and fermentation.

[74] The process of any of paragraphs 71-73, wherein the fermentation product is an alcohol, an alkane, a cycloalkane, an alkene, an amino acid, a gas, isoprene, a ketone, an organic acid, or polyketide.

[75] A process of fermenting a cellulosic material, comprising: fermenting the cellulosic material with one or more fermenting microorganisms, wherein the cellulosic material is saccharified with the enzyme composition of any of paragraphs 1-22.

[76] The process of paragraph 75, wherein the fermenting of the cellulosic material produces a fermentation product.

[77] The process of paragraph 76, further comprising recovering the fermentation product from the fermentation.

[78] The process of paragraph 76 or 77, wherein the fermentation product is an alcohol, an alkane, a cycloalkane, an alkene, an amino acid, a gas, isoprene, a ketone, an organic acid, or polyketide.

[79] The process of any of paragraphs 75-78, wherein the cellulosic material is pretreated before saccharification.

[80] The enzyme composition of paragraphs 47-49, further comprising a *Trichoderma* endoglucanase I, a *Trichoderma* endoglucanase II, or a *Trichoderma* endoglucanase I and a *Trichoderma* endoglucanase II.

[81] The enzyme composition of paragraph 80, wherein the *Trichoderma* endoglucanase I is a *Trichoderma reesei* endoglucanase I.

[82] The enzyme composition of paragraph 80, wherein the *Trichoderma* endoglucanase II is a *Trichoderma reesei* endoglucanase II.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An enzyme composition comprising one or more enzymes selected from the group consisting of: (i) an *Aspergillus fumigatus* xylanase or homolog thereof, (ii) an *Aspergillus fumigatus* beta-xylosidase or homolog thereof; or (iii) a combination of (i) and (ii);
wherein the *Aspergillus fumigatus* xylanase or homolog thereof is selected from the group consisting of:
(i) an *Aspergillus fumigatus* xylanase comprising or consisting of the mature polypeptide of SEQ ID NO: 10, SEQ ID NO: 12, or SEQ ID NO: 14;
(ii) a xylanase comprising or consisting of an amino acid sequence having at least 70% sequence identity to the mature polypeptide of SEQ ID NO: 10, SEQ ID NO: 12, or SEQ ID NO: 14;
(iii) a xylanase encoded by a polynucleotide comprising or consisting of a nucleotide sequence having at least 70% sequence identity to the mature polypeptide coding sequence of SEQ ID NO: 9, SEQ ID NO: 11, or SEQ ID NO: 13; and
(iv) a xylanase encoded by a polynucleotide that hybridizes under at least high stringency conditions, very high stringency conditions, with the mature polypeptide coding sequence of SEQ ID NO: 9, SEQ ID NO: 11, or SEQ ID NO: 13; or the full-length complement thereof; and
wherein the *Aspergillus fumigatus* beta-xylosidase or homolog thereof is selected from the group consisting of:
(i) a beta-xylosidase comprising or consisting of the mature polypeptide of SEQ ID NO: 16;
(ii) a beta-xylosidase comprising or consisting of an amino acid sequence having at least 70% sequence identity to the mature polypeptide of SEQ ID NO: 16;
(iii) a beta-xylosidase encoded by a polynucleotide comprising or consisting of a nucleotide sequence having at least 70% sequence identity to the mature polypeptide coding sequence of SEQ ID NO: 15; and
(iv) a beta-xylosidase encoded by a polynucleotide that hybridizes under at least high stringency conditions, very high stringency conditions, with the mature polypeptide coding sequence of SEQ ID NO: 15 or the full-length complement thereof.

2. The enzyme composition of claim 1, which further comprises one or more enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

3. The enzyme composition of claim 1, wherein the xylanase comprises or consists of an amino acid sequence having at least 75% sequence identity to the mature polypeptide of SEQ ID NO: 10, SEQ ID NO: 12, or SEQ ID NO: 14.

4. The enzyme composition of claim 1, wherein the xylanase comprises or consists of an amino acid sequence having at least 80% sequence identity to the mature polypeptide of SEQ ID NO: 10, SEQ ID NO: 12, or SEQ ID NO: 14.

5. The enzyme composition of claim 1, wherein the xylanase comprises or consists of an amino acid sequence having at least 85% sequence identity to the mature polypeptide of SEQ ID NO: 10, SEQ ID NO: 12, or SEQ ID NO: 14.

6. The enzyme composition of claim 1, wherein the xylanase comprises or consists of an amino acid sequence having at least 90% sequence identity to the mature polypeptide of SEQ ID NO: 10, SEQ ID NO: 12, or SEQ ID NO: 14.

7. The enzyme composition of claim 1, wherein the xylanase comprises or consists of an amino acid sequence having at least 95% sequence identity to the mature polypeptide of SEQ ID NO: 10, SEQ ID NO: 12, or SEQ ID NO: 14.

8. The enzyme composition of claim 1, wherein the xylanase comprises or consists of an amino acid sequence having at least 99% sequence identity to the mature polypeptide of SEQ ID NO: 10, SEQ ID NO: 12, or SEQ ID NO: 14.

9. The enzyme composition of claim 1, wherein the xylanase is encoded by a polynucleotide comprising or consisting of a nucleotide sequence having at least 75% sequence identity to the mature polypeptide coding sequence of SEQ ID NO: 9, SEQ ID NO: 11, or SEQ ID NO: 13.

10. The enzyme composition of claim 1, wherein the xylanase is encoded by a polynucleotide comprising or consisting of a nucleotide sequence having at least 80% sequence identity to the mature polypeptide coding sequence of SEQ ID NO: 9, SEQ ID NO: 11, or SEQ ID NO: 13.

11. The enzyme composition of claim 1, wherein the xylanase is encoded by a polynucleotide comprising or consisting of a nucleotide sequence having at least 85% sequence identity to the mature polypeptide coding sequence of SEQ ID NO: 9, SEQ ID NO: 11, or SEQ ID NO: 13.

12. The enzyme composition of claim 1, wherein the xylanase is encoded by a polynucleotide comprising or consisting of a nucleotide sequence having at least 90% sequence identity to the mature polypeptide coding sequence of SEQ ID NO: 9, SEQ ID NO: 11, or SEQ ID NO: 13.

13. The enzyme composition of claim 1, wherein the xylanase is encoded by a polynucleotide comprising or consisting of a nucleotide sequence having at least 95% sequence identity to the mature polypeptide coding sequence of SEQ ID NO: 9, SEQ ID NO: 11, or SEQ ID NO: 13.

14. The enzyme composition of claim 1, wherein the xylanase is encoded by a polynucleotide comprising or consisting of a nucleotide sequence having at least 99% sequence identity to the mature polypeptide coding sequence of SEQ ID NO: 9, SEQ ID NO: 11, or SEQ ID NO: 13.

15. The enzyme composition of claim 1, wherein the beta-xylosidase comprises or consists of an amino acid sequence having at least 75% sequence identity to the mature polypeptide of SEQ ID NO: 16.

16. The enzyme composition of claim 1, wherein the beta-xylosidase comprises or consists of an amino acid sequence having at least 80% sequence identity to the mature polypeptide of SEQ ID NO: 16.

17. The enzyme composition of claim 1, wherein the beta-xylosidase comprises or consists of an amino acid sequence having at least 85% sequence identity to the mature polypeptide of SEQ ID NO: 16.

18. The enzyme composition of claim 1, wherein the beta-xylosidase comprises or consists of an amino acid sequence having at least 90% sequence identity to the mature polypeptide of SEQ ID NO: 16.

19. The enzyme composition of claim 1, wherein the beta-xylosidase comprises or consists of an amino acid sequence having at least 95% sequence identity to the mature polypeptide of SEQ ID NO: 16.

20. The enzyme composition of claim 1, wherein the beta-xylosidase comprises or consists of an amino acid sequence having at least 99% sequence identity to the mature polypeptide of SEQ ID NO: 16.

21. The enzyme composition of claim 1, wherein the beta-xylosidase is encoded by a polynucleotide comprising or consisting of a nucleotide sequence having at least 75% sequence identity to the mature polypeptide coding sequence of SEQ ID NO: 15.

22. The enzyme composition of claim 1, wherein the beta-xylosidase is encoded by a polynucleotide comprising or consisting of a nucleotide sequence having at least 80% sequence identity to the mature polypeptide coding sequence of SEQ ID NO: 15.

23. The enzyme composition of claim 1, wherein the beta-xylosidase is encoded by a polynucleotide comprising or consisting of a nucleotide sequence having at least 85% sequence identity to the mature polypeptide coding sequence of SEQ ID NO: 15.

24. The enzyme composition of claim 1, wherein the beta-xylosidase is encoded by a polynucleotide comprising or consisting of a nucleotide sequence having at least 90% sequence identity to the mature polypeptide coding sequence of SEQ ID NO: 15.

25. The enzyme composition of claim 1, wherein the beta-xylosidase is encoded by a polynucleotide comprising or consisting of a nucleotide sequence having at least 95% sequence identity to the mature polypeptide coding sequence of SEQ ID NO: 15.

26. The enzyme composition of claim 1, wherein the beta-xylosidase is encoded by a polynucleotide comprising or consisting of a nucleotide sequence having at least 99% sequence identity to the mature polypeptide coding sequence of SEQ ID NO: 15.

\* \* \* \* \*